US012781205B2

(12) United States Patent
Robson et al.

(10) Patent No.: US 12,781,205 B2
(45) Date of Patent: Nov. 3, 2026

(54) COMPOSITIONS AND METHODS FOR DECREASING INFLAMMATION

(71) Applicant: Beth Israel Deaconess Medical Center, Inc., Boston, MA (US)

(72) Inventors: Simon C. Robson, Boston, MA (US); Elizabeth H. Zhong, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 682 days.

(21) Appl. No.: 18/020,342

(22) PCT Filed: Aug. 13, 2021

(86) PCT No.: PCT/US2021/045956

§ 371 (c)(1),
(2) Date: Feb. 8, 2023

(87) PCT Pub. No.: WO2022/036229

PCT Pub. Date: Feb. 17, 2022

(65) Prior Publication Data

US 2023/0287365 A1 Sep. 14, 2023

Related U.S. Application Data

(60) Provisional application No. 63/066,117, filed on Aug. 14, 2020.

(51) Int. Cl.

| | |
|---|---|
| ***C12N 9/14*** | (2006.01) |
| ***A61K 38/46*** | (2006.01) |
| ***A61P 29/00*** | (2006.01) |
| ***C12N 9/16*** | (2006.01) |
| ***C12N 15/52*** | (2006.01) |
| ***C12N 15/62*** | (2006.01) |

(52) U.S. Cl.

CPC ................ *C12N 9/14* (2013.01); *A61K 38/46* (2013.01); *A61K 38/465* (2013.01); *A61P 29/00* (2018.01); *C12N 9/16* (2013.01); *C12N 15/52* (2013.01); *C12N 15/62* (2013.01); *C12Y 301/03005* (2013.01); *C12Y 306/01005* (2013.01); *C07K 2319/30* (2013.01)

(58) Field of Classification Search

CPC . C12N 9/14; C12N 9/16; C12N 15/62; A61K 38/46; C12Y 301/03005; C12Y 306/01005; C07K 2319/00

See application file for complete search history.

(56) References Cited

U.S. PATENT DOCUMENTS

| | | | |
|---|---|---|---|
| 7,785,618 B2 | 8/2010 | Elmaleh et al. | |
| 2005/0037382 A1 | 2/2005 | Robson et al. | |
| 2005/0158280 A1 | 7/2005 | Robson et al. | |
| 2015/0190481 A1* | 7/2015 | Finn ............... | C12Y 301/03005 424/94.6 |

OTHER PUBLICATIONS

International Search Report and Written Opinion of the International Searching Authority for International Application No. PCT/US2021/045956, mailed on Mar. 9, 2022 (14 pages).

* cited by examiner

*Primary Examiner* — Peter J Reddig

(74) *Attorney, Agent, or Firm* — Clark+Elbing LLP

(57) ABSTRACT

The present invention features bifunctional, soluble ecto-enzymes that are engineered to hydrolyze extracellular nucleotide triphosphates (e.g., ATP) to a nucleoside (e.g., adenosine), through the fusion of the ectodomains (ECD) of an ecto-nucleoside triphosphate diphosphohydrolase (E-NTPDase) and a nucleotide monophosphatase (NMPAse), such as an ecto-5' nucleotidase (eN), alkaline phosphatase (ALP), or an acid phosphatase (AP). Also described are methods of use thereof, e.g. for limiting and decreasing inflammation and sequelae.

25 Claims, 47 Drawing Sheets

Specification includes a Sequence Listing.

SEQUENCE LISTING

```
<160> NUMBER OF SEQ ID NOS: 46

<210> SEQ ID NO 1
<211> LENGTH: 439
<212> TYPE: PRT
<213> ORGANISM: Homo sapiens

<400> SEQUENCE: 1

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
                165                 170                 175

Leu Gly Gly Ala Ser Thr Gln Val Thr Phe Val Pro Gln Asn Gln Thr
            180                 185                 190

Ile Glu Ser Pro Asp Asn Ala Leu Gln Phe Arg Leu Tyr Gly Lys Asp
        195                 200                 205

Tyr Asn Val Tyr Thr His Ser Phe Leu Cys Tyr Gly Lys Asp Gln Ala
    210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
                245                 250                 255

Ser Asp Leu Tyr Lys Thr Pro Cys Thr Lys Arg Phe Glu Met Thr Leu
            260                 265                 270

Pro Phe Gln Gln Phe Glu Ile Gln Gly Ile Gly Asn Tyr Gln Gln Cys
        275                 280                 285

His Gln Ser Ile Leu Glu Leu Phe Asn Thr Ser Tyr Cys Pro Tyr Ser
```

-continued

```
    290                 295                 300

Gln Cys Ala Phe Asn Gly Ile Phe Leu Pro Pro Leu Gln Gly Asp Phe
305                 310                 315                 320

Gly Ala Phe Ser Ala Phe Tyr Phe Val Met Lys Phe Leu Asn Leu Thr
                325                 330                 335

Ser Glu Lys Val Ser Gln Glu Lys Val Thr Glu Met Met Lys Lys Phe
            340                 345                 350

Cys Ala Gln Pro Trp Glu Glu Ile Lys Thr Ser Tyr Ala Gly Val Lys
        355                 360                 365

Glu Lys Tyr Leu Ser Glu Tyr Cys Phe Ser Gly Thr Tyr Ile Leu Ser
    370                 375                 380

Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
                405                 410                 415

Tyr Met Leu Asn Leu Thr Asn Met Ile Pro Ala Glu Gln Pro Leu Ser
            420                 425                 430

Thr Pro Leu Ser His Ser Thr
        435


<210> SEQ ID NO 2
<211> LENGTH: 523
<212> TYPE: PRT
<213> ORGANISM: Homo sapiens

<400> SEQUENCE: 2

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Val Gly Gly His Ser Asn Thr Phe Leu Tyr Thr
    210                 215                 220
```

Gly Asn Pro Pro Ser Lys Glu Val Pro Ala Gly Lys Tyr Pro Phe Ile
225 230 235 240

Val Thr Ser Asp Asp Gly Arg Lys Val Pro Val Val Gln Ala Tyr Ala
245 250 255

Phe Gly Lys Tyr Leu Gly Tyr Leu Lys Ile Glu Phe Asp Glu Arg Gly
260 265 270

Asn Val Ile Ser Ser His Gly Asn Pro Ile Leu Leu Asn Ser Ser Ile
275 280 285

Pro Glu Asp Pro Ser Ile Lys Ala Asp Ile Asn Lys Trp Arg Ile Lys
290 295 300

Leu Asp Asn Tyr Ser Thr Gln Glu Leu Gly Lys Thr Ile Val Tyr Leu
305 310 315 320

Asp Gly Ser Ser Gln Ser Cys Arg Phe Arg Glu Cys Asn Met Gly Asn
325 330 335

Leu Ile Cys Asp Ala Met Ile Asn Asn Asn Leu Arg His Ala Asp Glu
340 345 350

Thr Phe Trp Asn His Val Ser Met Cys Ile Leu Asn Gly Gly Gly Ile
355 360 365

Arg Ser Pro Ile Asp Glu Arg Asn Asn Gly Thr Ile Thr Trp Glu Asn
370 375 380

Leu Ala Ala Val Leu Pro Phe Gly Gly Thr Phe Asp Leu Val Gln Leu
385 390 395 400

Lys Gly Ser Thr Leu Lys Lys Ala Phe Glu His Ser Val His Arg Tyr
405 410 415

Gly Gln Ser Thr Gly Glu Phe Leu Gln Val Gly Gly Ile His Val Val
420 425 430

Tyr Asp Leu Ser Arg Lys Pro Gly Asp Arg Val Val Lys Leu Asp Val
435 440 445

Leu Cys Thr Lys Cys Arg Val Pro Ser Tyr Asp Pro Leu Lys Met Asp
450 455 460

Glu Val Tyr Lys Val Ile Leu Pro Asn Phe Leu Ala Asn Gly Gly Asp
465 470 475 480

Gly Phe Gln Met Ile Lys Asp Glu Leu Leu Arg His Asp Ser Gly Asp
485 490 495

Gln Asp Ile Asn Val Val Ser Thr Tyr Ile Ser Lys Met Lys Val Ile
500 505 510

Tyr Pro Ala Val Glu Gly Arg Ile Lys Phe Ser
515 520

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Gly Gly Gly Gly
1

<210> SEQ ID NO 4
<211> LENGTH: 16
<212> TYPE: PRT
<213> ORGANISM: Homo sapiens

<400> SEQUENCE: 4

Met Pro Leu Leu Leu Leu Leu Leu Leu Leu Pro Ser Pro Leu His Gly

-continued 1 5 10 15

<210> SEQ ID NO 5
<211> LENGTH: 210
<212> TYPE: PRT
<213> ORGANISM: Homo sapiens

<400> SEQUENCE: 5

Pro Ser Val Phe Leu Phe Pro Pro Lys Pro Lys Asp Thr Leu Met Ile
1 5 10 15

Ser Arg Thr Pro Glu Val Thr Cys Val Val Val Asp Val Ser His Glu
20 25 30

Asp Pro Glu Val Lys Phe Asn Trp Tyr Val Asp Gly Val Glu Val His
35 40 45

Asn Ala Lys Thr Lys Pro Arg Glu Glu Gln Tyr Asn Ser Thr Tyr Arg
50 55 60

Val Val Ser Val Leu Thr Val Leu His Gln Asp Trp Leu Asn Gly Lys
65 70 75 80

Glu Tyr Lys Cys Lys Val Ser Asn Lys Ala Leu Pro Ala Pro Ile Glu
85 90 95

Lys Thr Ile Ser Lys Ala Lys Gly Gln Pro Arg Glu Pro Gln Val Tyr
100 105 110

Thr Leu Pro Pro Ser Arg Glu Glu Met Thr Lys Asn Gln Val Asn Leu
115 120 125

Thr Cys Leu Val Lys Gly Phe Tyr Pro Ser Asp Ile Ala Val Glu Trp
130 135 140

Glu Ser Asn Gly Gln Pro Glu Asn Asn Tyr Lys Thr Thr Pro Pro Val
145 150 155 160

Leu Asp Ser Asp Gly Ser Phe Phe Leu Asn Ser Thr Leu Thr Val Asp
165 170 175

Lys Ser Arg Trp Gln Gln Gly Asn Val Phe Ser Cys Ser Val Met His
180 185 190

Glu Ala Leu His Asn His Tyr Thr Gln Lys Ser Leu Ser Leu Ser Pro
195 200 205

Gly Lys
210

<210> SEQ ID NO 6
<211> LENGTH: 214
<212> TYPE: PRT
<213> ORGANISM: Artificial Sequence
<220> FEATURE:
<223> OTHER INFORMATION: Synthetic Construct

<400> SEQUENCE: 6

Gly Gly Gly Gly Pro Ser Val Phe Leu Phe Pro Pro Lys Pro Lys Asp
1 5 10 15

Thr Leu Met Ile Ser Arg Thr Pro Glu Val Thr Cys Val Val Val Asp
20 25 30

Val Ser His Glu Asp Pro Glu Val Lys Phe Asn Trp Tyr Val Asp Gly
35 40 45

Val Glu Val His Asn Ala Lys Thr Lys Pro Arg Glu Glu Gln Tyr Asn
50 55 60

Ser Thr Tyr Arg Val Val Ser Val Leu Thr Val Leu His Gln Asp Trp
65 70 75 80

Leu Asn Gly Lys Glu Tyr Lys Cys Lys Val Ser Asn Lys Ala Leu Pro
85 90 95

```
Ala Pro Ile Glu Lys Thr Ile Ser Lys Ala Lys Gly Gln Pro Arg Glu
            100                 105                 110

Pro Gln Val Tyr Thr Leu Pro Pro Ser Arg Glu Glu Met Thr Lys Asn
        115                 120                 125

Gln Val Asn Leu Thr Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Asn Ser Thr
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Gly Lys
    210


<210> SEQ ID NO 7
<211> LENGTH: 218
<212> TYPE: PRT
<213> ORGANISM: Artificial Sequence
<220> FEATURE:
<223> OTHER INFORMATION: Synthetic Construct

<400> SEQUENCE: 7

Gly Gly Gly Gly Pro Ser Val Phe Leu Phe Pro Pro Lys Pro Lys Asp
1               5                   10                  15

Thr Leu Met Ile Ser Arg Thr Pro Glu Val Thr Cys Val Val Val Asp
            20                  25                  30

Val Ser His Glu Asp Pro Glu Val Lys Phe Asn Trp Tyr Val Asp Gly
        35                  40                  45

Val Glu Val His Asn Ala Lys Thr Lys Pro Arg Glu Glu Gln Tyr Asn
    50                  55                  60

Ser Thr Tyr Arg Val Val Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys Gly Gln Pro Arg Glu
            100                 105                 110

Pro Gln Val Tyr Thr Leu Pro Pro Ser Arg Glu Glu Met Thr Lys Asn
        115                 120                 125

Gln Val Asn Leu Thr Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Asn Ser Thr
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Gly Lys Gly Gly Gly Gly
    210                 215


<210> SEQ ID NO 8
```

-continued

<211> LENGTH: 1196
<212> TYPE: PRT
<213> ORGANISM: Artificial Sequence
<220> FEATURE:
<223> OTHER INFORMATION: Synthetic Construct

<400> SEQUENCE: 8

```
Met Pro Leu Leu Leu Leu Leu Leu Leu Leu Pro Ser Pro Leu His Gly
1               5                   10                  15

Thr Gln Asn Lys Ala Leu Pro Glu Asn Val Lys Tyr Gly Ile Val Leu
            20                  25                  30

Asp Ala Gly Ser Ser His Thr Ser Leu Tyr Ile Tyr Lys Trp Pro Ala
        35                  40                  45

Glu Lys Glu Asn Asp Thr Gly Val Val His Gln Val Glu Glu Cys Arg
    50                  55                  60

Val Lys Gly Pro Gly Ile Ser Lys Phe Val Gln Lys Val Asn Glu Ile
65                  70                  75                  80

Gly Ile Tyr Leu Thr Asp Cys Met Glu Arg Ala Arg Glu Val Ile Pro
                85                  90                  95

Arg Ser Gln His Gln Glu Thr Pro Val Tyr Leu Gly Ala Thr Ala Gly
            100                 105                 110

Met Arg Leu Leu Arg Met Glu Ser Glu Glu Leu Ala Asp Arg Val Leu
        115                 120                 125

Asp Val Val Glu Arg Ser Leu Ser Asn Tyr Pro Phe Asp Phe Gln Gly
    130                 135                 140

Ala Arg Ile Ile Thr Gly Gln Glu Glu Gly Ala Tyr Gly Trp Ile Thr
145                 150                 155                 160

Ile Asn Tyr Leu Leu Gly Lys Phe Ser Gln Lys Thr Arg Trp Phe Ser
                165                 170                 175

Ile Val Pro Tyr Glu Thr Asn Asn Gln Glu Thr Phe Gly Ala Leu Asp
            180                 185                 190

Leu Gly Gly Ala Ser Thr Gln Val Thr Phe Val Pro Gln Asn Gln Thr
        195                 200                 205

Ile Glu Ser Pro Asp Asn Ala Leu Gln Phe Arg Leu Tyr Gly Lys Asp
    210                 215                 220

Tyr Asn Val Tyr Thr His Ser Phe Leu Cys Tyr Gly Lys Asp Gln Ala
225                 230                 235                 240

Leu Trp Gln Lys Leu Ala Lys Asp Ile Gln Val Ala Ser Asn Glu Ile
                245                 250                 255

Leu Arg Asp Pro Cys Phe His Pro Gly Tyr Lys Lys Val Val Asn Val
            260                 265                 270

Ser Asp Leu Tyr Lys Thr Pro Cys Thr Lys Arg Phe Glu Met Thr Leu
        275                 280                 285

Pro Phe Gln Gln Phe Glu Ile Gln Gly Ile Gly Asn Tyr Gln Gln Cys
    290                 295                 300

His Gln Ser Ile Leu Glu Leu Phe Asn Thr Ser Tyr Cys Pro Tyr Ser
305                 310                 315                 320

Gln Cys Ala Phe Asn Gly Ile Phe Leu Pro Pro Leu Gln Gly Asp Phe
                325                 330                 335

Gly Ala Phe Ser Ala Phe Tyr Phe Val Met Lys Phe Leu Asn Leu Thr
            340                 345                 350

Ser Glu Lys Val Ser Gln Glu Lys Val Thr Glu Met Met Lys Lys Phe
        355                 360                 365

Cys Ala Gln Pro Trp Glu Glu Ile Lys Thr Ser Tyr Ala Gly Val Lys
    370                 375                 380
```

-continued

```
Glu Lys Tyr Leu Ser Glu Tyr Cys Phe Ser Gly Thr Tyr Ile Leu Ser
385                 390                 395                 400

Leu Leu Leu Gln Gly Tyr His Phe Thr Ala Asp Ser Trp Glu His Ile
                405                 410                 415

His Phe Ile Gly Lys Ile Gln Gly Ser Asp Ala Gly Trp Thr Leu Gly
            420                 425                 430

Tyr Met Leu Asn Leu Thr Asn Met Ile Pro Ala Glu Gln Pro Leu Ser
        435                 440                 445

Thr Pro Leu Ser His Ser Thr Gly Gly Gly Gly Trp Glu Leu Thr Ile
    450                 455                 460

Leu His Thr Asn Asp Val His Ser Arg Leu Glu Gln Thr Ser Glu Asp
465                 470                 475                 480

Ser Ser Lys Cys Val Asn Ala Ser Arg Cys Met Gly Gly Val Ala Arg
                485                 490                 495

Leu Phe Thr Lys Val Gln Gln Ile Arg Arg Ala Glu Pro Asn Val Leu
            500                 505                 510

Leu Leu Asp Ala Gly Asp Gln Tyr Gln Gly Thr Ile Trp Phe Thr Val
        515                 520                 525

Tyr Lys Gly Ala Glu Val Ala His Phe Met Asn Ala Leu Arg Tyr Asp
    530                 535                 540

Ala Met Ala Leu Gly Asn His Glu Phe Asp Asn Gly Val Glu Gly Leu
545                 550                 555                 560

Ile Glu Pro Leu Leu Lys Glu Ala Lys Phe Pro Ile Leu Ser Ala Asn
                565                 570                 575

Ile Lys Ala Lys Gly Pro Leu Ala Ser Gln Ile Ser Gly Leu Tyr Leu
            580                 585                 590

Pro Tyr Lys Val Leu Pro Val Gly Asp Glu Val Val Gly Ile Val Gly
        595                 600                 605

Tyr Thr Ser Lys Glu Thr Pro Phe Leu Ser Asn Pro Gly Thr Asn Leu
    610                 615                 620

Val Phe Glu Asp Glu Ile Thr Ala Leu Gln Pro Glu Val Asp Lys Leu
625                 630                 635                 640

Lys Thr Leu Asn Val Asn Lys Ile Ile Ala Leu Gly His Ser Gly Phe
                645                 650                 655

Glu Met Asp Lys Leu Ile Ala Gln Lys Val Arg Gly Val Asp Val Val
            660                 665                 670

Val Gly Gly His Ser Asn Thr Phe Leu Tyr Thr Gly Asn Pro Pro Ser
        675                 680                 685

Lys Glu Val Pro Ala Gly Lys Tyr Pro Phe Ile Val Thr Ser Asp Asp
    690                 695                 700

Gly Arg Lys Val Pro Val Val Gln Ala Tyr Ala Phe Gly Lys Tyr Leu
705                 710                 715                 720

Gly Tyr Leu Lys Ile Glu Phe Asp Glu Arg Gly Asn Val Ile Ser Ser
                725                 730                 735

His Gly Asn Pro Ile Leu Leu Asn Ser Ser Ile Pro Glu Asp Pro Ser
            740                 745                 750

Ile Lys Ala Asp Ile Asn Lys Trp Arg Ile Lys Leu Asp Asn Tyr Ser
        755                 760                 765

Thr Gln Glu Leu Gly Lys Thr Ile Val Tyr Leu Asp Gly Ser Ser Gln
    770                 775                 780

Ser Cys Arg Phe Arg Glu Cys Asn Met Gly Asn Leu Ile Cys Asp Ala
785                 790                 795                 800
```

-continued

```
Met Ile Asn Asn Asn Leu Arg His Ala Asp Glu Thr Phe Trp Asn His
                805                 810                 815

Val Ser Met Cys Ile Leu Asn Gly Gly Gly Ile Arg Ser Pro Ile Asp
            820                 825                 830

Glu Arg Asn Asn Gly Thr Ile Thr Trp Glu Asn Leu Ala Ala Val Leu
        835                 840                 845

Pro Phe Gly Gly Thr Phe Asp Leu Val Gln Leu Lys Gly Ser Thr Leu
    850                 855                 860

Lys Lys Ala Phe Glu His Ser Val His Arg Tyr Gly Gln Ser Thr Gly
865                 870                 875                 880

Glu Phe Leu Gln Val Gly Gly Ile His Val Val Tyr Asp Leu Ser Arg
                885                 890                 895

Lys Pro Gly Asp Arg Val Val Lys Leu Asp Val Leu Cys Thr Lys Cys
            900                 905                 910

Arg Val Pro Ser Tyr Asp Pro Leu Lys Met Asp Glu Val Tyr Lys Val
        915                 920                 925

Ile Leu Pro Asn Phe Leu Ala Asn Gly Gly Asp Gly Phe Gln Met Ile
    930                 935                 940

Lys Asp Glu Leu Leu Arg His Asp Ser Gly Asp Gln Asp Ile Asn Val
945                 950                 955                 960

Val Ser Thr Tyr Ile Ser Lys Met Lys Val Ile Tyr Pro Ala Val Glu
                965                 970                 975

Gly Arg Ile Lys Phe Ser Gly Gly Gly Gly Pro Ser Val Phe Leu Phe
            980                 985                 990

Pro Pro Lys Pro Lys Asp Thr Leu  Met Ile Ser Arg Thr  Pro Glu Val
        995                 1000                1005

Thr Cys  Val Val Val Asp Val  Ser His Glu Asp Pro  Glu Val Lys
    1010                 1015                 1020

Phe Asn  Trp Tyr Val Asp Gly  Val Glu Val His Asn  Ala Lys Thr
    1025                 1030                 1035

Lys Pro  Arg Glu Glu Gln Tyr  Asn Ser Thr Tyr Arg  Val Val Ser
    1040                 1045                 1050

Val Leu  Thr Val Leu His Gln  Asp Trp Leu Asn Gly  Lys Glu Tyr
    1055                 1060                 1065

Lys Cys  Lys Val Ser Asn Lys  Ala Leu Pro Ala Pro  Ile Glu Lys
    1070                 1075                 1080

Thr Ile  Ser Lys Ala Lys Gly  Gln Pro Arg Glu Pro  Gln Val Tyr
    1085                 1090                 1095

Thr Leu  Pro Pro Ser Arg Glu  Glu Met Thr Lys Asn  Gln Val Asn
    1100                 1105                 1110

Leu Thr  Cys Leu Val Lys Gly  Phe Tyr Pro Ser Asp  Ile Ala Val
    1115                 1120                 1125

Glu Trp  Glu Ser Asn Gly Gln  Pro Glu Asn Asn Tyr  Lys Thr Thr
    1130                 1135                 1140

Pro Pro  Val Leu Asp Ser Asp  Gly Ser Phe Phe Leu  Asn Ser Thr
    1145                 1150                 1155

Leu Thr  Val Asp Lys Ser Arg  Trp Gln Gln Gly Asn  Val Phe Ser
    1160                 1165                 1170

Cys Ser  Val Met His Glu Ala  Leu His Asn His Tyr  Thr Gln Lys
    1175                 1180                 1185

Ser Leu  Ser Leu Ser Pro Gly  Lys
    1190                 1195
```

<210> SEQ ID NO 9
<211> LENGTH: 1196
<212> TYPE: PRT
<213> ORGANISM: Artificial Sequence
<220> FEATURE:
<223> OTHER INFORMATION: Synthetic Construct

<400> SEQUENCE: 9

```
Met Pro Leu Leu Leu Leu Leu Leu Leu Leu Pro Ser Pro Leu His Gly
1               5                   10                  15

Trp Glu Leu Thr Ile Leu His Thr Asn Asp Val His Ser Arg Leu Glu
            20                  25                  30

Gln Thr Ser Glu Asp Ser Ser Lys Cys Val Asn Ala Ser Arg Cys Met
        35                  40                  45

Gly Gly Val Ala Arg Leu Phe Thr Lys Val Gln Gln Ile Arg Arg Ala
    50                  55                  60

Glu Pro Asn Val Leu Leu Leu Asp Ala Gly Asp Gln Tyr Gln Gly Thr
65                  70                  75                  80

Ile Trp Phe Thr Val Tyr Lys Gly Ala Glu Val Ala His Phe Met Asn
                85                  90                  95

Ala Leu Arg Tyr Asp Ala Met Ala Leu Gly Asn His Glu Phe Asp Asn
            100                 105                 110

Gly Val Glu Gly Leu Ile Glu Pro Leu Leu Lys Glu Ala Lys Phe Pro
        115                 120                 125

Ile Leu Ser Ala Asn Ile Lys Ala Lys Gly Pro Leu Ala Ser Gln Ile
    130                 135                 140

Ser Gly Leu Tyr Leu Pro Tyr Lys Val Leu Pro Val Gly Asp Glu Val
145                 150                 155                 160

Val Gly Ile Val Gly Tyr Thr Ser Lys Glu Thr Pro Phe Leu Ser Asn
                165                 170                 175

Pro Gly Thr Asn Leu Val Phe Glu Asp Glu Ile Thr Ala Leu Gln Pro
            180                 185                 190

Glu Val Asp Lys Leu Lys Thr Leu Asn Val Asn Lys Ile Ile Ala Leu
        195                 200                 205

Gly His Ser Gly Phe Glu Met Asp Lys Leu Ile Ala Gln Lys Val Arg
    210                 215                 220

Gly Val Asp Val Val Val Gly Gly His Ser Asn Thr Phe Leu Tyr Thr
225                 230                 235                 240

Gly Asn Pro Pro Ser Lys Glu Val Pro Ala Gly Lys Tyr Pro Phe Ile
                245                 250                 255

Val Thr Ser Asp Asp Gly Arg Lys Val Pro Val Val Gln Ala Tyr Ala
            260                 265                 270

Phe Gly Lys Tyr Leu Gly Tyr Leu Lys Ile Glu Phe Asp Glu Arg Gly
        275                 280                 285

Asn Val Ile Ser Ser His Gly Asn Pro Ile Leu Leu Asn Ser Ser Ile
    290                 295                 300

Pro Glu Asp Pro Ser Ile Lys Ala Asp Ile Asn Lys Trp Arg Ile Lys
305                 310                 315                 320

Leu Asp Asn Tyr Ser Thr Gln Glu Leu Gly Lys Thr Ile Val Tyr Leu
                325                 330                 335

Asp Gly Ser Ser Gln Ser Cys Arg Phe Arg Glu Cys Asn Met Gly Asn
            340                 345                 350

Leu Ile Cys Asp Ala Met Ile Asn Asn Asn Leu Arg His Ala Asp Glu
        355                 360                 365

Thr Phe Trp Asn His Val Ser Met Cys Ile Leu Asn Gly Gly Gly Ile
```

-continued

```
    370                 375                 380

Arg Ser Pro Ile Asp Glu Arg Asn Asn Gly Thr Ile Thr Trp Glu Asn
385                 390                 395                 400

Leu Ala Ala Val Leu Pro Phe Gly Gly Thr Phe Asp Leu Val Gln Leu
                405                 410                 415

Lys Gly Ser Thr Leu Lys Lys Ala Phe Glu His Ser Val His Arg Tyr
            420                 425                 430

Gly Gln Ser Thr Gly Glu Phe Leu Gln Val Gly Gly Ile His Val Val
        435                 440                 445

Tyr Asp Leu Ser Arg Lys Pro Gly Asp Arg Val Val Lys Leu Asp Val
    450                 455                 460

Leu Cys Thr Lys Cys Arg Val Pro Ser Tyr Asp Pro Leu Lys Met Asp
465                 470                 475                 480

Glu Val Tyr Lys Val Ile Leu Pro Asn Phe Leu Ala Asn Gly Gly Asp
                485                 490                 495

Gly Phe Gln Met Ile Lys Asp Glu Leu Leu Arg His Asp Ser Gly Asp
            500                 505                 510

Gln Asp Ile Asn Val Val Ser Thr Tyr Ile Ser Lys Met Lys Val Ile
        515                 520                 525

Tyr Pro Ala Val Glu Gly Arg Ile Lys Phe Ser Gly Gly Gly Gly Thr
    530                 535                 540

Gln Asn Lys Ala Leu Pro Glu Asn Val Lys Tyr Gly Ile Val Leu Asp
545                 550                 555                 560

Ala Gly Ser Ser His Thr Ser Leu Tyr Ile Tyr Lys Trp Pro Ala Glu
                565                 570                 575

Lys Glu Asn Asp Thr Gly Val Val His Gln Val Glu Glu Cys Arg Val
            580                 585                 590

Lys Gly Pro Gly Ile Ser Lys Phe Val Gln Lys Val Asn Glu Ile Gly
        595                 600                 605

Ile Tyr Leu Thr Asp Cys Met Glu Arg Ala Arg Glu Val Ile Pro Arg
    610                 615                 620

Ser Gln His Gln Glu Thr Pro Val Tyr Leu Gly Ala Thr Ala Gly Met
625                 630                 635                 640

Arg Leu Leu Arg Met Glu Ser Glu Glu Leu Ala Asp Arg Val Leu Asp
                645                 650                 655

Val Val Glu Arg Ser Leu Ser Asn Tyr Pro Phe Asp Phe Gln Gly Ala
            660                 665                 670

Arg Ile Ile Thr Gly Gln Glu Glu Gly Ala Tyr Gly Trp Ile Thr Ile
        675                 680                 685

Asn Tyr Leu Leu Gly Lys Phe Ser Gln Lys Thr Arg Trp Phe Ser Ile
    690                 695                 700

Val Pro Tyr Glu Thr Asn Asn Gln Glu Thr Phe Gly Ala Leu Asp Leu
705                 710                 715                 720

Gly Gly Ala Ser Thr Gln Val Thr Phe Val Pro Gln Asn Gln Thr Ile
                725                 730                 735

Glu Ser Pro Asp Asn Ala Leu Gln Phe Arg Leu Tyr Gly Lys Asp Tyr
            740                 745                 750

Asn Val Tyr Thr His Ser Phe Leu Cys Tyr Gly Lys Asp Gln Ala Leu
        755                 760                 765

Trp Gln Lys Leu Ala Lys Asp Ile Gln Val Ala Ser Asn Glu Ile Leu
    770                 775                 780

Arg Asp Pro Cys Phe His Pro Gly Tyr Lys Lys Val Val Asn Val Ser
785                 790                 795                 800
```

```
Asp Leu Tyr Lys Thr Pro Cys Thr Lys Arg Phe Glu Met Thr Leu Pro
                805                 810                 815

Phe Gln Gln Phe Glu Ile Gln Gly Ile Gly Asn Tyr Gln Gln Cys His
            820                 825                 830

Gln Ser Ile Leu Glu Leu Phe Asn Thr Ser Tyr Cys Pro Tyr Ser Gln
        835                 840                 845

Cys Ala Phe Asn Gly Ile Phe Leu Pro Pro Leu Gln Gly Asp Phe Gly
    850                 855                 860

Ala Phe Ser Ala Phe Tyr Phe Val Met Lys Phe Leu Asn Leu Thr Ser
865                 870                 875                 880

Glu Lys Val Ser Gln Glu Lys Val Thr Glu Met Met Lys Lys Phe Cys
                885                 890                 895

Ala Gln Pro Trp Glu Glu Ile Lys Thr Ser Tyr Ala Gly Val Lys Glu
            900                 905                 910

Lys Tyr Leu Ser Glu Tyr Cys Phe Ser Gly Thr Tyr Ile Leu Ser Leu
        915                 920                 925

Leu Leu Gln Gly Tyr His Phe Thr Ala Asp Ser Trp Glu His Ile His
    930                 935                 940

Phe Ile Gly Lys Ile Gln Gly Ser Asp Ala Gly Trp Thr Leu Gly Tyr
945                 950                 955                 960

Met Leu Asn Leu Thr Asn Met Ile Pro Ala Glu Gln Pro Leu Ser Thr
                965                 970                 975

Pro Leu Ser His Ser Thr Gly Gly Gly Gly Pro Ser Val Phe Leu Phe
            980                 985                 990

Pro Pro Lys Pro Lys Asp Thr Leu  Met Ile Ser Arg Thr  Pro Glu Val
        995                 1000                1005

Thr Cys  Val Val Val Asp Val  Ser His Glu Asp Pro  Glu Val Lys
    1010                1015                1020

Phe Asn  Trp Tyr Val Asp Gly  Val Glu Val His Asn  Ala Lys Thr
    1025                1030                1035

Lys Pro  Arg Glu Glu Gln Tyr  Asn Ser Thr Tyr Arg  Val Val Ser
    1040                1045                1050

Val Leu  Thr Val Leu His Gln  Asp Trp Leu Asn Gly  Lys Glu Tyr
    1055                1060                1065

Lys Cys  Lys Val Ser Asn Lys  Ala Leu Pro Ala Pro  Ile Glu Lys
    1070                1075                1080

Thr Ile  Ser Lys Ala Lys Gly  Gln Pro Arg Glu Pro  Gln Val Tyr
    1085                1090                1095

Thr Leu  Pro Pro Ser Arg Glu  Glu Met Thr Lys Asn  Gln Val Asn
    1100                1105                1110

Leu Thr  Cys Leu Val Lys Gly  Phe Tyr Pro Ser Asp  Ile Ala Val
    1115                1120                1125

Glu Trp  Glu Ser Asn Gly Gln  Pro Glu Asn Asn Tyr  Lys Thr Thr
    1130                1135                1140

Pro Pro  Val Leu Asp Ser Asp  Gly Ser Phe Phe Leu  Asn Ser Thr
    1145                1150                1155

Leu Thr  Val Asp Lys Ser Arg  Trp Gln Gln Gly Asn  Val Phe Ser
    1160                1165                1170

Cys Ser  Val Met His Glu Ala  Leu His Asn His Tyr  Thr Gln Lys
    1175                1180                1185

Ser Leu  Ser Leu Ser Pro Gly  Lys
    1190                1195
```

<210> SEQ ID NO 10
<211> LENGTH: 1196
<212> TYPE: PRT
<213> ORGANISM: Artificial Sequence
<220> FEATURE:
<223> OTHER INFORMATION: Synthetic Construct

<400> SEQUENCE: 10

```
Met Pro Leu Leu Leu Leu Leu Leu Leu Leu Pro Ser Pro Leu His Gly
1               5                   10                  15

Thr Gln Asn Lys Ala Leu Pro Glu Asn Val Lys Tyr Gly Ile Val Leu
            20                  25                  30

Asp Ala Gly Ser Ser His Thr Ser Leu Tyr Ile Tyr Lys Trp Pro Ala
        35                  40                  45

Glu Lys Glu Asn Asp Thr Gly Val Val His Gln Val Glu Glu Cys Arg
    50                  55                  60

Val Lys Gly Pro Gly Ile Ser Lys Phe Val Gln Lys Val Asn Glu Ile
65                  70                  75                  80

Gly Ile Tyr Leu Thr Asp Cys Met Glu Arg Ala Arg Glu Val Ile Pro
                85                  90                  95

Arg Ser Gln His Gln Glu Thr Pro Val Tyr Leu Gly Ala Thr Ala Gly
            100                 105                 110

Met Arg Leu Leu Arg Met Glu Ser Glu Glu Leu Ala Asp Arg Val Leu
        115                 120                 125

Asp Val Val Glu Arg Ser Leu Ser Asn Tyr Pro Phe Asp Phe Gln Gly
    130                 135                 140

Ala Arg Ile Ile Thr Gly Gln Glu Glu Gly Ala Tyr Gly Trp Ile Thr
145                 150                 155                 160

Ile Asn Tyr Leu Leu Gly Lys Phe Ser Gln Lys Thr Arg Trp Phe Ser
                165                 170                 175

Ile Val Pro Tyr Glu Thr Asn Asn Gln Glu Thr Phe Gly Ala Leu Asp
            180                 185                 190

Leu Gly Gly Ala Ser Thr Gln Val Thr Phe Val Pro Gln Asn Gln Thr
        195                 200                 205

Ile Glu Ser Pro Asp Asn Ala Leu Gln Phe Arg Leu Tyr Gly Lys Asp
    210                 215                 220

Tyr Asn Val Tyr Thr His Ser Phe Leu Cys Tyr Gly Lys Asp Gln Ala
225                 230                 235                 240

Leu Trp Gln Lys Leu Ala Lys Asp Ile Gln Val Ala Ser Asn Glu Ile
                245                 250                 255

Leu Arg Asp Pro Cys Phe His Pro Gly Tyr Lys Lys Val Val Asn Val
            260                 265                 270

Ser Asp Leu Tyr Lys Thr Pro Cys Thr Lys Arg Phe Glu Met Thr Leu
        275                 280                 285

Pro Phe Gln Gln Phe Glu Ile Gln Gly Ile Gly Asn Tyr Gln Gln Cys
    290                 295                 300

His Gln Ser Ile Leu Glu Leu Phe Asn Thr Ser Tyr Cys Pro Tyr Ser
305                 310                 315                 320

Gln Cys Ala Phe Asn Gly Ile Phe Leu Pro Pro Leu Gln Gly Asp Phe
                325                 330                 335

Gly Ala Phe Ser Ala Phe Tyr Phe Val Met Lys Phe Leu Asn Leu Thr
            340                 345                 350

Ser Glu Lys Val Ser Gln Glu Lys Val Thr Glu Met Met Lys Lys Phe
        355                 360                 365
```

-continued

```
Cys Ala Gln Pro Trp Glu Glu Ile Lys Thr Ser Tyr Ala Gly Val Lys
    370                 375                 380

Glu Lys Tyr Leu Ser Glu Tyr Cys Phe Ser Gly Thr Tyr Ile Leu Ser
385                 390                 395                 400

Leu Leu Leu Gln Gly Tyr His Phe Thr Ala Asp Ser Trp Glu His Ile
                405                 410                 415

His Phe Ile Gly Lys Ile Gln Gly Ser Asp Ala Gly Trp Thr Leu Gly
            420                 425                 430

Tyr Met Leu Asn Leu Thr Asn Met Ile Pro Ala Glu Gln Pro Leu Ser
        435                 440                 445

Thr Pro Leu Ser His Ser Thr Gly Gly Gly Gly Pro Ser Val Phe Leu
    450                 455                 460

Phe Pro Pro Lys Pro Lys Asp Thr Leu Met Ile Ser Arg Thr Pro Glu
465                 470                 475                 480

Val Thr Cys Val Val Val Asp Val Ser His Glu Asp Pro Glu Val Lys
                485                 490                 495

Phe Asn Trp Tyr Val Asp Gly Val Glu Val His Asn Ala Lys Thr Lys
            500                 505                 510

Pro Arg Glu Glu Gln Tyr Asn Ser Thr Tyr Arg Val Val Ser Val Leu
        515                 520                 525

Thr Val Leu His Gln Asp Trp Leu Asn Gly Lys Glu Tyr Lys Cys Lys
    530                 535                 540

Val Ser Asn Lys Ala Leu Pro Ala Pro Ile Glu Lys Thr Ile Ser Lys
545                 550                 555                 560

Ala Lys Gly Gln Pro Arg Glu Pro Gln Val Tyr Thr Leu Pro Pro Ser
                565                 570                 575

Arg Glu Glu Met Thr Lys Asn Gln Val Asn Leu Thr Cys Leu Val Lys
            580                 585                 590

Gly Phe Tyr Pro Ser Asp Ile Ala Val Glu Trp Glu Ser Asn Gly Gln
        595                 600                 605

Pro Glu Asn Asn Tyr Lys Thr Thr Pro Pro Val Leu Asp Ser Asp Gly
    610                 615                 620

Ser Phe Phe Leu Asn Ser Thr Leu Thr Val Asp Lys Ser Arg Trp Gln
625                 630                 635                 640

Gln Gly Asn Val Phe Ser Cys Ser Val Met His Glu Ala Leu His Asn
                645                 650                 655

His Tyr Thr Gln Lys Ser Leu Ser Leu Ser Pro Gly Lys Gly Gly Gly
            660                 665                 670

Gly Trp Glu Leu Thr Ile Leu His Thr Asn Asp Val His Ser Arg Leu
        675                 680                 685

Glu Gln Thr Ser Glu Asp Ser Ser Lys Cys Val Asn Ala Ser Arg Cys
    690                 695                 700

Met Gly Gly Val Ala Arg Leu Phe Thr Lys Val Gln Gln Ile Arg Arg
705                 710                 715                 720

Ala Glu Pro Asn Val Leu Leu Leu Asp Ala Gly Asp Gln Tyr Gln Gly
                725                 730                 735

Thr Ile Trp Phe Thr Val Tyr Lys Gly Ala Glu Val Ala His Phe Met
            740                 745                 750

Asn Ala Leu Arg Tyr Asp Ala Met Ala Leu Gly Asn His Glu Phe Asp
        755                 760                 765

Asn Gly Val Glu Gly Leu Ile Glu Pro Leu Leu Lys Glu Ala Lys Phe
    770                 775                 780

Pro Ile Leu Ser Ala Asn Ile Lys Ala Lys Gly Pro Leu Ala Ser Gln
```

-continued

```
785                 790                 795                 800

Ile Ser Gly Leu Tyr Leu Pro Tyr Lys Val Leu Pro Val Gly Asp Glu
                805                 810                 815

Val Val Gly Ile Val Gly Tyr Thr Ser Lys Glu Thr Pro Phe Leu Ser
            820                 825                 830

Asn Pro Gly Thr Asn Leu Val Phe Glu Asp Glu Ile Thr Ala Leu Gln
        835                 840                 845

Pro Glu Val Asp Lys Leu Lys Thr Leu Asn Val Asn Lys Ile Ile Ala
    850                 855                 860

Leu Gly His Ser Gly Phe Glu Met Asp Lys Leu Ile Ala Gln Lys Val
865                 870                 875                 880

Arg Gly Val Asp Val Val Val Gly Gly His Ser Asn Thr Phe Leu Tyr
                885                 890                 895

Thr Gly Asn Pro Pro Ser Lys Glu Val Pro Ala Gly Lys Tyr Pro Phe
            900                 905                 910

Ile Val Thr Ser Asp Asp Gly Arg Lys Val Pro Val Val Gln Ala Tyr
        915                 920                 925

Ala Phe Gly Lys Tyr Leu Gly Tyr Leu Lys Ile Glu Phe Asp Glu Arg
    930                 935                 940

Gly Asn Val Ile Ser Ser His Gly Asn Pro Ile Leu Leu Asn Ser Ser
945                 950                 955                 960

Ile Pro Glu Asp Pro Ser Ile Lys Ala Asp Ile Asn Lys Trp Arg Ile
                965                 970                 975

Lys Leu Asp Asn Tyr Ser Thr Gln Glu Leu Gly Lys Thr Ile Val Tyr
            980                 985                 990

Leu Asp Gly Ser Ser Gln Ser Cys  Arg Phe Arg Glu Cys  Asn Met Gly
        995                 1000                1005

Asn Leu  Ile Cys Asp Ala Met  Ile Asn Asn Asn Leu  Arg His Ala
    1010                1015                1020

Asp Glu  Thr Phe Trp Asn His  Val Ser Met Cys Ile  Leu Asn Gly
    1025                1030                1035

Gly Gly  Ile Arg Ser Pro Ile  Asp Glu Arg Asn Asn  Gly Thr Ile
    1040                1045                1050

Thr Trp  Glu Asn Leu Ala Ala  Val Leu Pro Phe Gly  Gly Thr Phe
    1055                1060                1065

Asp Leu  Val Gln Leu Lys Gly  Ser Thr Leu Lys Lys  Ala Phe Glu
    1070                1075                1080

His Ser  Val His Arg Tyr Gly  Gln Ser Thr Gly Glu  Phe Leu Gln
    1085                1090                1095

Val Gly  Gly Ile His Val Val  Tyr Asp Leu Ser Arg  Lys Pro Gly
    1100                1105                1110

Asp Arg  Val Val Lys Leu Asp  Val Leu Cys Thr Lys  Cys Arg Val
    1115                1120                1125

Pro Ser  Tyr Asp Pro Leu Lys  Met Asp Glu Val Tyr  Lys Val Ile
    1130                1135                1140

Leu Pro  Asn Phe Leu Ala Asn  Gly Gly Asp Gly Phe  Gln Met Ile
    1145                1150                1155

Lys Asp  Glu Leu Leu Arg His  Asp Ser Gly Asp Gln  Asp Ile Asn
    1160                1165                1170

Val Val  Ser Thr Tyr Ile Ser  Lys Met Lys Val Ile  Tyr Pro Ala
    1175                1180                1185

Val Glu  Gly Arg Ile Lys Phe  Ser
    1190                1195
```

<210> SEQ ID NO 11
<211> LENGTH: 1196
<212> TYPE: PRT
<213> ORGANISM: Artificial Sequence
<220> FEATURE:
<223> OTHER INFORMATION: Synthetic Construct

<400> SEQUENCE: 11

```
Met Pro Leu Leu Leu Leu Leu Leu Leu Leu Pro Ser Pro Leu His Gly
1               5                   10                  15

Trp Glu Leu Thr Ile Leu His Thr Asn Asp Val His Ser Arg Leu Glu
            20                  25                  30

Gln Thr Ser Glu Asp Ser Ser Lys Cys Val Asn Ala Ser Arg Cys Met
        35                  40                  45

Gly Gly Val Ala Arg Leu Phe Thr Lys Val Gln Gln Ile Arg Arg Ala
    50                  55                  60

Glu Pro Asn Val Leu Leu Leu Asp Ala Gly Asp Gln Tyr Gln Gly Thr
65                  70                  75                  80

Ile Trp Phe Thr Val Tyr Lys Gly Ala Glu Val Ala His Phe Met Asn
                85                  90                  95

Ala Leu Arg Tyr Asp Ala Met Ala Leu Gly Asn His Glu Phe Asp Asn
            100                 105                 110

Gly Val Glu Gly Leu Ile Glu Pro Leu Leu Lys Glu Ala Lys Phe Pro
        115                 120                 125

Ile Leu Ser Ala Asn Ile Lys Ala Lys Gly Pro Leu Ala Ser Gln Ile
    130                 135                 140

Ser Gly Leu Tyr Leu Pro Tyr Lys Val Leu Pro Val Gly Asp Glu Val
145                 150                 155                 160

Val Gly Ile Val Gly Tyr Thr Ser Lys Glu Thr Pro Phe Leu Ser Asn
                165                 170                 175

Pro Gly Thr Asn Leu Val Phe Glu Asp Glu Ile Thr Ala Leu Gln Pro
            180                 185                 190

Glu Val Asp Lys Leu Lys Thr Leu Asn Val Asn Lys Ile Ile Ala Leu
        195                 200                 205

Gly His Ser Gly Phe Glu Met Asp Lys Leu Ile Ala Gln Lys Val Arg
    210                 215                 220

Gly Val Asp Val Val Val Gly Gly His Ser Asn Thr Phe Leu Tyr Thr
225                 230                 235                 240

Gly Asn Pro Pro Ser Lys Glu Val Pro Ala Gly Lys Tyr Pro Phe Ile
                245                 250                 255

Val Thr Ser Asp Asp Gly Arg Lys Val Pro Val Val Gln Ala Tyr Ala
            260                 265                 270

Phe Gly Lys Tyr Leu Gly Tyr Leu Lys Ile Glu Phe Asp Glu Arg Gly
        275                 280                 285

Asn Val Ile Ser Ser His Gly Asn Pro Ile Leu Leu Asn Ser Ser Ile
    290                 295                 300

Pro Glu Asp Pro Ser Ile Lys Ala Asp Ile Asn Lys Trp Arg Ile Lys
305                 310                 315                 320

Leu Asp Asn Tyr Ser Thr Gln Glu Leu Gly Lys Thr Ile Val Tyr Leu
                325                 330                 335

Asp Gly Ser Ser Gln Ser Cys Arg Phe Arg Glu Cys Asn Met Gly Asn
            340                 345                 350

Leu Ile Cys Asp Ala Met Ile Asn Asn Asn Leu Arg His Ala Asp Glu
        355                 360                 365
```

-continued

```
Thr Phe Trp Asn His Val Ser Met Cys Ile Leu Asn Gly Gly Gly Ile
    370                 375                 380

Arg Ser Pro Ile Asp Glu Arg Asn Asn Gly Thr Ile Thr Trp Glu Asn
385                 390                 395                 400

Leu Ala Ala Val Leu Pro Phe Gly Gly Thr Phe Asp Leu Val Gln Leu
                405                 410                 415

Lys Gly Ser Thr Leu Lys Lys Ala Phe Glu His Ser Val His Arg Tyr
            420                 425                 430

Gly Gln Ser Thr Gly Glu Phe Leu Gln Val Gly Gly Ile His Val Val
        435                 440                 445

Tyr Asp Leu Ser Arg Lys Pro Gly Asp Arg Val Val Lys Leu Asp Val
    450                 455                 460

Leu Cys Thr Lys Cys Arg Val Pro Ser Tyr Asp Pro Leu Lys Met Asp
465                 470                 475                 480

Glu Val Tyr Lys Val Ile Leu Pro Asn Phe Leu Ala Asn Gly Gly Asp
                485                 490                 495

Gly Phe Gln Met Ile Lys Asp Glu Leu Leu Arg His Asp Ser Gly Asp
            500                 505                 510

Gln Asp Ile Asn Val Val Ser Thr Tyr Ile Ser Lys Met Lys Val Ile
        515                 520                 525

Tyr Pro Ala Val Glu Gly Arg Ile Lys Phe Ser Gly Gly Gly Gly Pro
    530                 535                 540

Ser Val Phe Leu Phe Pro Pro Lys Pro Lys Asp Thr Leu Met Ile Ser
545                 550                 555                 560

Arg Thr Pro Glu Val Thr Cys Val Val Val Asp Val Ser His Glu Asp
                565                 570                 575

Pro Glu Val Lys Phe Asn Trp Tyr Val Asp Gly Val Glu Val His Asn
            580                 585                 590

Ala Lys Thr Lys Pro Arg Glu Glu Gln Tyr Asn Ser Thr Tyr Arg Val
        595                 600                 605

Val Ser Val Leu Thr Val Leu His Gln Asp Trp Leu Asn Gly Lys Glu
    610                 615                 620

Tyr Lys Cys Lys Val Ser Asn Lys Ala Leu Pro Ala Pro Ile Glu Lys
625                 630                 635                 640

Thr Ile Ser Lys Ala Lys Gly Gln Pro Arg Glu Pro Gln Val Tyr Thr
                645                 650                 655

Leu Pro Pro Ser Arg Glu Glu Met Thr Lys Asn Gln Val Asn Leu Thr
            660                 665                 670

Cys Leu Val Lys Gly Phe Tyr Pro Ser Asp Ile Ala Val Glu Trp Glu
        675                 680                 685

Ser Asn Gly Gln Pro Glu Asn Asn Tyr Lys Thr Thr Pro Pro Val Leu
    690                 695                 700

Asp Ser Asp Gly Ser Phe Phe Leu Asn Ser Thr Leu Thr Val Asp Lys
705                 710                 715                 720

Ser Arg Trp Gln Gln Gly Asn Val Phe Ser Cys Ser Val Met His Glu
                725                 730                 735

Ala Leu His Asn His Tyr Thr Gln Lys Ser Leu Ser Leu Ser Pro Gly
            740                 745                 750

Lys Gly Gly Gly Gly Thr Gln Asn Lys Ala Leu Pro Glu Asn Val Lys
        755                 760                 765

Tyr Gly Ile Val Leu Asp Ala Gly Ser Ser His Thr Ser Leu Tyr Ile
    770                 775                 780
```

-continued

```
Tyr Lys Trp Pro Ala Glu Lys Glu Asn Asp Thr Gly Val Val His Gln
785                 790                 795                 800

Val Glu Glu Cys Arg Val Lys Gly Pro Gly Ile Ser Lys Phe Val Gln
                805                 810                 815

Lys Val Asn Glu Ile Gly Ile Tyr Leu Thr Asp Cys Met Glu Arg Ala
            820                 825                 830

Arg Glu Val Ile Pro Arg Ser Gln His Gln Glu Thr Pro Val Tyr Leu
        835                 840                 845

Gly Ala Thr Ala Gly Met Arg Leu Leu Arg Met Glu Ser Glu Glu Leu
    850                 855                 860

Ala Asp Arg Val Leu Asp Val Val Glu Arg Ser Leu Ser Asn Tyr Pro
865                 870                 875                 880

Phe Asp Phe Gln Gly Ala Arg Ile Ile Thr Gly Gln Glu Glu Gly Ala
                885                 890                 895

Tyr Gly Trp Ile Thr Ile Asn Tyr Leu Leu Gly Lys Phe Ser Gln Lys
            900                 905                 910

Thr Arg Trp Phe Ser Ile Val Pro Tyr Glu Thr Asn Asn Gln Glu Thr
        915                 920                 925

Phe Gly Ala Leu Asp Leu Gly Gly Ala Ser Thr Gln Val Thr Phe Val
    930                 935                 940

Pro Gln Asn Gln Thr Ile Glu Ser Pro Asp Asn Ala Leu Gln Phe Arg
945                 950                 955                 960

Leu Tyr Gly Lys Asp Tyr Asn Val Tyr Thr His Ser Phe Leu Cys Tyr
                965                 970                 975

Gly Lys Asp Gln Ala Leu Trp Gln Lys Leu Ala Lys Asp Ile Gln Val
            980                 985                 990

Ala Ser Asn Glu Ile Leu Arg Asp  Pro Cys Phe His Pro  Gly Tyr Lys
        995                 1000                1005

Lys Val  Val Asn Val Ser Asp  Leu Tyr Lys Thr Pro  Cys Thr Lys
    1010                1015                1020

Arg Phe  Glu Met Thr Leu Pro  Phe Gln Gln Phe Glu  Ile Gln Gly
    1025                1030                1035

Ile Gly  Asn Tyr Gln Gln Cys  His Gln Ser Ile Leu  Glu Leu Phe
    1040                1045                1050

Asn Thr  Ser Tyr Cys Pro Tyr  Ser Gln Cys Ala Phe  Asn Gly Ile
    1055                1060                1065

Phe Leu  Pro Pro Leu Gln Gly  Asp Phe Gly Ala Phe  Ser Ala Phe
    1070                1075                1080

Tyr Phe  Val Met Lys Phe Leu  Asn Leu Thr Ser Glu  Lys Val Ser
    1085                1090                1095

Gln Glu  Lys Val Thr Glu Met  Met Lys Lys Phe Cys  Ala Gln Pro
    1100                1105                1110

Trp Glu  Glu Ile Lys Thr Ser  Tyr Ala Gly Val Lys  Glu Lys Tyr
    1115                1120                1125

Leu Ser  Glu Tyr Cys Phe Ser  Gly Thr Tyr Ile Leu  Ser Leu Leu
    1130                1135                1140

Leu Gln  Gly Tyr His Phe Thr  Ala Asp Ser Trp Glu  His Ile His
    1145                1150                1155

Phe Ile  Gly Lys Ile Gln Gly  Ser Asp Ala Gly Trp  Thr Leu Gly
    1160                1165                1170

Tyr Met  Leu Asn Leu Thr Asn  Met Ile Pro Ala Glu  Gln Pro Leu
    1175                1180                1185

Ser Thr  Pro Leu Ser His Ser  Thr
```

1190 1195

<210> SEQ ID NO 12
<211> LENGTH: 510
<212> TYPE: PRT
<213> ORGANISM: Homo sapiens

<400> SEQUENCE: 12

```
Met Glu Asp Thr Lys Glu Ser Asn Val Lys Thr Phe Cys Ser Lys Asn
1               5                   10                  15

Ile Leu Ala Ile Leu Gly Phe Ser Ser Ile Ile Ala Val Ile Ala Leu
            20                  25                  30

Leu Ala Val Gly Leu Thr Gln Asn Lys Ala Leu Pro Glu Asn Val Lys
        35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
        275                 280                 285

Lys Val Val Asn Val Ser Asp Leu Tyr Lys Thr Pro Cys Thr Lys Arg
    290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
        355                 360                 365
```

-continued

```
Phe Leu Asn Leu Thr Ser Glu Lys Val Ser Gln Glu Lys Val Thr Glu
    370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
            420                 425                 430

Ser Trp Glu His Ile His Phe Ile Gly Lys Ile Gln Gly Ser Asp Ala
        435                 440                 445

Gly Trp Thr Leu Gly Tyr Met Leu Asn Leu Thr Asn Met Ile Pro Ala
    450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
            500                 505                 510


<210> SEQ ID NO 13
<211> LENGTH: 574
<212> TYPE: PRT
<213> ORGANISM: Homo sapiens

<400> SEQUENCE: 13

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240
```

Gly Gly His Ser Asn Thr Phe Leu Tyr Thr Gly Asn Pro Pro Ser Lys
245 250 255

Glu Val Pro Ala Gly Lys Tyr Pro Phe Ile Val Thr Ser Asp Asp Gly
260 265 270

Arg Lys Val Pro Val Val Gln Ala Tyr Ala Phe Gly Lys Tyr Leu Gly
275 280 285

Tyr Leu Lys Ile Glu Phe Asp Glu Arg Gly Asn Val Ile Ser Ser His
290 295 300

Gly Asn Pro Ile Leu Leu Asn Ser Ser Ile Pro Glu Asp Pro Ser Ile
305 310 315 320

Lys Ala Asp Ile Asn Lys Trp Arg Ile Lys Leu Asp Asn Tyr Ser Thr
325 330 335

Gln Glu Leu Gly Lys Thr Ile Val Tyr Leu Asp Gly Ser Ser Gln Ser
340 345 350

Cys Arg Phe Arg Glu Cys Asn Met Gly Asn Leu Ile Cys Asp Ala Met
355 360 365

Ile Asn Asn Asn Leu Arg His Thr Asp Glu Met Phe Trp Asn His Val
370 375 380

Ser Met Cys Ile Leu Asn Gly Gly Gly Ile Arg Ser Pro Ile Asp Glu
385 390 395 400

Arg Asn Asn Gly Thr Ile Thr Trp Glu Asn Leu Ala Ala Val Leu Pro
405 410 415

Phe Gly Gly Thr Phe Asp Leu Val Gln Leu Lys Gly Ser Thr Leu Lys
420 425 430

Lys Ala Phe Glu His Ser Val His Arg Tyr Gly Gln Ser Thr Gly Glu
435 440 445

Phe Leu Gln Val Gly Gly Ile His Val Val Tyr Asp Leu Ser Arg Lys
450 455 460

Pro Gly Asp Arg Val Val Lys Leu Asp Val Leu Cys Thr Lys Cys Arg
465 470 475 480

Val Pro Ser Tyr Asp Pro Leu Lys Met Asp Glu Val Tyr Lys Val Ile
485 490 495

Leu Pro Asn Phe Leu Ala Asn Gly Gly Asp Gly Phe Gln Met Ile Lys
500 505 510

Asp Glu Leu Leu Arg His Asp Ser Gly Asp Gln Asp Ile Asn Val Val
515 520 525

Ser Thr Tyr Ile Ser Lys Met Lys Val Ile Tyr Pro Ala Val Glu Gly
530 535 540

Arg Ile Lys Phe Ser Thr Gly Ser His Cys His Gly Ser Phe Ser Leu
545 550 555 560

Ile Phe Leu Ser Leu Trp Ala Val Ile Phe Val Leu Tyr Gln
565 570

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Gly Gly Gly Gly Ser
1 5

<210> SEQ ID NO 15

-continued

<211> LENGTH: 4
<212> TYPE: PRT
<213> ORGANISM: Artificial Sequence
<220> FEATURE:
<223> OTHER INFORMATION: Synthetic Construct

<400> SEQUENCE: 15

Gly Gly Ser Gly
1

<210> SEQ ID NO 16
<211> LENGTH: 4
<212> TYPE: PRT
<213> ORGANISM: Artificial Sequence
<220> FEATURE:
<223> OTHER INFORMATION: Synthetic Construct

<400> SEQUENCE: 16

Ser Gly Gly Gly
1

<210> SEQ ID NO 17
<211> LENGTH: 4
<212> TYPE: PRT
<213> ORGANISM: Artificial Sequence
<220> FEATURE:
<223> OTHER INFORMATION: Synthetic Construct

<400> SEQUENCE: 17

Gly Ser Gly Ser
1

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct

<400> SEQUENCE: 18

Gly Ser Gly Ser Gly Ser
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Gly Ser Gly Ser Gly Ser Gly Ser
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Gly Ser Gly Ser Gly Ser Gly Ser Gly Ser
1               5                   10

<210> SEQ ID NO 21
<211> LENGTH: 12

<212> TYPE: PRT
<213> ORGANISM: Artificial Sequence
<220> FEATURE:
<223> OTHER INFORMATION: Synthetic Construct

<400> SEQUENCE: 21

Gly Ser Gly Ser Gly Ser Gly Ser Gly Ser Gly Ser
1 5 10

<210> SEQ ID NO 22
<211> LENGTH: 6
<212> TYPE: PRT
<213> ORGANISM: Artificial Sequence
<220> FEATURE:
<223> OTHER INFORMATION: Synthetic Construct

<400> SEQUENCE: 22

Gly Gly Ser Gly Gly Ser
1 5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Gly Gly Ser Gly Gly Ser Gly Gly Ser
1 5

<210> SEQ ID NO 24
<211> LENGTH: 12
<212> TYPE: PRT
<213> ORGANISM: Artificial Sequence
<220> FEATURE:
<223> OTHER INFORMATION: Synthetic Construct

<400> SEQUENCE: 24

Gly Gly Ser Gly Gly Ser Gly Gly Ser Gly Gly Ser
1 5 10

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Gly Gly Ser Gly Gly Gly Ser Gly
1 5

<210> SEQ ID NO 26
<211> LENGTH: 12
<212> TYPE: PRT
<213> ORGANISM: Artificial Sequence
<220> FEATURE:
<223> OTHER INFORMATION: Synthetic Construct

<400> SEQUENCE: 26

Gly Gly Ser Gly Gly Gly Ser Gly Gly Gly Ser Gly
1 5 10

<210> SEQ ID NO 27
<211> LENGTH: 15
<212> TYPE: PRT

<213> ORGANISM: Artificial Sequence
<220> FEATURE:
<223> OTHER INFORMATION: Synthetic Construct

<400> SEQUENCE: 27

Gly Gly Gly Gly Ser Gly Gly Gly Gly Ser Gly Gly Gly Gly Ser
1 5 10 15

<210> SEQ ID NO 28
<211> LENGTH: 20
<212> TYPE: PRT
<213> ORGANISM: Artificial Sequence
<220> FEATURE:
<223> OTHER INFORMATION: Synthetic Construct

<400> SEQUENCE: 28

Ser Gly Gly Gly Ser Gly Gly Gly Ser Gly Gly Gly Ser Gly Gly Gly
1 5 10 15

Ser Gly Gly Gly
20

<210> SEQ ID NO 29
<211> LENGTH: 8
<212> TYPE: PRT
<213> ORGANISM: Artificial Sequence
<220> FEATURE:
<223> OTHER INFORMATION: Synthetic Construct

<400> SEQUENCE: 29

Gly Gly Gly Gly Gly Gly Gly Gly
1 5

<210> SEQ ID NO 30
<211> LENGTH: 12
<212> TYPE: PRT
<213> ORGANISM: Artificial Sequence
<220> FEATURE:
<223> OTHER INFORMATION: Synthetic Construct

<400> SEQUENCE: 30

Gly Gly Gly Gly Gly Gly Gly Gly Gly Gly Gly Gly
1 5 10

<210> SEQ ID NO 31
<211> LENGTH: 16
<212> TYPE: PRT
<213> ORGANISM: Artificial Sequence
<220> FEATURE:
<223> OTHER INFORMATION: Synthetic Construct

<400> SEQUENCE: 31

Gly Gly Gly Gly Gly Gly Gly Gly Gly Gly Gly Gly Gly Gly Gly Gly
1 5 10 15

<210> SEQ ID NO 32
<211> LENGTH: 20
<212> TYPE: PRT
<213> ORGANISM: Artificial Sequence
<220> FEATURE:
<223> OTHER INFORMATION: Synthetic Construct

<400> SEQUENCE: 32

Gly Gly Gly Gly Gly Gly Gly Gly Gly Gly Gly Gly Gly Gly Gly Gly
1 5 10 15

Gly Gly Gly Gly
20

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct

<400> SEQUENCE: 33

Gly Gly Gly Gly Gly
1 5

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Gly Gly Gly Gly Gly Gly Gly Gly Gly Gly
1 5 10

<210> SEQ ID NO 35
<211> LENGTH: 15
<212> TYPE: PRT
<213> ORGANISM: Artificial Sequence
<220> FEATURE:
<223> OTHER INFORMATION: Synthetic Construct

<400> SEQUENCE: 35

Gly Gly Gly Gly Gly Gly Gly Gly Gly Gly Gly Gly Gly Gly Gly
1 5 10 15

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Gly Glu Asn Leu Tyr Phe Gln Ser Gly Gly
1 5 10

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct

<400> SEQUENCE: 37

Ser Ala Cys Tyr Cys Glu Leu Ser
1 5

<210> SEQ ID NO 38
<211> LENGTH: 5
<212> TYPE: PRT
<213> ORGANISM: Artificial Sequence
<220> FEATURE:
<223> OTHER INFORMATION: Synthetic Construct

<400> SEQUENCE: 38

Arg Ser Ile Ala Thr
1 5

<210> SEQ ID NO 39
<211> LENGTH: 17
<212> TYPE: PRT
<213> ORGANISM: Artificial Sequence
<220> FEATURE:
<223> OTHER INFORMATION: Synthetic Construct

<400> SEQUENCE: 39

Arg Pro Ala Cys Lys Ile Pro Asn Asp Leu Lys Gln Lys Val Met Asn
1 5 10 15

His

<210> SEQ ID NO 40
<211> LENGTH: 36
<212> TYPE: PRT
<213> ORGANISM: Artificial Sequence
<220> FEATURE:
<223> OTHER INFORMATION: Synthetic Construct

<400> SEQUENCE: 40

Gly Gly Ser Ala Gly Gly Ser Gly Ser Gly Ser Ser Gly Gly Ser Ser
1 5 10 15

Gly Ala Ser Gly Thr Gly Thr Ala Gly Gly Thr Gly Ser Gly Ser Gly
20 25 30

Thr Gly Ser Gly
35

<210> SEQ ID NO 41
<211> LENGTH: 17
<212> TYPE: PRT
<213> ORGANISM: Artificial Sequence
<220> FEATURE:
<223> OTHER INFORMATION: Synthetic Construct

<400> SEQUENCE: 41

Ala Ala Ala Asn Ser Ser Ile Asp Leu Ile Ser Val Pro Val Asp Ser
1 5 10 15

Arg

<210> SEQ ID NO 42
<211> LENGTH: 36
<212> TYPE: PRT
<213> ORGANISM: Artificial Sequence
<220> FEATURE:
<223> OTHER INFORMATION: Synthetic Construct

<400> SEQUENCE: 42

Gly Gly Ser Gly Gly Gly Ser Glu Gly Gly Gly Ser Glu Gly Gly Gly
1 5 10 15

Ser Glu Gly Gly Gly Ser Glu Gly Gly Gly Ser Glu Gly Gly Gly Ser
20 25 30

Gly Gly Gly Ser
35

<210> SEQ ID NO 43
<211> LENGTH: 669
<212> TYPE: PRT
<213> ORGANISM: Artificial Sequence
<220> FEATURE:
<223> OTHER INFORMATION: Synthetic Construct

<400> SEQUENCE: 43

Met Pro Leu Leu Leu Leu Leu Leu Leu Leu Pro Ser Pro Leu His Gly

-continued

```
1               5                   10                  15

Thr Gln Asn Lys Ala Leu Pro Glu Asn Val Lys Tyr Gly Ile Val Leu
            20                  25                  30

Asp Ala Gly Ser Ser His Thr Ser Leu Tyr Ile Tyr Lys Trp Pro Ala
        35                  40                  45

Glu Lys Glu Asn Asp Thr Gly Val Val His Gln Val Glu Glu Cys Arg
    50                  55                  60

Val Lys Gly Pro Gly Ile Ser Lys Phe Val Gln Lys Val Asn Glu Ile
65                  70                  75                  80

Gly Ile Tyr Leu Thr Asp Cys Met Glu Arg Ala Arg Glu Val Ile Pro
                85                  90                  95

Arg Ser Gln His Gln Glu Thr Pro Val Tyr Leu Gly Ala Thr Ala Gly
            100                 105                 110

Met Arg Leu Leu Arg Met Glu Ser Glu Glu Leu Ala Asp Arg Val Leu
        115                 120                 125

Asp Val Val Glu Arg Ser Leu Ser Asn Tyr Pro Phe Asp Phe Gln Gly
    130                 135                 140

Ala Arg Ile Ile Thr Gly Gln Glu Glu Gly Ala Tyr Gly Trp Ile Thr
145                 150                 155                 160

Ile Asn Tyr Leu Leu Gly Lys Phe Ser Gln Lys Thr Arg Trp Phe Ser
                165                 170                 175

Ile Val Pro Tyr Glu Thr Asn Asn Gln Glu Thr Phe Gly Ala Leu Asp
            180                 185                 190

Leu Gly Gly Ala Ser Thr Gln Val Thr Phe Val Pro Gln Asn Gln Thr
        195                 200                 205

Ile Glu Ser Pro Asp Asn Ala Leu Gln Phe Arg Leu Tyr Gly Lys Asp
    210                 215                 220

Tyr Asn Val Tyr Thr His Ser Phe Leu Cys Tyr Gly Lys Asp Gln Ala
225                 230                 235                 240

Leu Trp Gln Lys Leu Ala Lys Asp Ile Gln Val Ala Ser Asn Glu Ile
                245                 250                 255

Leu Arg Asp Pro Cys Phe His Pro Gly Tyr Lys Lys Val Val Asn Val
            260                 265                 270

Ser Asp Leu Tyr Lys Thr Pro Cys Thr Lys Arg Phe Glu Met Thr Leu
        275                 280                 285

Pro Phe Gln Gln Phe Glu Ile Gln Gly Ile Gly Asn Tyr Gln Gln Cys
    290                 295                 300

His Gln Ser Ile Leu Glu Leu Phe Asn Thr Ser Tyr Cys Pro Tyr Ser
305                 310                 315                 320

Gln Cys Ala Phe Asn Gly Ile Phe Leu Pro Pro Leu Gln Gly Asp Phe
                325                 330                 335

Gly Ala Phe Ser Ala Phe Tyr Phe Val Met Lys Phe Leu Asn Leu Thr
            340                 345                 350

Ser Glu Lys Val Ser Gln Glu Lys Val Thr Glu Met Met Lys Lys Phe
        355                 360                 365

Cys Ala Gln Pro Trp Glu Glu Ile Lys Thr Ser Tyr Ala Gly Val Lys
    370                 375                 380

Glu Lys Tyr Leu Ser Glu Tyr Cys Phe Ser Gly Thr Tyr Ile Leu Ser
385                 390                 395                 400

Leu Leu Leu Gln Gly Tyr His Phe Thr Ala Asp Ser Trp Glu His Ile
                405                 410                 415

His Phe Ile Gly Lys Ile Gln Gly Ser Asp Ala Gly Trp Thr Leu Gly
            420                 425                 430
```

```
Tyr Met Leu Asn Leu Thr Asn Met Ile Pro Ala Glu Gln Pro Leu Ser
        435                 440                 445

Thr Pro Leu Ser His Ser Thr Gly Gly Gly Gly Pro Ser Val Phe Leu
    450                 455                 460

Phe Pro Pro Lys Pro Lys Asp Thr Leu Met Ile Ser Arg Thr Pro Glu
465                 470                 475                 480

Val Thr Cys Val Val Val Asp Val Ser His Glu Asp Pro Glu Val Lys
                485                 490                 495

Phe Asn Trp Tyr Val Asp Gly Val Glu Val His Asn Ala Lys Thr Lys
            500                 505                 510

Pro Arg Glu Glu Gln Tyr Asn Ser Thr Tyr Arg Val Val Ser Val Leu
        515                 520                 525

Thr Val Leu His Gln Asp Trp Leu Asn Gly Lys Glu Tyr Lys Cys Lys
    530                 535                 540

Val Ser Asn Lys Ala Leu Pro Ala Pro Ile Glu Lys Thr Ile Ser Lys
545                 550                 555                 560

Ala Lys Gly Gln Pro Arg Glu Pro Gln Val Tyr Thr Leu Pro Pro Ser
                565                 570                 575

Arg Glu Glu Met Thr Lys Asn Gln Val Asn Leu Thr Cys Leu Val Lys
            580                 585                 590

Gly Phe Tyr Pro Ser Asp Ile Ala Val Glu Trp Glu Ser Asn Gly Gln
        595                 600                 605

Pro Glu Asn Asn Tyr Lys Thr Thr Pro Pro Val Leu Asp Ser Asp Gly
    610                 615                 620

Ser Phe Phe Leu Asn Ser Thr Leu Thr Val Asp Lys Ser Arg Trp Gln
625                 630                 635                 640

Gln Gly Asn Val Phe Ser Cys Ser Val Met His Glu Ala Leu His Asn
                645                 650                 655

His Tyr Thr Gln Lys Ser Leu Ser Leu Ser Pro Gly Lys
            660                 665


<210> SEQ ID NO 44
<211> LENGTH: 753
<212> TYPE: PRT
<213> ORGANISM: Artificial Sequence
<220> FEATURE:
<223> OTHER INFORMATION: Synthetic Construct

<400> SEQUENCE: 44

Met Pro Leu Leu Leu Leu Leu Leu Leu Leu Pro Ser Pro Leu His Gly
1               5                   10                  15

Trp Glu Leu Thr Ile Leu His Thr Asn Asp Val His Ser Arg Leu Glu
            20                  25                  30

Gln Thr Ser Glu Asp Ser Ser Lys Cys Val Asn Ala Ser Arg Cys Met
        35                  40                  45

Gly Gly Val Ala Arg Leu Phe Thr Lys Val Gln Gln Ile Arg Arg Ala
    50                  55                  60

Glu Pro Asn Val Leu Leu Leu Asp Ala Gly Asp Gln Tyr Gln Gly Thr
65                  70                  75                  80

Ile Trp Phe Thr Val Tyr Lys Gly Ala Glu Val Ala His Phe Met Asn
                85                  90                  95

Ala Leu Arg Tyr Asp Ala Met Ala Leu Gly Asn His Glu Phe Asp Asn
            100                 105                 110

Gly Val Glu Gly Leu Ile Glu Pro Leu Leu Lys Glu Ala Lys Phe Pro
        115                 120                 125
```

-continued

```
Ile Leu Ser Ala Asn Ile Lys Ala Lys Gly Pro Leu Ala Ser Gln Ile
    130                 135                 140

Ser Gly Leu Tyr Leu Pro Tyr Lys Val Leu Pro Val Gly Asp Glu Val
145                 150                 155                 160

Val Gly Ile Val Gly Tyr Thr Ser Lys Glu Thr Pro Phe Leu Ser Asn
                165                 170                 175

Pro Gly Thr Asn Leu Val Phe Glu Asp Glu Ile Thr Ala Leu Gln Pro
            180                 185                 190

Glu Val Asp Lys Leu Lys Thr Leu Asn Val Asn Lys Ile Ile Ala Leu
        195                 200                 205

Gly His Ser Gly Phe Glu Met Asp Lys Leu Ile Ala Gln Lys Val Arg
    210                 215                 220

Gly Val Asp Val Val Val Gly Gly His Ser Asn Thr Phe Leu Tyr Thr
225                 230                 235                 240

Gly Asn Pro Pro Ser Lys Glu Val Pro Ala Gly Lys Tyr Pro Phe Ile
                245                 250                 255

Val Thr Ser Asp Asp Gly Arg Lys Val Pro Val Val Gln Ala Tyr Ala
            260                 265                 270

Phe Gly Lys Tyr Leu Gly Tyr Leu Lys Ile Glu Phe Asp Glu Arg Gly
        275                 280                 285

Asn Val Ile Ser Ser His Gly Asn Pro Ile Leu Leu Asn Ser Ser Ile
    290                 295                 300

Pro Glu Asp Pro Ser Ile Lys Ala Asp Ile Asn Lys Trp Arg Ile Lys
305                 310                 315                 320

Leu Asp Asn Tyr Ser Thr Gln Glu Leu Gly Lys Thr Ile Val Tyr Leu
                325                 330                 335

Asp Gly Ser Ser Gln Ser Cys Arg Phe Arg Glu Cys Asn Met Gly Asn
            340                 345                 350

Leu Ile Cys Asp Ala Met Ile Asn Asn Asn Leu Arg His Ala Asp Glu
        355                 360                 365

Thr Phe Trp Asn His Val Ser Met Cys Ile Leu Asn Gly Gly Gly Ile
    370                 375                 380

Arg Ser Pro Ile Asp Glu Arg Asn Asn Gly Thr Ile Thr Trp Glu Asn
385                 390                 395                 400

Leu Ala Ala Val Leu Pro Phe Gly Gly Thr Phe Asp Leu Val Gln Leu
                405                 410                 415

Lys Gly Ser Thr Leu Lys Lys Ala Phe Glu His Ser Val His Arg Tyr
            420                 425                 430

Gly Gln Ser Thr Gly Glu Phe Leu Gln Val Gly Gly Ile His Val Val
        435                 440                 445

Tyr Asp Leu Ser Arg Lys Pro Gly Asp Arg Val Val Lys Leu Asp Val
    450                 455                 460

Leu Cys Thr Lys Cys Arg Val Pro Ser Tyr Asp Pro Leu Lys Met Asp
465                 470                 475                 480

Glu Val Tyr Lys Val Ile Leu Pro Asn Phe Leu Ala Asn Gly Gly Asp
                485                 490                 495

Gly Phe Gln Met Ile Lys Asp Glu Leu Leu Arg His Asp Ser Gly Asp
            500                 505                 510

Gln Asp Ile Asn Val Val Ser Thr Tyr Ile Ser Lys Met Lys Val Ile
        515                 520                 525

Tyr Pro Ala Val Glu Gly Arg Ile Lys Phe Ser Gly Gly Gly Gly Pro
    530                 535                 540
```

Ser Val Phe Leu Phe Pro Pro Lys Pro Lys Asp Thr Leu Met Ile Ser
545 550 555 560

Arg Thr Pro Glu Val Thr Cys Val Val Val Asp Val Ser His Glu Asp
565 570 575

Pro Glu Val Lys Phe Asn Trp Tyr Val Asp Gly Val Glu Val His Asn
580 585 590

Ala Lys Thr Lys Pro Arg Glu Glu Gln Tyr Asn Ser Thr Tyr Arg Val
595 600 605

Val Ser Val Leu Thr Val Leu His Gln Asp Trp Leu Asn Gly Lys Glu
610 615 620

Tyr Lys Cys Lys Val Ser Asn Lys Ala Leu Pro Ala Pro Ile Glu Lys
625 630 635 640

Thr Ile Ser Lys Ala Lys Gly Gln Pro Arg Glu Pro Gln Val Tyr Thr
645 650 655

Leu Pro Pro Ser Arg Glu Glu Met Thr Lys Asn Gln Val Asn Leu Thr
660 665 670

Cys Leu Val Lys Gly Phe Tyr Pro Ser Asp Ile Ala Val Glu Trp Glu
675 680 685

Ser Asn Gly Gln Pro Glu Asn Asn Tyr Lys Thr Thr Pro Pro Val Leu
690 695 700

Asp Ser Asp Gly Ser Phe Phe Leu Asn Ser Thr Leu Thr Val Asp Lys
705 710 715 720

Ser Arg Trp Gln Gln Gly Asn Val Phe Ser Cys Ser Val Met His Glu
725 730 735

Ala Leu His Asn His Tyr Thr Gln Lys Ser Leu Ser Leu Ser Pro Gly
740 745 750

Lys

<210> SEQ ID NO 45
<211> LENGTH: 713
<212> TYPE: PRT
<213> ORGANISM: Artificial Sequence
<220> FEATURE:
<223> OTHER INFORMATION: Synthetic Construct

<400> SEQUENCE: 45

Met Pro Leu Leu Leu Leu Leu Leu Leu Leu Pro Ser Pro Leu His Gly
1 5 10 15

Ile Ile Pro Val Glu Glu Glu Asn Pro Asp Phe Trp Asn Arg Gln Ala
20 25 30

Ala Glu Ala Leu Gly Ala Ala Lys Lys Leu Gln Pro Ala Gln Thr Ala
35 40 45

Ala Lys Asn Leu Ile Ile Phe Leu Gly Asp Gly Met Gly Val Ser Thr
50 55 60

Val Thr Ala Ala Arg Ile Leu Lys Gly Gln Lys Lys Asp Lys Leu Gly
65 70 75 80

Pro Glu Thr Phe Leu Ala Met Asp Arg Phe Pro Tyr Val Ala Leu Ser
85 90 95

Lys Thr Tyr Ser Val Asp Lys His Val Pro Asp Ser Gly Ala Thr Ala
100 105 110

Thr Ala Tyr Leu Cys Gly Val Lys Gly Asn Phe Gln Thr Ile Gly Leu
115 120 125

Ser Ala Ala Ala Arg Phe Asn Gln Cys Asn Thr Thr Arg Gly Asn Glu
130 135 140

Val Ile Ser Val Met Asn Arg Ala Lys Lys Ala Gly Lys Ser Val Gly

-continued

```
145                 150                 155                 160

Val Val Thr Thr Thr Arg Val Gln His Ala Ser Pro Ala Gly Thr Tyr
                165                 170                 175

Ala His Thr Val Asn Arg Asn Trp Tyr Ser Asp Ala Asp Val Pro Ala
            180                 185                 190

Ser Ala Arg Gln Glu Gly Cys Gln Asp Ile Ala Thr Gln Leu Ile Ser
        195                 200                 205

Asn Met Asp Ile Asp Val Ile Leu Gly Gly Gly Arg Lys Tyr Met Phe
    210                 215                 220

Pro Met Gly Thr Pro Asp Pro Glu Tyr Pro Asp Asp Tyr Ser Gln Gly
225                 230                 235                 240

Gly Thr Arg Leu Asp Gly Lys Asn Leu Val Gln Glu Trp Leu Ala Lys
                245                 250                 255

His Gln Gly Ala Arg Tyr Val Trp Asn Arg Thr Glu Leu Leu Gln Ala
            260                 265                 270

Ser Leu Asp Pro Ser Val Thr His Leu Met Gly Leu Phe Glu Pro Gly
        275                 280                 285

Asp Met Lys Tyr Glu Ile His Arg Asp Ser Thr Leu Asp Pro Ser Leu
    290                 295                 300

Met Glu Met Thr Glu Ala Ala Leu Leu Leu Leu Ser Arg Asn Pro Arg
305                 310                 315                 320

Gly Phe Phe Leu Phe Val Glu Gly Gly Arg Ile Asp His Gly His His
                325                 330                 335

Glu Ser Arg Ala Tyr Arg Ala Leu Thr Glu Thr Ile Met Phe Asp Asp
            340                 345                 350

Ala Ile Glu Arg Ala Gly Gln Leu Thr Ser Glu Glu Asp Thr Leu Ser
        355                 360                 365

Leu Val Thr Ala Asp His Ser His Leu Phe Ser Phe Gly Gly Tyr Pro
    370                 375                 380

Leu Arg Gly Ser Ser Ile Phe Gly Leu Ala Pro Gly Lys Ala Arg Asp
385                 390                 395                 400

Arg Lys Ala Tyr Thr Val Leu Leu Tyr Gly Asn Gly Pro Gly Tyr Val
                405                 410                 415

Leu Lys Asp Gly Ala Arg Pro Asp Val Thr Glu Ser Glu Ser Gly Ser
            420                 425                 430

Pro Glu Tyr Arg Gln Gln Ser Ala Val Pro Leu Asp Gly Glu Thr His
        435                 440                 445

Ala Gly Glu Asp Val Ala Val Phe Ala Arg Gly Pro Gln Ala His Leu
    450                 455                 460

Val His Gly Val Gln Glu Gln Thr Phe Ile Ala His Val Met Ala Phe
465                 470                 475                 480

Ala Ala Cys Leu Glu Pro Tyr Thr Ala Cys Asp Leu Ala Pro Arg Ala
                485                 490                 495

Gly Thr Thr Gly Gly Gly Gly Pro Ser Val Phe Leu Phe Pro Pro Lys
            500                 505                 510

Pro Lys Asp Thr Leu Met Ile Ser Arg Thr Pro Glu Val Thr Cys Val
        515                 520                 525

Val Val Asp Val Ser His Glu Asp Pro Glu Val Lys Phe Asn Trp Tyr
    530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
                565                 570                 575
```

Gln Asp Trp Leu Asn Gly Lys Glu Tyr Lys Cys Lys Val Ser Asn Lys
580 585 590

Ala Leu Pro Ala Pro Ile Glu Lys Thr Ile Ser Lys Ala Lys Gly Gln
595 600 605

Pro Arg Glu Pro Gln Val Tyr Thr Leu Pro Pro Ser Arg Glu Glu Met
610 615 620

Thr Lys Asn Gln Val Asn Leu Thr Cys Leu Val Lys Gly Phe Tyr Pro
625 630 635 640

Ser Asp Ile Ala Val Glu Trp Glu Ser Asn Gly Gln Pro Glu Asn Asn
645 650 655

Tyr Lys Thr Thr Pro Pro Val Leu Asp Ser Asp Gly Ser Phe Phe Leu
660 665 670

Asn Ser Thr Leu Thr Val Asp Lys Ser Arg Trp Gln Gln Gly Asn Val
675 680 685

Phe Ser Cys Ser Val Met His Glu Ala Leu His Asn His Tyr Thr Gln
690 695 700

Lys Ser Leu Ser Leu Ser Pro Gly Lys
705 710

<210> SEQ ID NO 46
<211> LENGTH: 584
<212> TYPE: PRT
<213> ORGANISM: Artificial Sequence
<220> FEATURE:
<223> OTHER INFORMATION: Synthetic Construct

<400> SEQUENCE: 46

Met Pro Leu Leu Leu Leu Leu Leu Leu Leu Pro Ser Pro Leu His Gly
1 5 10 15

Lys Glu Leu Lys Phe Val Thr Leu Val Phe Arg His Gly Asp Arg Ser
20 25 30

Pro Ile Asp Thr Phe Pro Thr Asp Pro Ile Lys Glu Ser Ser Trp Pro
35 40 45

Gln Gly Phe Gly Gln Leu Thr Gln Leu Gly Met Glu Gln His Tyr Glu
50 55 60

Leu Gly Glu Tyr Ile Arg Lys Arg Tyr Arg Lys Phe Leu Asn Glu Ser
65 70 75 80

Tyr Lys His Glu Gln Val Tyr Ile Arg Ser Thr Asp Val Asp Arg Thr
85 90 95

Leu Met Ser Ala Met Thr Asn Leu Ala Ala Leu Phe Pro Pro Glu Gly
100 105 110

Val Ser Ile Trp Asn Pro Ile Leu Leu Trp Gln Pro Ile Pro Val His
115 120 125

Thr Val Pro Leu Ser Glu Asp Gln Leu Leu Tyr Leu Pro Phe Arg Asn
130 135 140

Cys Pro Arg Phe Gln Glu Leu Glu Ser Glu Thr Leu Lys Ser Glu Glu
145 150 155 160

Phe Gln Lys Arg Leu His Pro Tyr Lys Asp Phe Ile Ala Thr Leu Gly
165 170 175

Lys Leu Ser Gly Leu His Gly Gln Asp Leu Phe Gly Ile Trp Ser Lys
180 185 190

Val Tyr Asp Pro Leu Tyr Cys Glu Ser Val His Asn Phe Thr Leu Pro
195 200 205

Ser Trp Ala Thr Glu Asp Thr Met Thr Lys Leu Arg Glu Leu Ser Glu
210 215 220

-continued

```
Leu Ser Leu Leu Ser Leu Tyr Gly Ile His Lys Gln Lys Glu Lys Ser
225                 230                 235                 240

Arg Leu Gln Gly Gly Val Leu Val Asn Glu Ile Leu Asn His Met Lys
                245                 250                 255

Arg Ala Thr Gln Ile Pro Ser Tyr Lys Lys Leu Ile Met Tyr Ser Ala
            260                 265                 270

His Asp Thr Thr Val Ser Gly Leu Gln Met Ala Leu Asp Val Tyr Asn
        275                 280                 285

Gly Leu Leu Pro Pro Tyr Ala Ser Cys His Leu Thr Glu Leu Tyr Phe
    290                 295                 300

Glu Lys Gly Glu Tyr Phe Val Glu Met Tyr Tyr Arg Asn Glu Thr Gln
305                 310                 315                 320

His Glu Pro Tyr Pro Leu Met Leu Pro Gly Cys Ser Pro Ser Cys Pro
                325                 330                 335

Leu Glu Arg Phe Ala Glu Leu Val Gly Pro Val Ile Pro Gln Asp Trp
            340                 345                 350

Ser Thr Glu Cys Met Thr Thr Asn Ser His Gln Gly Thr Glu Asp Ser
        355                 360                 365

Thr Asp Gly Gly Gly Gly Pro Ser Val Phe Leu Phe Pro Pro Lys Pro
    370                 375                 380

Lys Asp Thr Leu Met Ile Ser Arg Thr Pro Glu Val Thr Cys Val Val
385                 390                 395                 400

Val Asp Val Ser His Glu Asp Pro Glu Val Lys Phe Asn Trp Tyr Val
                405                 410                 415

Asp Gly Val Glu Val His Asn Ala Lys Thr Lys Pro Arg Glu Glu Gln
            420                 425                 430

Tyr Asn Ser Thr Tyr Arg Val Val Ser Val Leu Thr Val Leu His Gln
        435                 440                 445

Asp Trp Leu Asn Gly Lys Glu Tyr Lys Cys Lys Val Ser Asn Lys Ala
    450                 455                 460

Leu Pro Ala Pro Ile Glu Lys Thr Ile Ser Lys Ala Lys Gly Gln Pro
465                 470                 475                 480

Arg Glu Pro Gln Val Tyr Thr Leu Pro Pro Ser Arg Glu Glu Met Thr
                485                 490                 495

Lys Asn Gln Val Asn Leu Thr Cys Leu Val Lys Gly Phe Tyr Pro Ser
            500                 505                 510

Asp Ile Ala Val Glu Trp Glu Ser Asn Gly Gln Pro Glu Asn Asn Tyr
        515                 520                 525

Lys Thr Thr Pro Pro Val Leu Asp Ser Asp Gly Ser Phe Phe Leu Asn
    530                 535                 540

Ser Thr Leu Thr Val Asp Lys Ser Arg Trp Gln Gln Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Pro Gly Lys
            580
```

COMPOSITIONS AND METHODS FOR DECREASING INFLAMMATION

STATEMENT AS TO FEDERALLY FUNDED RESEARCH

10 This invention was made with government support under Grant Nos. CA221702, CA164970, and HL094400 awarded by the National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Aug. 13, 2021, is named 01948-281WO2_Sequence_Listing_08_13_21_ST25.txt and is 95,537 bytes in size.

BACKGROUND OF THE INVENTION

Damaged cells, activated immune cells, platelets and stressed cells release large amounts of adenosine 5'-triphosphate (ATP) and adenosine 5' diphosphate (ADP) during tissue injury, inflammation, hypoxia, apoptosis, vascular thrombosis and mechanical perturbation. Besides passively via ruptured cell membranes, nucleotide release can be done actively through exocytosis of intracellular vesicles or transport by membrane-bound channels or transporters. These extracellular nucleotides serve as potent signaling molecules and stimulate various ligand-gated ion channel P2X receptors (P2XR) and G-protein-coupled P2Y receptors (P2YR) to drive inflammation, platelet activation, clotting, immune response regulation, tissue blood flow control, and neuronal signaling. This form of purinergic signaling is also crucial to the activation of inflammasomes, via P2X7R, with subsequent proinflammatory cytokine release in response to damage-associated molecular patterns and pathogen-associated molecular patterns. To prevent overstimulation or desensitization of P2XRs and P2YRs, ATP and ADP are quickly hydrolyzed to produce adenosine 5' monophosphate (AMP), and eventually nucleoside adenosine.

The conversion from pro-inflammatory ATP or ADP to anti-inflammatory adenosine is regulated by the spatial and temporal expression patterns, enzymatic activity variation, enzyme concentration, exposure duration, and localization of ectonucleotidases, a group of enzymes responsible for hydrolysis of extracellular nucleotides under varied biological conditions. Due to the complex regulatory network of these enzymes, impairment of nucleotide hydrolysis can disrupt the desired equilibrium of ATP, ADP, and AMP during inflammatory responses. Accordingly, new compositions and methods are needed to better regulate the hydrolysis of ATP and ADP to AMP in order to reduce inflammation.

SUMMARY OF THE INVENTION

The present invention features bifunctional enzymes that are engineered to hydrolyze nucleotide triphosphates (e.g., ATP) completely to form nucleosides (e.g., adenosine), through the fusion of the ectodomains (ECD) of an ecto-nucleoside triphosphate diphosphohydrolase (E-NTPDase)/CD39 family member and an ectonucleotidase (NMPase), such as an ecto-5' nucleotidase (eN)/CD73, an alkaline phosphatase (AP), or an acid phosphatase (AP). Described herein are polypeptides that include an E-NTPDase CD39 family member with an NMPase (e.g., eN, ALP, or AP) and methods of use thereof, e.g., for decreasing inflammation.

In one aspect, the invention features a polypeptide that includes an E-NTPDase (e.g., NTPDase1, NTPDase2, NTPDase3, NTPDase4, NTPDase5, NTPDase6, NTPDase7, and NTPDase8, or a variant thereof, as described herein) and an NMPase, such as eN, ALP, or AP (e.g., a fusion protein containing the ECD of an E-NTPDase fused to the ECD of an eN, in either order). In particular embodiments, the ECD of the E-NTPDase corresponds to the extracellular catalytic domain. The extracellular catalytic domain may be a region that shares homology or sequence identity to the extracellular catalytic domain of CD39, which is set forth in SEQ ID NO: 1. Homology or sequence identity can be determined using standard sequence alignment or other homology-determining tools known in the art. The polypeptide may have a structure from N-terminus to C-terminus of A-(E-NTPDase)-L-eN-B; or A-eN-L-(E-NTPDase)-B; wherein A is absent or is an amino acid sequence of one or more amino acids; B is absent or is an amino acid sequence of one or more amino acids; and L is absent or is a linker, e.g., a chemical linker or a polypeptide linker of one or more amino acids.

The polypeptide may have a structure from N-terminus to C-terminus of A-(E-NTPDase)-L-ALP-B; or A-ALP-L-(E-NTPDase)-B; wherein A is absent or is an amino acid sequence of one or more amino acids; B is absent or is an amino acid sequence of one or more amino acids; and L is absent or is a linker, e.g., a chemical linker or a polypeptide linker of one or more amino acids.

The polypeptide may have a structure from N-terminus to C-terminus of A-(E-NTPDase)-L-AP-B; or A-AP-L-(E-NTPDase)-B; wherein A is absent or is an amino acid sequence of one or more amino acids; B is absent or is an amino acid sequence of one or more amino acids; and L is absent or is a linker, e.g., a chemical linker or a polypeptide linker of one or more amino acids.

The E-NTPDase may be ectonucleoside triphosphate diphosphohydrolase-1 (NTPDase1; CD39) or a biologically active truncation, mutant, or derivative thereof. The CD39 may have at least 80% (e.g., at least 85%, 90%, 95%, 97%, or 99%) sequence identity to SEQ ID NO: 1. The CD39 may include or consist of the sequence of SEQ ID NO: 1.

The eN may be ecto-5'-nucleotidase (CD73) or a biologically active truncation, mutant, or derivative thereof. The CD73 may have at least 80% (e.g., at least 85%, 90%, 95%, 97%, or 99%) sequence identity to SEQ ID NO: 2. The CD73 may include or consist of the sequence of SEQ ID NO: 2.

The ALP may be intestinal alkaline phosphatase, e.g., human intestinal alkaline phosphatase. The AP may be human prostatic acid phosphatase.

In some embodiments, A, B, and/or L includes a fragment crystallizable (Fc) domain. The Fc domain may be an IgG1 Fc domain. The Fc domain may have at least 80% (e.g., at least 85%, 90%, 95%, 97%, or 99%) sequence identity to SEQ ID NO: 5. The Fc domain may include or consist of the sequence of SEQ ID NO: 5.

In some embodiments, A, B, and/or L include or consist of one or more glycines, serines, or a combination thereof (e.g., 2, 3, 4, 5, 6, 7, 8, 9, 10, 11, 12, 13, 14, 15, 16, 17, 18, 19, or 20 or more glycines, serines, or a combination thereof). For example, A, B, and/or L may include a polyglycine linker. The polyglycine linker may include or consist of the sequence of GGGG (SEQ ID NO: 3). The linker, L, may also be selected from any of a number of known polypeptide linkers with 1-20 amino acids or more in length.

The polypeptides described herein may have a structure from N-terminus to C-terminus of A-CD39-L-CD73-B; or A-CD73-L-CD39-B; wherein A is absent or is an amino acid sequence of one or more amino acids; B is absent or is an amino acid sequence of one or more amino acids; and L is absent or is a linker of, e.g., one or more amino acids.

A, B, and/or L may include a polyglycine linker and an Fc domain. A, B, and/or L may include GGGG (SEQ ID NO: 3)-Fc and/or GGGG (SEQ ID NO: 3)-Fc-GGGG (SEQ ID NO: 3). For example, A, B, and/or L may have at least 80% (e.g., at least 85%, 90%, 95%, 97%, or 99%) sequence identity to SEQ ID NOs: 6 or 7. A, B, and/or L may include or consist of the sequence of SEQ ID NOs: 6 or 7. A, B, and/or L may have at least 80% (e.g., at least 85%, 90%, 95%, 97%, or 99%) sequence identity to SEQ ID NO: 4. For example, A may include or consist of the sequence of SEQ ID NO: 4. L may include or consist of GGGG (SEQ ID NO: 3), and B may include GGGG (SEQ ID NO: 3)-Fc.

In some embodiments, the polypeptide has at least 80% (e.g., at least 80%, 85%, 90%, 95%, 97%, or 99%) sequence identity to SEQ ID NOs: 8 or 9. For example, the polypeptide may include or consist of the sequence of SEQ ID NOs: 8 or 9 (i.e., A-CD39-L-CD73-Fc (construct 2 in FIG. 1A); or A-CD73-L-CD39-Fc (construct 4 in FIG. 1A)).

In some embodiments, L includes GGGG (SEQ ID NO: 3)-Fc-GGGG (SEQ ID NO: 3). The polypeptide may have at least 80% (e.g., at least 85%, 90%, 95%, 97%, or 99%) sequence identity to SEQ ID NOs: 10 or 11. For example, the polypeptide may include or consist of the sequence of SEQ ID NOs: 10 or 11 (i.e., A-CD39-Fc-CD73-B (construct 1 in FIG. 1A); or A-CD73-Fc-CD39-B (construct 3 in FIG. 1A)).

Another aspect of the disclosure features a polynucleotide encoding the polypeptide of any of the above aspects. Also featured are a vector that includes the polynucleotide and a cell that includes the polynucleotide or the vector.

Yet another aspect of the disclosure features a method of producing a polypeptide as described herein. The method includes providing a cell transformed with a polynucleotide encoding the polypeptide or a vector that includes the polynucleotide; culturing the transformed cell under conditions for expressing the polynucleotide, wherein the culturing results in expression of the polypeptide. The method may further include purifying and/or isolating the polypeptide.

In another aspect, the invention features a method of hydrolyzing a nucleotide triphosphate (NTP) or nucleotide diphosphate (NDP) to a nucleoside. The method includes providing the polypeptide of any of the above aspects and the NTP or NDP and allowing the polypeptide to hydrolyze the NTP or NDP to a nucleoside. The NTP may be adenosine 5' triphosphate (ATP). The NDP may be adenosine 5' diphosphate (ADP). The nucleoside may be adenosine. The method may include providing a polynucleotide encoding the polypeptide, a vector containing the polynucleotide, or a cell containing the polynucleotide or vector (or a composition containing any one or more of these components) rather than the polypeptide.

In another aspect, the invention features a method of inhibiting platelet aggregation (e.g., in a subject, such as a human, in need thereof) by providing the polypeptide of any one of any of the above aspects, or a composition containing the same, and allowing the polypeptide to hydrolyze ATP and ADP to adenosine. The method may include providing a polynucleotide encoding the polypeptide, a vector containing the polynucleotide, or a cell containing the polynucleotide or vector (or a composition containing any one or more of these components) rather than the polypeptide. The subject may be at risk of forming a blood clot, e.g., a pulmonary embolism.

In another aspect, the invention features a method of decreasing (e.g., by 1%, 2%, 3%, 4%, 5%, 10%, 20%, 30%, 40%, 50%, 60%, 70%, 80%, 90%, 95%, 97, 99%, or more) inflammation (e.g., as measured by a blood test, e.g., by using a blood test for C-reactive protein (hs-CRP) in a subject (e.g., a human) by providing the polypeptide of any of the above aspects and allowing the polypeptide to hydrolyze ATP and ADP to adenosine. The method may include providing a polynucleotide encoding the polypeptide, a vector containing the polynucleotide, or a cell containing the polynucleotide or vector (or a composition containing any one or more of these components) rather than the polypeptide.

In another aspect, the invention features a method of treating a disease characterized by high levels of ATP and/or tissue damage, such as an acute inflammatory disease or cancer, by providing the polypeptide of any one of any of the above aspects, or a composition containing the same, thereby hydrolyzing ATP and ADP to adenosine in the subject. The disease may be selected from a cardiovascular or cerebrovascular illness, such as an illness associated with or linked to vascular endothelial and platelet activation with thrombosis, ischemia reperfusion injury, transplantation graft preservation and reperfusion, reperfusion injury to native organs, such as the heart, brain, liver, and gut, unstable angina and myocardial infarction, stroke, pulmonary embolism, deep vein thrombosis (DVT), acute surgical and nonsurgical trauma, a pulmonary illness (e.g., acute respiratory distress syndrome (ARDS) or a pulmonary illness caused by, e.g., lung injury resulting from trauma, a surgical procedure, an infection, pulmonary embolism, asthma, primary pulmonary hypertension, and pulmonary fibrosis), a neurodegenerative disease, multiple sclerosis, a rheumatological or autoimmune disease (e.g., acute tophaceous gout, seropositive rheumatoid arthritis, juvenile rheumatoid arthritis, psoriasis, lupus, and dermatomyositis), a gastrointestinal or liver disease (e.g., inflammatory bowel disease, celiac disease, *Clostridium difficile* and pseudomembranous colitis, mesenteric ischemia, fatty liver disorder and non-alcoholic steatohepatitis, acute toxic liver injury as with acetaminophen and mushroom poisoning, acute viral hepatitis, fulminant liver failure, and acute renal failure), septicemia and end-organ failure with purine starvation, COVID-19, acute diabetic ketoacidosis and metabolic perturbation, and pregnancy conditions, such as preeclampsia, toxemia, and acute fatty liver of pregnancy. The method can promote a decrease of inflammation (e.g., by 1%, 2%, 3%, 4%, 5%, 10%, 20%, 30%, 40%, 50%, 60%, 70%, 80%, 90%, 95%, 97, 99%, or more, e.g., as relative to an untreated subject), e.g., as measured by a blood test, e.g., via a blood test for C-reactive protein (hs-CRP) in the subject (e.g., a human). The method may include providing a polynucleotide encoding the polypeptide, a vector containing the polynucleotide, or a cell containing the polynucleotide or vector (or a composition containing any one or more of these components) rather than the polypeptide.

In some embodiments of the methods described herein, the method reduces (e.g., by 1%, 2%, 3%, 4%, 5%, 10%, 20%, 30%, 40%, 50%, 60%, 70%, 80%, 90%, 95%, 97, 99%, or more) blood pressure (e.g., as measured by diastolic and/or systolic pressure or ambulatory blood pressure monitoring (ABPM)) in the subject (e.g., a human). The method may be used to reduce vascular thrombosis and/or mechanical perturbation. The method may be used to reduce ischemia. The method may be used to treat a cancer.

In some embodiments, the methods described herein may be used to reduce inflammation in a tissue injury (e.g., injury to the epidermis, arm, leg, torso, head, foot, hand, finger), e.g., as measured by a blood test for hs-CRP or a volume of swelling in the subject.

The method may be used to reduce (e.g., by 1%, 2%, 3%, 4%, 5%, 10%, 20%, 30%, 40%, 50%, 60%, 70%, 80%, 90%, 95%, 97, 99%, or more) hypoxia, e.g., as measured using pulse oximetry.

The method may be used to reduce (e.g., by 1%, 2%, 3%, 4%, 5%, 10%, 20%, 30%, 40%, 50%, 60%, 70%, 80%, 90%, 95%, 97, 99%, or more) apoptosis, e.g., as determined via flow cytometry or externalization of phosphatidylserine on the plasma membrane using fluorescent-tagged annexin V.

In another aspect, the invention features a pharmaceutical composition that includes, the polypeptide, polynucleotide, vector, or cell of any of the above embodiments and a pharmaceutically acceptable carrier.

In another aspect, featured is a kit that includes the pharmaceutical composition and instructions for use thereof. The instructions may be used to instruct a user to perform a method as described herein.

Definitions

As used herein, the term "about" refers to a value that is 10% above or below the value being described.

As used herein, the terms "conservative mutation," "conservative substitution," "conservative amino acid substitution," and the like refer to a substitution of one or more amino acids for one or more different amino acids that exhibit similar physicochemical properties, such as polarity, electrostatic charge, and steric volume. These properties are summarized for each of the twenty naturally occurring amino acids in Table 1 below.

TABLE 1

Representative physicochemical properties of naturally occurring amino acids

| Amino Acid | 3 Letter Code | 1 Letter Code | Side-chain Polarity | Electrostatic character at physiological pH (7.4) | Steric Volume† |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | nonpolar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

†based on volume in $A^3$: 50-100 is small, 100-150 is intermediate, 150-200 is large, and >200 is bulky From this table it is appreciated that the conservative amino acid families include (i) G, A, V, L and I; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, the terms "ectonucleoside triphosphate diphosphohydrolase," "E-NTPDase," and ("NTPDase") refer to enzymes that catalyze the hydrolysis of γ- and β-phosphate residues of triphospho- and diphosphonucleosides to the monophosphonucleoside derivative. Examples of E-NTPDases include (alternative names in parentheses), e.g., NTPDase1 (CD39, ATPDase, ecto-apyrase), NTPDase2 (CD39L1, ecto-ATPase), NTPDase3 (CD39L3, HB6), NTPDase4 (UDPase, LALP70), NTPDase5 (CD39L4, ER-UDPase, PCPH), NTPDase6 (CD39L2), NTPDase7 (LALP1), and NTPDase8 (liver canalicular ecto-ATPase, hATPDase). The genes encoding human NTPDase1-NTPDase8 (UniProt P49961, Q9Y5L3, 075355, Q9Y227, 075356, 075354, Q9NQZ7, Q5MY95) are ENTPD1-ENTPD8, respectively (GenBank accession numbers U87697, AF144748, AF034840, AF016032, AF039918, AY327581, AF2692655, and AY430414). The genes encoding murine NTPDase1-NTPDase8 (UniProt P55772, 055026, Q8BFW6, Q9DBT4, Q9WUZ9, Q3UOP5, Q3TCT4, Q8K0L2) are Entpd1-Entpd8, respectively (GenBank accession numbers NM_009848, AY376711, AY376710, NM_026174, AJ238636, NM_172117, AF2888221, and AY36442). The term E-NTPDase includes all biologically active fragments, truncations, mutants, variants, substitutions, or derivatives thereof, e.g., of any of the foregoing protein or gene sequences. The term E-NTPDase also includes homologs from other species, such as rat, pig, chicken, bovine, and the like. Other sequences would be readily apparent to the skilled artisan, e.g., using publicly available databases known in the art. E-NTPDases are described, e.g., in Robson et al. (*Pur. Sign.* 2:409-430, 2006), which is hereby incorporated by reference in its entirety.

One example of an E-NTPDase is ectonucleoside triphosphate diphosphohydrolase-1 (also known as NTPDasel and CD39). CD39 hydrolyzes nucleoside triphosphates and disphosphates, such as ATP, UTP, ADP, and UDP to their monophosphate form. CD39 is multi-pass transmembrane domain and contains an extracellular catalytic domain. Full-length human CD39 has the following amino acid sequence (UniProt P49961):

(SEQ ID NO: 12)

```
MEDTKESNVKTFCSKNILAILGFSSIIAVIALLAVGLTQNKALPENVKYG
IVLDAGSSHTSLYIYKWPAEKENDTGVVHQVEECRVKGPGISKFVQKVNE
IGIYLTDCMERAREVIPRSQHQETPVYLGATAGMRLLRMESEELADRVLD
VVERSLSNYPFDFQGARIITGQEEGAYGWITINYLLGKFSQKTRWFSIVP
YETNNQETFGALDLGGASTQVTFVPQNQTIESPDNALQFRLYGKDYNVYT
HSFLCYGKDQALWQKLAKDIQVASNEILRDPCFHPGYKKVVNVSDLYKTP
CTKRFEMTLPFQQFEIQGIGNYQQCHQSILELFNTSYCPYSQCAFNGIFL
PPLQGDFGAFSAFYFVMKFLNLTSEKVSQEKVTEMMKKFCAQPWEEIKTS
YAGVKEKYLSEYCFSGTYILSLLLQGYHFTADSWEHIHFIGKIQGSDAGW
TLGYMLNLINMIPAEQPLSTPLSHSTYVFLMVLFSLVLFTVAIIGLLIFH
KPSYFWKDMV
```

CD39 encompasses all biologically active fragments, truncations, mutants, variants, substitutions, or derivatives thereof. An exemplary CD39 fragment is the polypeptide of SEQ ID NO: 1, which corresponds to the extracellular catalytic domain. CD39 includes all polypeptides having at least 50%, 60%, 70%, 80%, 85%, 90%, 95%, 97%, 99%, or 100% sequence identity to SEQ ID NO: 12 or to SEQ ID NO: 1. The term CD39 also includes homologs from other species, such as mouse, rat, pig, chicken, bovine, and the like (see, e.g., UniProt sequences P55772, P9767, Q9MYU4, P79784, and 018956). Other sequences would be readily apparent to the skilled artisan, e.g., using publicly available databases known in the art.

As used herein, the terms "nucleotide monophosphatase" and "NMPase" refer to enzymes that catalyze the removal of a phosphate group to convert a nucleotide monophosphate to a nucleoside. Examples of NMPases are "ecto-5' nucleotidase" and "eN," which refer to enzymes that catalyze the 5' hydrolysis of nucleotide monophosphates to nucleosides. One example of eN is ecto-5'-nucleotidase (CD73). CD73 hydrolyzes nucleotide monophosphates, such as adenosine monophosphate (AMP), nicotinamide adenine dinucleotide (NAD), and nicotinamide mononucleotide (NMN) to remove the phosphate groups, e.g., to adenosine, nicotinamide adenine dinucleoside, and nicotinamide mononucleoside, respectively. CD73 is a GPI-anchored protein and contains an extracellular catalytic domain. Full-length human CD73 has the following amino acid sequence (UniProt P21589):

(SEQ ID NO: 13)

```
MCPRAARAPATLLLALGAVLWPAAGAWELTILHTNDVHSRLEQTSEDSSK
CVNASRCMGGVARLFTKVQQIRRAEPNVLLLDAGDQYQGTIWFTVYKGAE
```

-continued

```
VAHFMNALRYDAMALGNHEFDNGVEGLIEPLLKEAKFPILSANIKAKGPL
ASQISGLYLPYKVLPVGDEVVGIVGYTSKETPFLSNPGTNLVFEDEITAL
QPEVDKLKTLNVNKIIALGHSGFEMDKLIAQKVRGVDVVVGGHSNTFLYT
GNPPSKEVPAGKYPFIVTSDDGRKVPVVQAYAFGKYLGYLKIEFDERGNV
ISSHGNPILLNSSIPEDPSIKADINKWRIKLDNYSTQELGKTIVYLDGSS
QSCRFRECNMGNLICDAMINNNLRHTDEMFWNHVSMCILNGGGIRSPIDE
RNNGTITWENLAAVLPFGGTFDLVQLKGSTLKKAFEHSVHRYGQSTGEFL
QVGGIHVVYDLSRKPGDRVVKLDVLCTKCRVPSYDPLKMDEVYKVILPNF
LANGGDGFQMIKDELLRHDSGDQDINVVSTYISKMKVIYPAVEGRIKFST
GSHCHGSFSLIFLSLWAVIFVLYQ
```

Full-length CD73 includes an N-terminal 26 amino acid signal peptide and a C-terminal 25 amino acid propeptide that are removed during maturation, yielding a 523 amino acid fragment, corresponding to residues 27-549 (SEQ ID NO: 2). CD73 encompasses all biologically active fragments, truncations, mutants, variants, substitutions, or derivatives thereof. An exemplary CD73 fragment is the polypeptide of SEQ ID NO: 1. CD73 includes all polypeptides having at least 50%, 60%, 70%, 80%, 85%, 90%, 95%, 97%, 99%, or 100% sequence identity to SEQ ID NO: 13 or to SEQ ID NO: 2. The term cd73 also includes homologs from other species, such as mouse, rat, pig, chicken, bovine, and the like (see, e.g., UniProt sequences Q61503, P21588, Q05927, and H2QTC9). Other sequences would be readily apparent to the skilled artisan, e.g., using publicly available databases known in the art.

Other Examples of NMPases are alkaline phosphatase (ALP) and acid phosphatase (AP). ALPs include, for example, intestinal alkaline phosphatase (IALP, e.g., human IALP UniProt P09923, A0A024R4A2), placental alkaline phosphatase (PALP, e.g., human PALP UniProt P05187), tissue nonspecific alkaline phosphatase (TNSALP, e.g., human TNSALP UniProt P05186), and germ cell alkaline phosphatase (GALP, e.g., human GALP P10696). Acid phosphatase includes, for example, prostatic acid phosphatase (PAP, e.g., human PAP UniProt P15309).

The term NMPase includes all biologically active fragments, truncations, mutants, variants, substitutions, or derivatives thereof, e.g., of any of the foregoing protein or gene sequences. The term NMPase also includes homologs from other species, such as mouse, rat, pig, chicken, bovine, and the like. Other sequences would be readily apparent to the skilled artisan, e.g., using publicly available databases known in the art. NMPases are described, e.g., in Melo et al. (*Am J Physiol Gastointest Liver Physiol* 15:G826-838, 2014) and Pettengil et al. (*J Biol Chem* 20:27315-27316, 2013), which are hereby incorporated by reference in their entirety.

As used herein, the term "fragment" is meant a portion of a polypeptide or nucleic acid molecule that contains, preferably, at least 10%, 20%, 30%, 40%, 50%, 60%, 70%, 75%, 80%, 85%, 90%, 95%, 96%, 97%, 98%, 99%, or more of the entire length of the reference nucleic acid molecule or polypeptide. A fragment may contain, e.g., 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 400, 500, or more amino acid residues, up to the entire length of the polypeptide. Exemplary fragments include the CD39 fragment of SEQ ID NO: 1 and the CD73 fragment of SEQ ID NO: 2, which are soluble fragments that include their respective catalytic domains.

As used herein, the term "nucleoside" refers to molecules containing a nucleobase (nitrogenous base) and a five-carbon sugar, such as ribose or 2'-deoxyribose. Examples of nucleosides include cytidine, uridine, adenosine, guanosine, thymidine, and inosine. As used herein, the term "nucleotide" refers to a nucleoside a phosphate group, generally of one to three phosphates. Examples of nucleotides include nucleoside triphosphates, such as adenosine triphosphate (ATP), guanosine triphosphate (GTP), cytidine triphosphate (CTP), thymidine triphosphate (TTP), and uridine triphosphate (UTP). In some instances, the terms "nucleoside" and "nucleotide" may be used interchangeably and would be well understood to the skilled artisan as context will dictate.

As used herein, the term "percent (%) identity" refers to the percentage of amino acid residues of a candidate sequence, e.g., a mutant NMPase (e.g., eN) or an E-NTPDase, that are identical to the amino acid residues of a reference sequence, e.g., a wild-type Melittin polypeptide, after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid sequence identity of a given candidate sequence to, with, or against a given reference sequence (which can alternatively be phrased as a given candidate sequence that has or includes a certain percent amino acid sequence identity to, with, or against a given reference sequence) is calculated as follows:

$$100\times(\text{fraction of } A/B)$$

where A is the number of amino acid residues scored as identical in the alignment of the candidate sequence and the reference sequence, and where B is the total number of amino acid residues in the reference sequence. In some embodiments where the length of the candidate sequence does not equal to the length of the reference sequence, the percent amino acid sequence identity of the candidate sequence to the reference sequence would not equal to the percent amino acid sequence identity of the reference sequence to the candidate sequence.

As used herein, the term "pharmaceutically acceptable carrier" refers to an excipient or diluent in a pharmaceutical composition. The pharmaceutically acceptable carrier is compatible with the other ingredients of the formulation and not deleterious to the recipient. The pharmaceutically acceptable carrier may provide pharmaceutical stability to the pore forming polypeptide or may impart another beneficial characteristic (e.g., sustained release characteristics). The nature of the carrier differs with the mode of administration. For example, for intravenous administration, an aqueous solution carrier is generally used; for oral administration, a solid carrier is preferred.

As used herein, the term "pharmaceutical composition" refers to a medicinal or pharmaceutical formulation that contains an active ingredient at a pharmaceutically acceptable purity as well as one or more excipients and diluents to enable the active ingredient suitable for the method of administration. The pharmaceutical composition includes pharmaceutically acceptable components that are compatible with, for example, a polypeptide. The pharmaceutical composition may be in aqueous form, for example, for intravenous or subcutaneous administration or in tablet or capsule form, for example, for oral administration.

As used herein, the term "subject" refers to a mammal, e.g., a human.

As used herein, the term "therapeutically effective amount" refers to an amount, e.g., a pharmaceutical dose, effective in inducing a desired biological effect in a subject or patient or in treating a patient having a condition or disorder described herein. It is also to be understood herein that a "therapeutically effective amount" may be interpreted as an amount giving a desired therapeutic effect, either taken in one dose or in any dosage or route, taken alone or in combination with other therapeutic agents.

As used herein, the terms "treatment" or "treating" refer to reducing or ameliorating a disorder and/or one or more symptoms associated therewith. It will be appreciated that, although not precluded, treating a disorder or condition does not require that the disorder or symptoms associated therewith be completely eliminated. Reducing or decreasing the side effects of a disease or condition or the risk or progression of the disease or condition may be relative to a subject who did not receive treatment, e.g., a control, a baseline, or a known control level or measurement. The reduction or decrease may be, e.g., by about 1%, 2%, 3%, 4%, 5%, 6%, 7%, 8%, 9%, 10%, 20%, 30%, 40%, 50%, 60%, 70%, 80%, 90%, 95%, 97%, 99%, or about 100% relative to the subject who did not receive treatment or the control, baseline, or known control level or measurement. Various assays or efficacy metrics for a given disorder or disease are described in more detail below.

BRIEF DESCRIPTION OF THE DRAWINGS

FIG. 9A: Collagen 2 μg/ml; CD39-CD73 bifunctional fusion: 5 μg/ml, 1 μg/ml, 0.2 μg/ml, or Collagen only. FIG. 9B: Trap6 12.5 nM; CD39-CD73 bifunctional fusion, 66 μg/ml, 33 μg/ml, or Trap6 only.

DETAILED DESCRIPTION

Figure 1A:
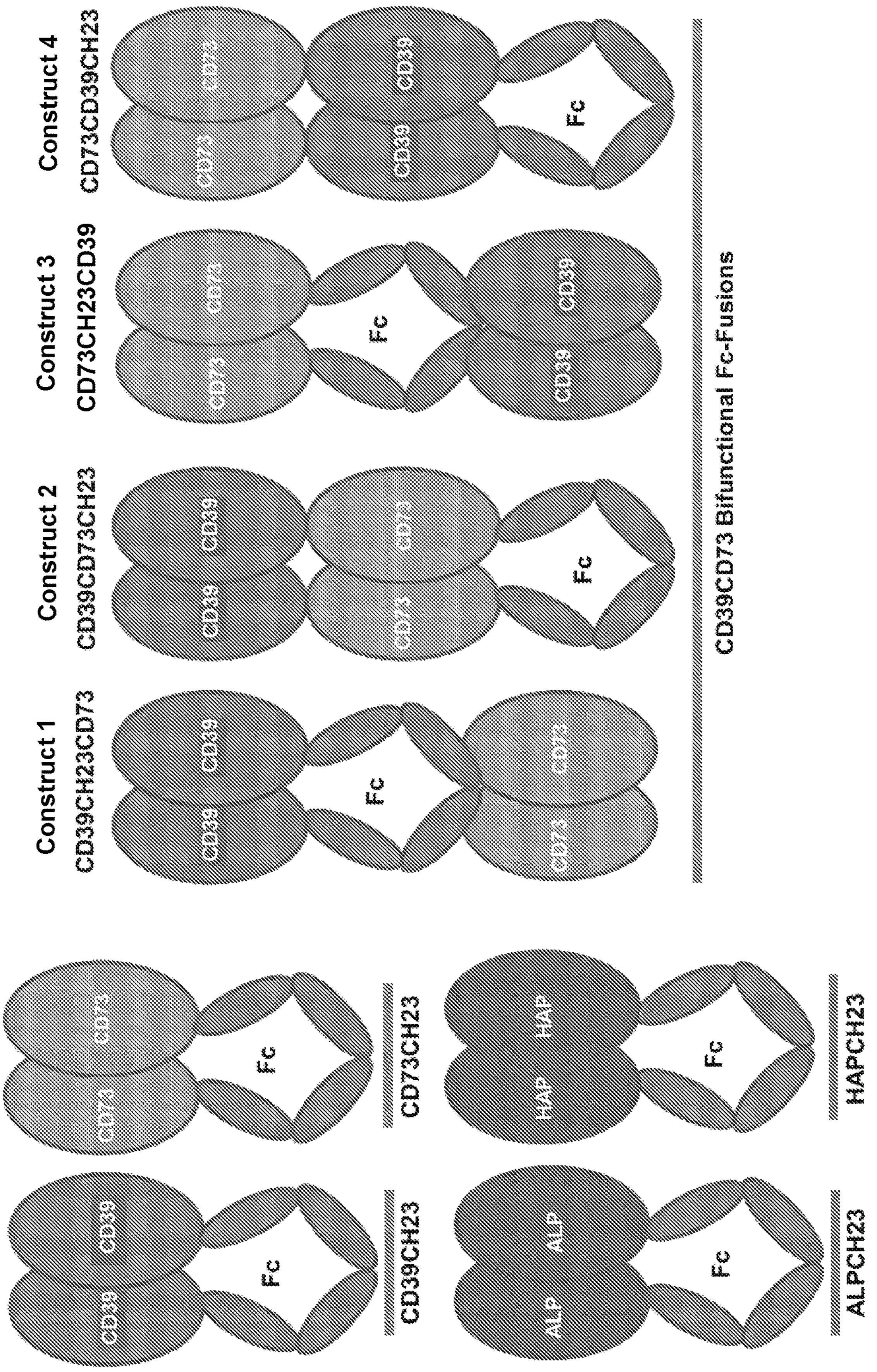
FIG. 1A is a set of schematic drawings showing bifunctional fusions of CD39 and CD73 and control fusion proteins. The CD39-CD73 bifunctional chimeric proteins were bioengineered by fusing the ecto-domain (ECD) of human CD39 and CD73 to either N- or C-termini of Fc region of human $IgG_1$ and to each other. To generate activity comparison controls, human CD39-ECD-Fc Fusion (CD39CH23; SEQ ID NO: 43), human CD73-ECD-Fc fusion (CD73CH23; SEQ ID NO: 44), human alkaline phosphatase ECD-Fc fusion (ALPCH23; SEQ ID NO: 45), and human acid phosphatase ECD-Fc (HAPCH23; SEQ ID NO: 46), were also generated.

Extracellular di- and tri-phosphate nucleotides are released from activated or injured cells to trigger vascular and immune P2 purinergic receptors, provoking inflammation and vascular thrombosis. These metabokines are scavenged by ecto-nucleoside triphosphate diphosphohydrolase-1 (E-NTPDase1; CD39). Further degradation of the mono-phosphate nucleoside end-products occurs by surface ecto-5'-nucleotidase (NMPase; CD73). These ecto-enzymatic processes, in tandem, promote adenosinergic responses, which are immunosuppressive and antithrombotic. However, such homeostatic ecto-enzymatic mechanisms are lost in a setting of oxidative stress, which consequently boosts inflammatory processes.

Described herein are bifunctional enzymes containing ectodomains (ECDs) of an E-NTPDase (e.g., NTPDase 1 (CD39), NTPDase2, NTPDase3, NTPDase4, NTPDase5, NTPDase6, NTPDase7, or NTPDase8, e.g., CD39) and an NMPase, such as eN (e.g., CD73), alkaline phosphatase (ALP), or acid phosphatase (AP) within a single polypeptide. The polypeptides containing these bifunctional enzymes are capable of hydrolyzing extracellular tri- and di-phosphate nucleotides directly to nucleosides and can be used therapeutically to ameliorate inflammatory diseases. Surprisingly, these bifunctional polypeptides were superior in catalyzing conversion tri- and di-phosphate nucleotides into nucleosides when compared to alkaline phosphatase and acid phosphatase fusion proteins or single polypeptide enzymes in combination (i.e., not as a fusion protein). Furthermore, the polypeptides described herein were shown to have beneficial impacts on platelet activation in vitro, confirming their therapeutic utility for converting pro-inflammatory ATP into anti-inflammatory adenosine. The polypeptides and methods of use thereof of the present disclosure are described in more detail below.

Polypeptides

The polypeptides described herein include an ectonucleoside triphosphate diphosphohydrolase (E-NTPDase) and an NMPase, such as ecto-5' nucleotidase (eN), ALP, or AP. The E-NTPDase and eN may be connected, e.g., by a linker of, e.g., at least one amino acid. The polypeptide may also include additional amino acid residues, e.g., spacers, at the N- or C-termini of the polypeptide or anywhere therebetween. For example, the polypeptide may have a structure from N-terminus to C-terminus of A-(E-NTPDase)-L-eN-B; or A-eN-L-(E-NTPDase)-B, in which A is absent or is an amino acid sequence of one or more amino acids, B is absent or is an amino acid sequence of one or more amino acids, and L is absent or is a linker, e.g., a chemical linker or a polypeptide linker of one or more (e.g., 1 to 20) amino acids.

The polypeptide may have a structure from N-terminus to C-terminus of A-(E-NTPDase)-L-ALP-B; or A-ALP-L-(E-NTPDase)-B; wherein A is absent or is an amino acid sequence of one or more amino acids; B is absent or is an amino acid sequence of one or more amino acids; and L is absent or is a linker, e.g., a chemical linker or a polypeptide linker of one or more amino acids.

The polypeptide may have a structure from N-terminus to C-terminus of A-(E-NTPDase)-L-AP-B; or A-AP-L-(E-NTPDase)-B; wherein A is absent or is an amino acid sequence of one or more amino acids; B is absent or is an amino acid sequence of one or more amino acids; and L is absent or is a linker, e.g., a chemical linker or a polypeptide linker of one or more amino acids.

The E-NTPDase may be ectonucleoside triphosphate diphosphohydrolase-1 (NTPDase1, E-NTPase1, CD39), NTPDase2, NTPDase3, NTPDase4, NTPDase5, NTPDase6, NTPDase7, or NTPDase8 or a biologically active truncation, mutant, or derivative thereof. In particular, the E-NTPDase is an ECD of a known E-NTPDase. The E-NTPDase can also be a variant of a known E-NTPDase, such as those described herein, that has at least 80% (e.g., at least 85%, 90%, 95%, 97%, or 99%) sequence identity to the amino acid or nucleic acid sequence of the known E-NTPDase sequence. The variant E-NTPDase may contain only the region corresponding to the ECD of the known E-NTPDase.

The E-NTPDase may be CD39 or a biologically active truncation, mutant, or derivative thereof. The CD39 may have at least 80% (e.g., at least 85%, 90%, 95%, 97%, or 99%) sequence identity to SEQ ID NO: 1 or 12. The CD39 may include or consist of the sequence of SEQ ID NO: 1 or 12.

The eN may be ecto-5'-nucleotidase (CD73) or a biologically active truncation, mutant, or derivative thereof. The CD73 may have at least 80% (e.g., at least 85%, 90%, 95%, 97%, or 99%) sequence identity to SEQ ID NO: 2 or 13. The CD73 may include or consist of the sequence of SEQ ID NO: 2 or 13.

The polypeptides described herein may have a structure from N-terminus to C-terminus of A-CD39-L-CD73-B; or A-CD73-L-CD39-B; wherein A is absent or is an amino acid sequence of one or more amino acids; B is absent or is an amino acid sequence of one or more amino acids; and L is absent or is a linker, e.g., a chemical linker or a polypeptide linker of one or more (e.g., 1 to 20) amino acids.

In some embodiments, the polypeptide has at least 80% (e.g., at least 80%, 85%, 90%, 95%, 97%, or 99%) sequence identity to SEQ ID NOs: 8 or 9 (i.e., A-CD39-L-CD73-Fc; or A-CD73-L-CD39-Fc). For example, the polypeptide may include or consist of the sequence of SEQ ID NOs: 8 or 9 (i.e., A-CD39-L-CD73-Fc; or A-CD73-L-CD39-Fc). The polypeptide may have at least 80% (e.g., at least 85%, 90%, 95%, 97%, or 99%) sequence identity to SEQ ID NOs: 10 or 11 (i.e., A-CD39-Fc-CD73-B; or A-CD73-Fc-CD39-B). For example, the polypeptide may include or consist of the sequence of SEQ ID NOs: 10 or 11 (i.e., A-CD39-Fc-CD73-B; or A-CD73-Fc-CD39-B).

Other polypeptides described herein include fusions of CD39 or CD73 and an FC domain (e.g., the polypeptides of SEQ ID NOs: 46 and 47 and variants thereof having at least 80% sequence identity thereto). The polypeptides may be formulated as a combination.

Linkers, Spacers, and Terminal Residues

The polypeptides described herein may optionally include a linker, spacer, and or terminal regions. The polypeptides may include a linker between the E-NTPDase (e.g., CD39 or fragment thereof) and the NMPase, e.g., eN (e.g., CD73 or a fragment thereof), ALP, and AP. The linker may be a polypeptide linker or a chemical linker. Alternatively, the linker may be absent.

The polypeptide may also include additional amino acid residues, e.g., spacers or terminal regions, at the N- or C-termini of the polypeptide or anywhere therebetween. For example, A and/or B, may each be, independently, 1, 2, 3, 4, 5, 6, 7, 8, 9, 10, 20, 30, 40, 50, 60, 70, 80, 90, 100, 200, 300, 400, 500, or more amino acids long. A and/or B may each be, independently, e.g., from about 1 to about 500 amino acids (e.g., about 1 to about 400, about 1 to about 300, about 5 to about 300, about 5 to about 200, about 5 to about 100, about 5 to about 50, about 5 to about 30, about 10 to about 30, about 10 to about 20) long.

In some embodiments, A, B, and/or L includes one or more glycines, serines, or a combination thereof (e.g., 2, 3, 4, 5, 6, 7, 8, 9, 10, 11, 12, 13, 14, 15, 16, 17, 18, 19, or 20 or more glycines, serines, or a combination thereof). For example, A, B, and/or L may include a polyglycine linker. The polyglycine linker may consist of the sequence of GGGG (SEQ ID NO: 3).

In some embodiments, A, B, and/or L includes a fragment crystallizable (Fc) domain. The Fc domain may be, e.g., IgG-1, IgG-2, IgG-3, IgG-3 or IgG-4, including the CH2 and CH3 domains of the immunoglobulin heavy chain. The Fc may also include any portion of the hinge region joining the Fab and Fc regions. The Fc can be of any mammal, including human, and may be post-translationally modified (e.g., by glycosylation). The Fc domain may be an IgG1 Fc domain. The Fc domain may have at least 80% (e.g., at least 85%, 90%, 95%, 97%, or 99%) sequence identity to SEQ ID NO: 5. The Fc domain may include or consist of the sequence of SEQ ID NO: 5.

In some embodiments, A, B, and/or L includes a half-life extending moiety, such as albumin (e.g., human serum albumin).

A, B, and/or L may include a polyglycine linker and an Fc domain. A, B, and/or L may include GGGG (SEQ ID NO: 3)-Fc and/or GGGG (SEQ ID NO: 3)-Fc-GGGG (SEQ ID NO: 3). For example, A, B, and/or L may have at least 80% (e.g., at least 85%, 90%, 95%, 97%, or 99%) sequence identity to SEQ ID NOs: 6 or 7. A, B, and/or L may include or consist of the sequence of SEQ ID NOs: 6 or 7. A, B, and/or L may have at least 80% (e.g., at least 85%, 90%, 95%, 97%, or 99%) sequence identity to SEQ ID NO: 4. For example, A may include or consist of the sequence of SEQ ID NO: 4. L may include or consist of GGGG (SEQ ID NO: 3), and B may include GGGG (SEQ ID NO: 3)-Fc. In some embodiments, L includes GGGG (SEQ ID NO: 3)-Fc-GGGG (SEQ ID NO: 3).

Peptide Linkers

A linker may be, e.g., 1, 2, 3, 4, 5, 6, 7, 8, 9, 10, 20, 30, 40, 50, 60, 70, 80, 90, 100, 200, 300, 400, 500, or more amino acids long. The linker may be, e.g., from about 1 to about 500 amino acids (e.g., about 1 to about 400, about 1 to about 300, about 1 to about 20, about 5 to about 300, about 5 to about 200, about 5 to about 100, about 5 to about 50, about 5 to about 30, about 10 to about 30, about 10 to about 20) long.

Suitable peptide linkers are known in the art, and include, for example, peptide linkers containing flexible amino acid residues such as glycine and serine. In certain embodiments, a linker can contain motifs, e.g., multiple or repeating motifs, of GS, GGS, GGGGS (SEQ ID NO: 14), GGSG (SEQ ID NO: 15), or SGGG (SEQ ID NO: 16). In certain embodiments, a linker can contain 2 to 12 amino acids including motifs of GS, e.g., GS, GSGS (SEQ ID NO: 17), GSGSGS (SEQ ID NO: 18), GSGSGSGS (SEQ ID NO: 19), GSGSGSGSGS (SEQ ID NO: 20), or GSGSGSGSGSGS (SEQ ID NO: 21). In certain other embodiments, a linker can contain 3 to 12 amino acids including motifs of GGS, e.g., GGS, GGSGGS (SEQ ID NO: 22), GGSGGSGGS (SEQ ID NO: 23), and GGSGGSGGSGGS (SEQ ID NO: 24). In yet other embodiments, a linker can contain 4 to 12 amino acids including motifs of GGSG (SEQ ID NO: 15), e.g., GGSGGGSG (SEQ ID NO: 25), or GGSGGGSGGGSG (SEQ ID NO: 26). In other embodiments, a linker can contain motifs of GGGGS (SEQ ID NO: 14), e.g., GGGGSGGGGSGGGGS (SEQ ID NO: 27). In certain embodiments, a linker is SGGGSGGGSGGGSGGGSGGG (SEQ ID NO: 28).

In some embodiments, a peptide linker is a peptide linker including the amino acid sequence of any one of (GS)x, (GGS)x, (GGGGS)x (SEQ ID NO: 14), (GGSG)x (SEQ ID NO: 15), (SGGG)x (SEQ ID NO: 16), wherein x is an integer from 1 to 50 (e.g., 1-40, 1-30, 1-20, 1-10, or 1-5). In some embodiments, the peptide linker has the amino acid sequence (GGGGS)x (SEQ ID NO: 15), wherein x is an integer selected from 1, 2, 3, 4, 5, 6, 7, 8, 9, or 10.

In some embodiments, a peptide linker contains only glycine residues, e.g., at least 4 glycine residues (e.g., 4-200, 4-180, 4-160, 4-140, 4-40, 4-100, 4-90, 4-80, 4-70, 4-60, 4-50, 4-40, 4-30, 4-20, 4-19, 4-18, 4-17, 4-16, 4-15, 4-14, 4-13, 4-12, 4-11, 4-10, 4-9, 4-8, 4-7, 4-6 or 4-5 glycine residues) (e.g., 4-200, 6-200, 8-200, 10-200, 12-200, 14-200, 16-200, 18-200, 20-200, 30-200, 40-200, 50-200, 60-200, 70-200, 80-200, 90-200, 100-200, 120-200, 140-200, 160-200, 180-200, or 190-200 glycine residues). In certain embodiments, a linker has 4-30 glycine residues (e.g., 4, 5, 6, 7, 8, 9, 10, 11, 12, 13, 14, 15, 16, 17, 18, 19, 20, 21, 22, 23, 24, 25, 26, 27, 28, 29, or 30 glycine residues). In some embodiments, a linker containing only glycine residues may not be glycosylated (e.g., O-linked glycosylation, also referred to as O-glycosylation) or may have a decreased level of glycosylation (e.g., a decreased level of O-glycosylation) (e.g., a decreased level of O-glycosylation with glycans such as xylose, mannose, sialic acids, fucose (Fuc), and/or galactose (Gal) (e.g., xylose)) as compared to, e.g., a linker containing one or more serine residues.

In some embodiments, a linker containing only glycine residues may not be O-glycosylated (e.g., O-xylosylation) or may have a decreased level of O-glycosylation (e.g., a decreased level of O-xylosylation) as compared to, e.g., a linker containing one or more serine residues.

In some embodiments, a linker containing only glycine residues may not undergo proteolysis or may have a decreased rate of proteolysis as compared to, e.g., a linker containing one or more serine residues.

In certain embodiments, a linker can contain motifs of GGGG (SEQ ID NO: 3), e.g., GGGGGGGG (SEQ ID NO: 29), GGGGGGGGGGGG (SEQ ID NO: 30), GGGGGGGGGGGGGGGG (SEQ ID NO: 31), or GGGGGGGGGGGGGGGGGGGG (SEQ ID NO: 32). In certain embodiments, a linker can contain motifs of GGGGG (SEQ ID NO: 33), e.g., GGGGGGGGGG (SEQ ID NO: 34) or GGGGGGGGGGGGGGG (SEQ ID NO: 35).

In other embodiments, a linker can also contain amino acids other than glycine and serine, e.g., GENLYFQSGG (SEQ ID NO: 36), SACYCELS (SEQ ID NO: 37), RSIAT (SEQ ID NO: 38), RPACKIPNDLKQKVMNH (SEQ ID NO: 39), GGSAGGSGSGSSGGSS-GASGTGTAGGTGSGSGTGSG (SEQ ID NO: 40), AAANSSIDLISVPVDSR (SEQ ID NO: 41), or GGSGGGSEGGGSEGGGSEGGGSEGGGSEGGGSGGGS (SEQ ID NO: 42).

Chemical Linkers

In some embodiments, the two polypeptide domains are connected via a chemical linker. A chemical linker provides space, rigidity, and/or flexibility between two or more components of the fusion protein or conjugate. In some embodiments, a linker may be a bond, e.g., a covalent bond, e.g., an amide bond, a disulfide bond, a C—O bond, a C—N bond, a N—N bond, a C—S bond, or any kind of bond created from a chemical reaction, e.g., chemical conjugation. In some embodiments, a linker includes no more than 250 atoms (e.g., 1-2, 1-4, 1-6, 1-8, 1-10, 1-12, 1-14, 1-16, 1-18, 1-20, 1-25, 1-30, 1-35, 1-40, 1-45, 1-50, 1-55, 1-60, 1-65, 1-70, 1-75, 1-80, 1-85, 1-90, 1-95, 1-100, 1-110, 1-120, 1-130, 1-140, 1-150, 1-160, 1-170, 1-180, 1-190, 1-200, 1-210, 1-220, 1-230, 1-240, or 1-250 atom(s); 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 28, 26, 24, 22, 20, 18, 16, 14, 12, 10, 9, 8, 7, 6, 5, 4, 3, 2, or 1 atom(s)). In some embodiments, a linker includes no more than 250 non-hydrogen atoms (e.g., 1-2, 1-4, 1-6, 1-8, 1-10, 1-12, 1-14, 1-16, 1-18, 1-20, 1-25, 1-30, 1-35, 1-40, 1-45, 1-50, 1-55, 1-60, 1-65, 1-70, 1-75, 1-80, 1-85, 1-90, 1-95, 1-100, 1-110, 1-120, 1-130, 1-140, 1-150, 1-160, 1-170, 1-180, 1-190, 1-200, 1-210, 1-220, 1-230, 1-240, or 1-250 non-hydrogen atom(s); 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 28, 26, 24, 22, 20, 18, 16, 14, 12, 10, 9, 8, 7, 6, 5, 4, 3, 2, or 1 non-hydrogen atom(s)). In some embodiments, the backbone of a linker includes no more than 250 atoms (e.g., 1-2, 1-4, 1-6, 1-8, 1-10, 1-12, 1-14, 1-16, 1-18, 1-20, 1-25, 1-30, 1-35, 1-40, 1-45, 1-50, 1-55, 1-60, 1-65, 1-70, 1-75, 1-80, 1-85, 1-90, 1-95, 1-100, 1-110, 1-120, 1-130, 1-140, 1-150, 1-160, 1-170, 1-180, 1-190, 1-200, 1-210, 1-220, 1-230, 1-240, or 1-250 atom(s); 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 28, 26, 24, 22, 20, 18, 16, 14, 12, 10, 9, 8, 7, 6, 5, 4, 3, 2, or 1 atom(s)). The "backbone" of a linker refers to the atoms in the linker that together form the shortest path from one part of the conjugate to another part of the conjugate. The atoms in the backbone of the linker are directly involved in linking one part of the conjugate to another part of the conjugate. For examples, hydrogen atoms attached to carbons in the backbone of the linker are not considered as directly involved in linking one part of the conjugate to another part of the conjugate.

Molecules that may be used to make linkers include at least two functional groups, e.g., two carboxylic acid groups. In some embodiments of a divalent linker, the divalent linker may contain two carboxylic acids, in which the first carboxylic acid may form a covalent linkage with one component in the conjugate and the second carboxylic acid may form a covalent linkage (e.g., a C—S bond or a C—N bond) with another component in the conjugate.

In some embodiments, dicarboxylic acid molecules may be used as linkers (e.g., a dicarboxylic acid linker). Examples of dicarboxylic acids molecules that may be used to form linkers include, but are not limited to,

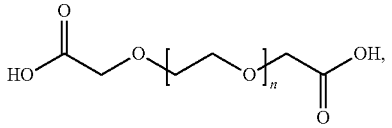

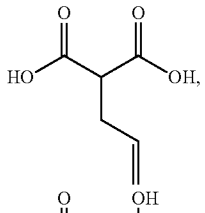 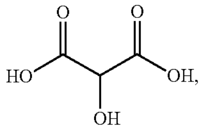

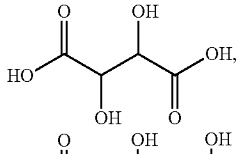

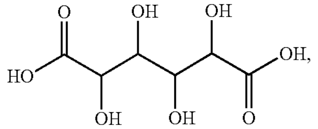

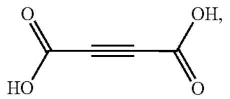 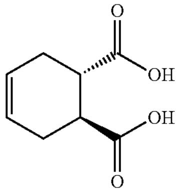 ,

-continued
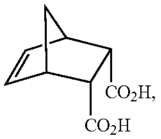
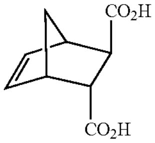
,
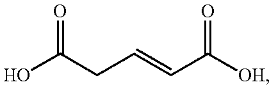
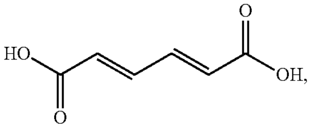
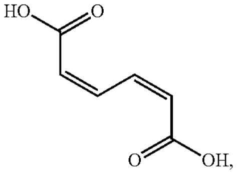
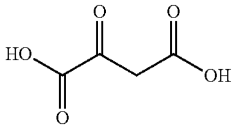
,
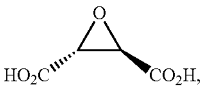
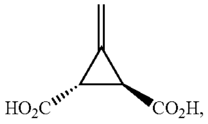
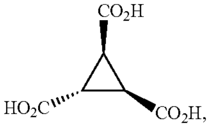
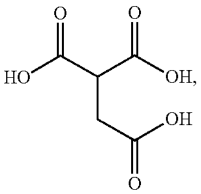
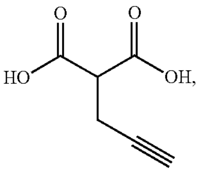
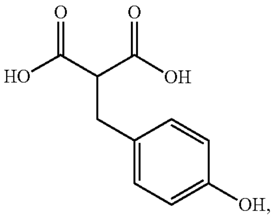
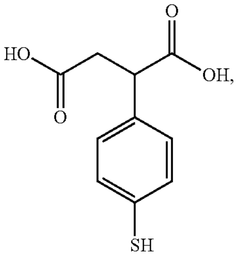
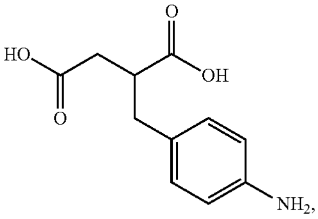
-continued
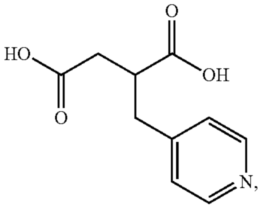
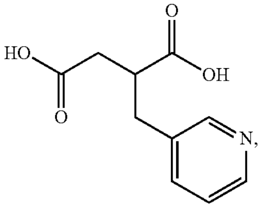
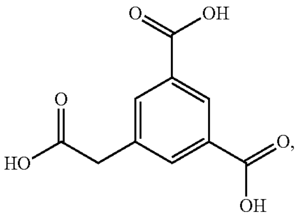
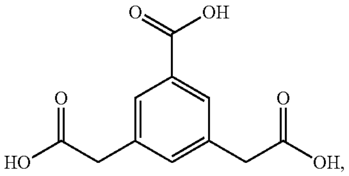
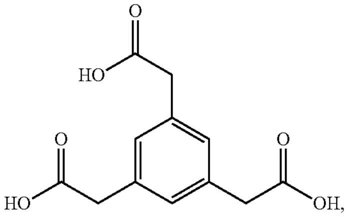
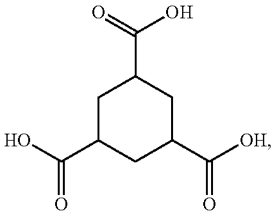
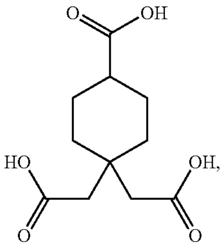
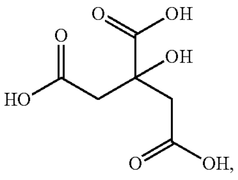
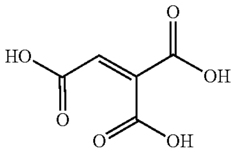
, -continued
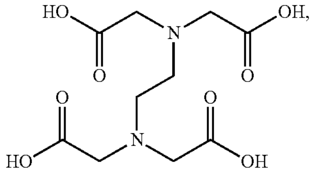
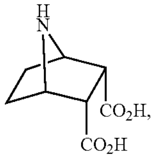
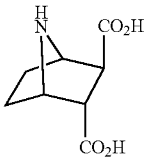
,
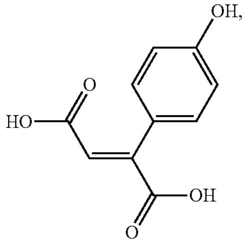
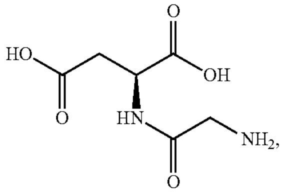
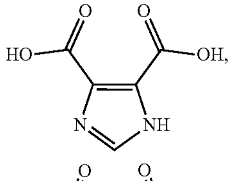
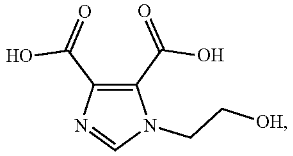
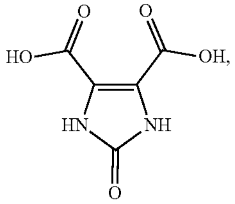
and
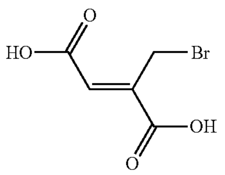
wherein n is an integer from 1 to 20 (e.g., n is 1, 2, 3, 4, 5, 6, 7, 8, 9, 10, 11, 12, 13, 14, 15, 16, 17, 18, 19, or 20).
Other examples of dicarboxylic acids molecules that may be used to form linkers include, but are not limited to,
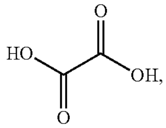
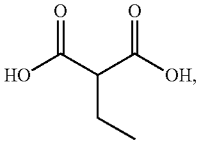
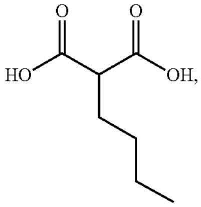
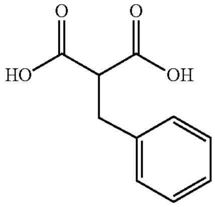
,
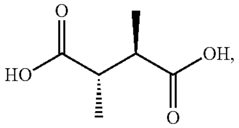
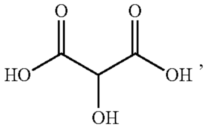
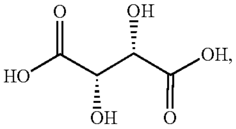
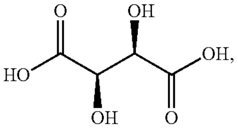
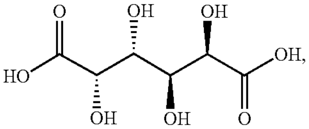
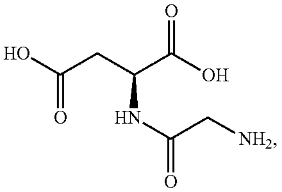
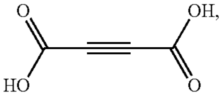
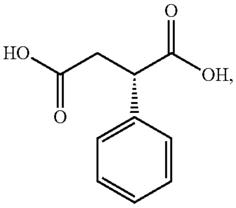
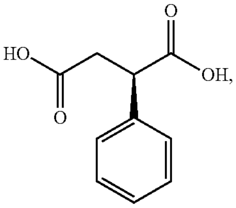
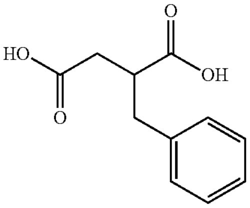
,
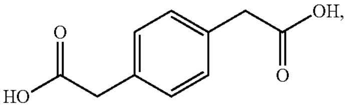
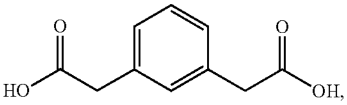

-continued
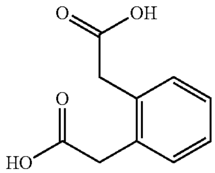,
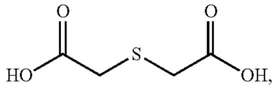
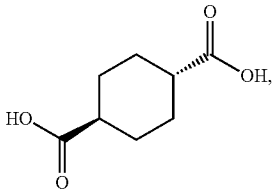
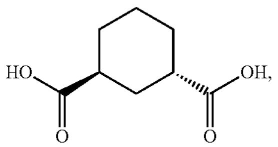
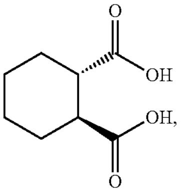
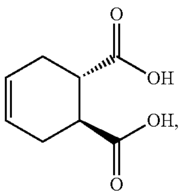
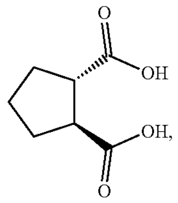
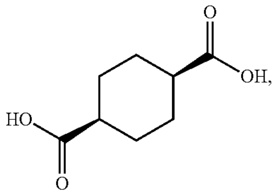
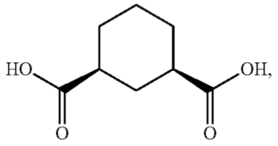
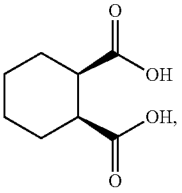
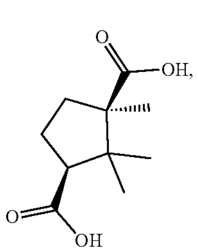
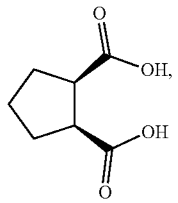
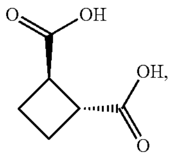
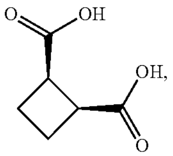
-continued
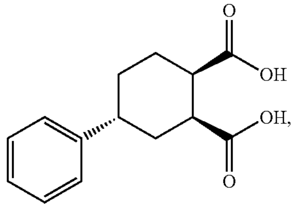
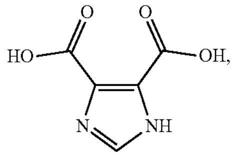
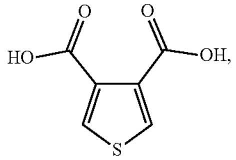
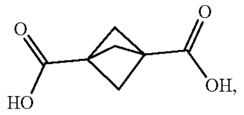
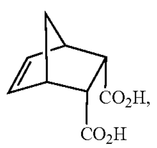
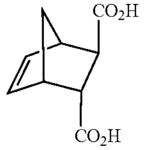,
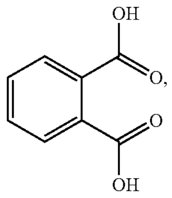
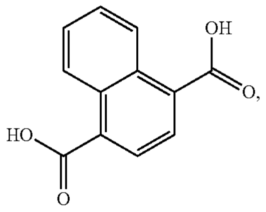
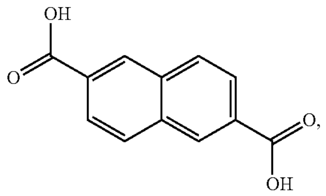
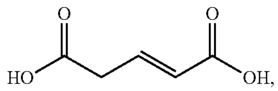
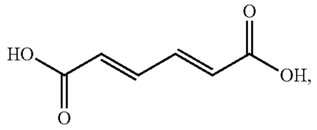
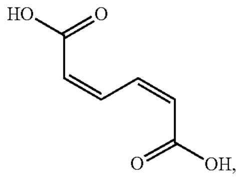
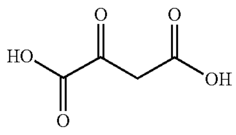,
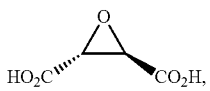
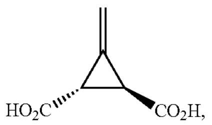
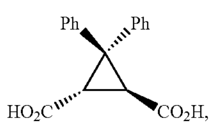
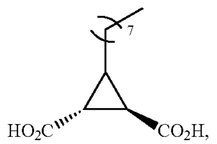

-continued

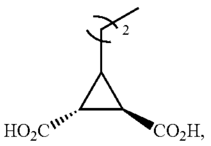

, and

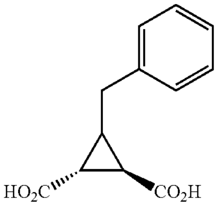

In some embodiments, dicarboxylic acid molecules, such as the ones described herein, may be further functionalized to contain one or more additional functional groups.

In some embodiments, the linking group may include a moiety including a carboxylic acid moiety and an amino moiety that are spaced by from 1 to 25 atoms. Examples of such linking groups include, but are not limited to,

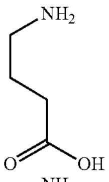

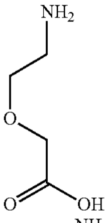

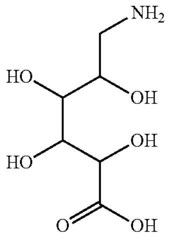

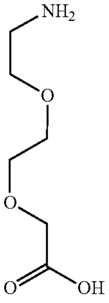

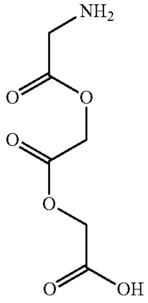

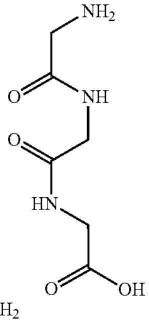

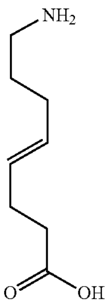

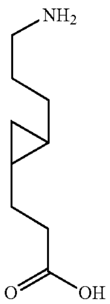

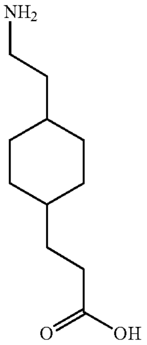

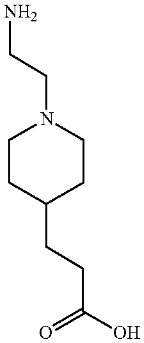

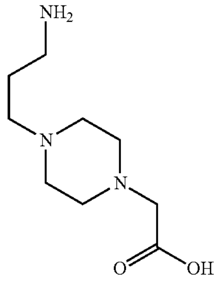

-continued

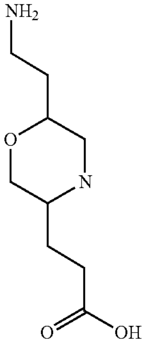

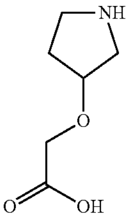

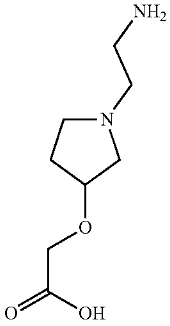

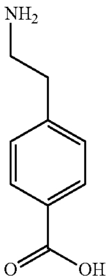

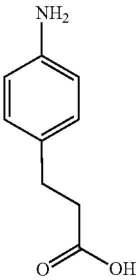

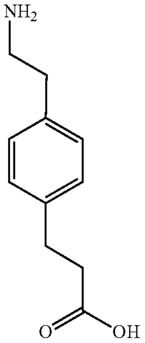

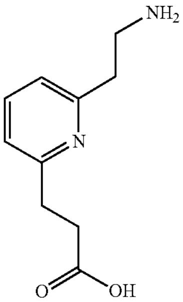

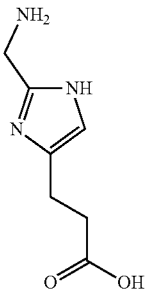

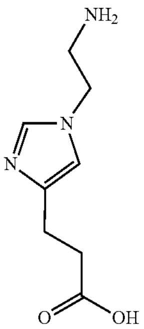

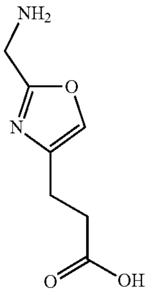

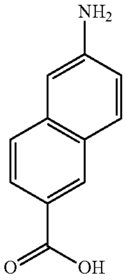

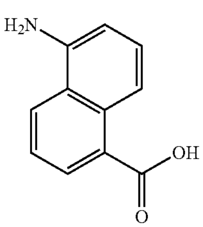

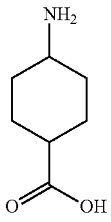

-continued

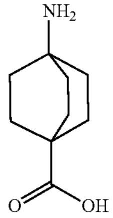
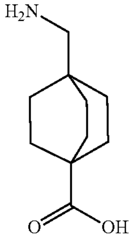
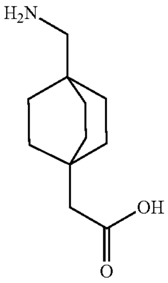
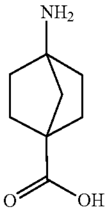
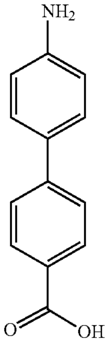
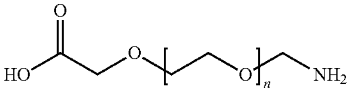

wherein n is an integer from 1 to 20 (e.g., n is 1, 2, 3, 4, 5, 6, 7, 8, 9, 10, 11, 12, 13, 14, 15, 16, 17, 18, 19, or 20).

In some embodiments, a linking group may include a moiety including a carboxylic acid moiety and an amino moiety, such as the ones described herein, may be further functionalized to contain one or more additional functional groups. Such linking groups may be further functionalized, for example, to provide an attachment point to a polypeptide as described herein (e.g., by way of a linker, such as a PEG linker).

In some embodiments, the linking group may include a moiety including two amino moieties (e.g., a diamino moiety) that are spaced by from 1 to 25 atoms. Examples of such linking groups include, but are not limited to,

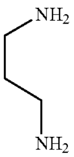
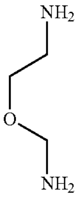
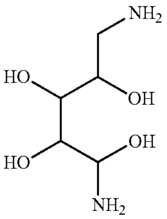
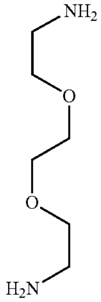
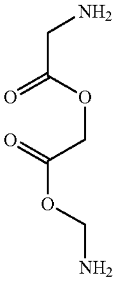
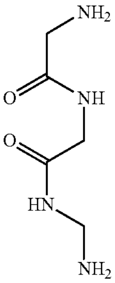

-continued

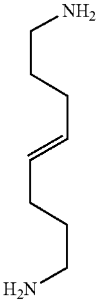
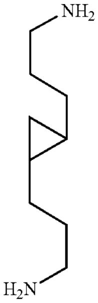
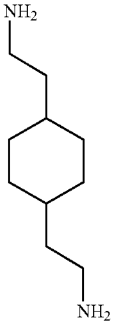
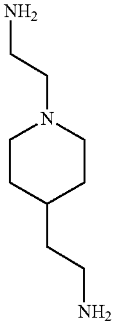
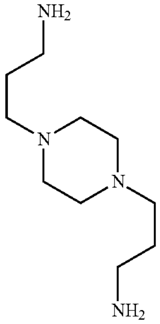
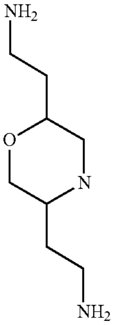
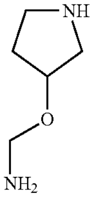
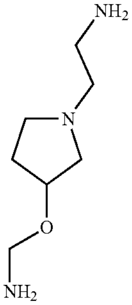
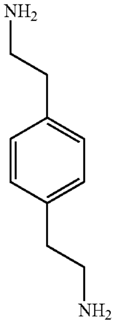
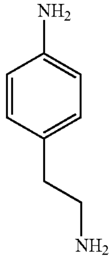
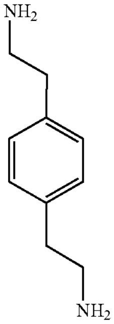
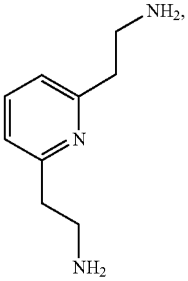
,
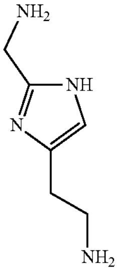

-continued

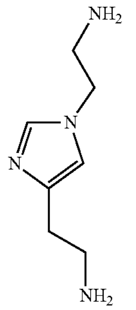 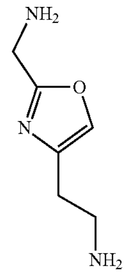 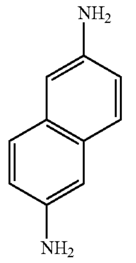

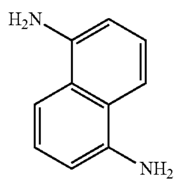 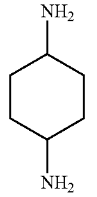

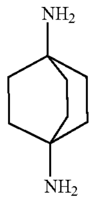 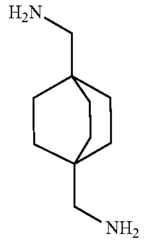

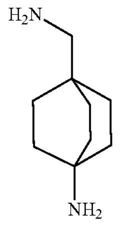 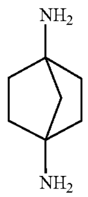 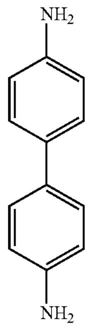

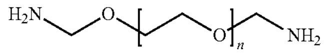

wherein n is an integer from 1 to 20 (e.g., n is 1, 2, 3, 4, 5, 6, 7, 8, 9, 10, 11, 12, 13, 14, 15, 16, 17, 18, 19, or 20).

In some embodiments, a linking group may include a diamino moiety, such as the ones described herein, may be further functionalized to contain one or more additional functional groups. Such diamino linking groups may be further functionalized, for example, to provide an attachment point to a polypeptide as described herein (e.g., by way of a linker, such as a PEG linker).

In some embodiments, a molecule containing an azide group may be used to form a linker, in which the azide group may undergo cycloaddition with an alkyne to form a 1,2,3-triazole linkage. In some embodiments, a molecule containing an alkyne group may be used to form a linker, in which the alkyne group may undergo cycloaddition with an azide to form a 1,2,3-triazole linkage. In some embodiments, a molecule containing a maleimide group may be used to form a linker, in which the maleimide group may react with a cysteine to form a C—S linkage. In some embodiments, a molecule containing one or more haloalkyl groups may be used to form a linker, in which the haloalkyl group may form a covalent linkage, e.g., C—N and C—O linkage.

In some embodiments, a linker may include a synthetic group derived from, e.g., a synthetic polymer (e.g., a polyethylene glycol (PEG) polymer). In some embodiments, a linker may include one or more amino acid residues. In some embodiments, a linker may be an amino acid sequence (e.g., a 1-25 amino acid, 1-10 amino acid, 1-9 amino acid, 1-8 amino acid, 1-7 amino acid, 1-6 amino acid, 1-5 amino acid, 1-4 amino acid, 1-3 amino acid, 1-2 amino acid, or 1 amino acid sequence). In some embodiments, a linker (L or L') may include one or more optionally substituted C1-C20 alkylene, optionally substituted C1-C20 heteroalkylene (e.g., a PEG unit), optionally substituted C2-C20 alkenylene (e.g., C2 alkenylene), optionally substituted C2-C20 heteroalkenylene, optionally substituted C2-C20 alkynylene, optionally substituted C2-C20 heteroalkynylene, optionally substituted $C_3$-$C_{20}$ cycloalkylene (e.g., cyclopropylene, cyclobutylene), optionally substituted $C_2$-$C_{20}$ heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene (e.g., C6 arylene), optionally substituted $C_3$-$C_{15}$ heteroarylene (e.g., imidazole, pyridine), O, S, $NR^i$ ($R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted $C_3$-$C_{20}$cycloalkyl, optionally substituted $C_2$-$C_{20}$ heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted $C_3$-$C_{15}$ heteroaryl), P, carbonyl, thiocarbonyl, sulfonyl, phosphate, phosphoryl, or imino.

Conjugation Chemistries

Covalent conjugation of two or more components in a conjugate using a linker may be accomplished using well-known organic chemical synthesis techniques and methods. Complementary functional groups on two components may react with each other to form a covalent bond. Examples of complementary reactive functional groups include, but are not limited to, e.g., maleimide and cysteine, amine and activated carboxylic acid, thiol and maleimide, activated sulfonic acid and amine, isocyanate and amine, azide and alkyne, and alkene and tetrazine. Site-specific conjugation to a polypeptide may accomplished using techniques known in the art. Exemplary techniques for site-specific conjugation to an Fc domain are provided in Agarwall. P., et al. Bioconjugate Chem. 26:176-192 (2015).

Other examples of functional groups capable of reacting with amino groups include, e.g., alkylating and acylating agents. Representative alkylating agents include: (i) an α-haloacetyl group, e.g., $XCH_2CO$— (where X=Br, Cl, or I); (ii) a N-maleimide group, which may react with amino groups either through a Michael type reaction or through acylation by addition to the ring carbonyl group; (iii) an aryl halide, e.g., a nitrohaloaromatic group; (iv) an alkyl halide; (v) an aldehyde or ketone capable of Schiff's base formation with amino groups; (vi) an epoxide, e.g., an epichlorohydrin and a bisoxirane, which may react with amino, sulfhydryl, or phenolic hydroxyl groups; (vii) a chlorine-containing of s-triazine, which is reactive towards nucleophiles such as amino, sufhydryl, and hydroxyl groups; (viii) an aziridine, which is reactive towards nucleophiles such as amino groups by ring opening; (ix) a squaric acid diethyl ester; and (x) an α-haloalkyl ether.

Examples of amino-reactive acylating groups include, e.g., (i) an isocyanate and an isothiocyanate; (ii) a sulfonyl chloride; (iii) an acid halide; (iv) an active ester, e.g., a nitrophenylester or N-hydroxysuccinimidyl ester; (v) an acid anhydride, e.g., a mixed, symmetrical, or N-carboxyanhydride; (vi) an acylazide; and (vii) an imidoester. Aldehydes and ketones may be reacted with amines to form Schiff's bases, which may be stabilized through reductive amination.

It will be appreciated that certain functional groups may be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as α-haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

In some embodiments, a linker of the invention, is conjugated (e.g., by any of the methods described herein) to a fusion protein, for example the Fc portion of a fusion protein. In some embodiments of the invention, the linker is conjugated by way of: (a) a thiourea linkage (i.e., —NH(C═S)NH—) to a lysine; (b) a carbamate linkage (i.e., —NH(C═O)—O) to a lysine; (c) an amine linkage by reductive amination (i.e., $—NHCH_2$) to a lysine; (d) an amide (i.e., $—NH—(C═O)CH_2$) to a lysine; (e) a cysteine-maleimide conjugate between a maleimide of the linker to a cysteine; (f) an amine linkage by reductive amination (i.e., $—NHCH_2$) between the linker and a carbohydrate (e.g., a glycosyl group of an Fc domain monomer or an Fc domain); (g) a rebridged cysteine conjugate, wherein the linker is conjugated to two cysteines; (h) an oxime linkage between the linker and a carbohydrate (e.g., a glycosyl group of an Fc domain monomer or an Fc domain); (i) an oxime linkage between the linker and an amino acid residue; (j) an azido linkage between the linker; (k) direct acylation of a linker; or (I) a thioether linkage between the linker.

Polynucleotides, Vectors, and Cells

The invention also features polynucleotides encoding a polypeptide as described herein. Also featured is a vector that includes the polynucleotide encoding the polypeptide. Also contemplated herein is a cell that includes the polynucleotide or the vector.

The polypeptides may be produced according to routine methods known to one of skill in the art. The invention also features a method of producing a polypeptide as described herein by providing a cell transformed with a polynucleotide encoding the polypeptide or a vector that includes the polynucleotide and culturing the transformed cell under conditions for expressing the polynucleotide. The culturing results in expression of the polypeptide. The polypeptide may further be isolated from the remainder of the cell culture and/or cellular debris.

Viral Vectors

Also featured are viral vectors encoding the polypeptide that are suitable for administration to a subject, e.g., as a delivery vehicle or as a gene therapy.

Viral genomes provide a rich source of vectors that can be used for the efficient delivery of exogenous genes into a mammalian cell. Viral genomes are particularly useful vectors for gene delivery as the polynucleotides contained within such genomes are typically incorporated into the nuclear genome of a mammalian cell by generalized or specialized transduction. These processes occur as part of the natural viral replication cycle, and do not require added proteins or reagents in order to induce gene integration. Examples of viral vectors are a retrovirus (e.g., Retroviridae family viral vector), adenovirus (e.g., Ad5, Ad26, Ad34, Ad35, and Ad48), parvovirus, coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, human papilloma virus, human foamy virus, and hepatitis virus, for example. Examples of retroviruses are avian leukosis-sarcoma, avian C-type viruses, mammalian C-type, B-type viruses, D-type viruses, oncoretroviruses, HTLV-BLV group, lentivirus, alpharetrovirus, gammaretrovirus, spumavirus (Coffin, J. M., Retroviridae: The viruses and their replication, Virology, Third Edition (Lippincott-Raven, Philadelphia, (1996))). Other examples are murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., (U.S. Pat. No. 5,801,030), the teachings of which are incorporated herein by reference.

Retroviral Vectors

The delivery vector used in the methods and compositions described herein may be a retroviral vector. One type of retroviral vector that may be used in the methods and compositions described herein is a lentiviral vector. Lentiviral vectors (LVs), a subset of retroviruses, transduce a wide range of dividing and non-dividing cell types with high efficiency, conferring stable, long-term expression of the transgene encoding the polypeptide or RNA. An overview of optimization strategies for packaging and transducing LVs is provided in Delenda, The Journal of Gene Medicine 6: S125 (2004), the disclosure of which is incorporated herein by reference.

The use of lentivirus-based gene transfer techniques relies on the in vitro production of recombinant lentiviral particles carrying a highly deleted viral genome in which the agent of interest is accommodated. In particular, the recombinant lentivirus are recovered through the in trans coexpression in a permissive cell line of (1) the packaging constructs, i.e., a vector expressing the Gag-Pol precursors together with Rev (alternatively expressed in trans); (2) a vector expressing an envelope receptor, generally of an heterologous nature; and (3) the transfer vector, consisting in the viral cDNA deprived of all open reading frames, but maintaining the sequences required for replication, encapsidation, and expression, in which the sequences to be expressed are inserted.

A LV used in the methods and compositions described herein may include one or more of a 5'-Long terminal repeat (LTR), HIV signal sequence, HIV Psi signal 5'-splice site (SD), delta-GAG element, Rev Responsive Element (RRE), 3'-splice site (SA), elongation factor (EF) 1-alpha promoter and 3'-self inactivating LTR (SIN-LTR). The lentiviral vector optionally includes a central polypurine tract (cPPT) and a woodchuck hepatitis virus post-transcriptional regulatory element (WPRE), as described in U.S. Pat. No. 6,136,597, the disclosure of which is incorporated herein by reference as it pertains to WPRE. The lentiviral vector may further include a pHR' backbone, which may include for example as provided below.

The Lentigen LV described in Lu et al., Journal of Gene Medicine 6:963 (2004) may be used to express the DNA molecules and/or transduce cells. A LV used in the methods and compositions described herein may a 5'-Long terminal repeat (LTR), HIV signal sequence, HIV Psi signal 5'-splice site (SD), delta-GAG element, Rev Responsive Element (RRE), 3'-splice site (SA), elongation factor (EF) 1-alpha promoter and 3'-self inactivating L TR (SIN-LTR). It will be readily apparent to one skilled in the art that optionally one or more of these regions is substituted with another region performing a similar function.

Enhancer elements can be used to increase expression of modified DNA molecules or increase the lentiviral integration efficiency. The LV used in the methods and compositions described herein may include a nef sequence. The LV used in the methods and compositions described herein may include a cPPT sequence which enhances vector integration. The cPPT acts as a second origin of the (+)-strand DNA synthesis and introduces a partial strand overlap in the middle of its native HIV genome. The introduction of the cPPT sequence in the transfer vector backbone strongly increased the nuclear transport and the total amount of genome integrated into the DNA of target cells. The LV used in the methods and compositions described herein may include a Woodchuck Posttranscriptional Regulatory Element (W PRE). The WPRE acts at the transcriptional level, by promoting nuclear export of transcripts and/or by increasing the efficiency of polyadenylation of the nascent transcript, thus increasing the total amount of mRNA in the cells. The addition of the WPRE to LV results in a substantial improvement in the level of expression from several different promoters, both in vitro and in vivo. The LV used in the methods and compositions described herein may include both a cPPT sequence and WPRE sequence. The vector may also include an IRES sequence that permits the expression of multiple polypeptides from a single promoter.

In addition to IRES sequences, other elements which permit expression of multiple polypeptides are useful. The vector used in the methods and compositions described herein may include multiple promoters that permit expression more than one polypeptide. The vector used in the methods and compositions described herein may include a protein cleavage site that allows expression of more than one polypeptide. Examples of protein cleavage sites that allow expression of more than one polypeptide are described in Klump et al., Gene Ther.; 8:811 (2001), Osborn et al., Molecular Therapy 12:569 (2005), Szymczak and Vignali, Expert Opin Biol Ther. 5:627 (2005), and Szymczak et al., Nat Biotechnol. 22:589 (2004), the disclosures of which are incorporated herein by reference as they pertain to protein cleavage sites that allow expression of more than one polypeptide. It will be readily apparent to one skilled in the art that other elements that permit expression of multiple polypeptides identified in the future are useful and may be utilized in the vectors suitable for use with the compositions and methods described herein.

The viral vectors (e.g., retroviral vectors, e.g., lentiviral vectors) may include a promoter operably coupled to the transgene encoding the polypeptide or the polynucleotide encoding the RNA to control expression. The promoter may be a ubiquitous promoter. Alternatively, the promoter may be a tissue specific promoter.

Methods of Use

The polypeptides described herein (e.g., polypeptides that include an ectonucleoside triphosphate diphosphohydrolase (E-NTPDase) and an NMPase, such as eN, ALP, or AP, such as the polypeptides of any one of SEQ ID NOs: 8-11 and variants thereof having at least 80% sequence identity thereto) may be used to hydrolyze a nucleotide triphosphate (NTP) or nucleotide diphosphate (NDP) to a nucleoside. The method includes providing a polypeptide as described herein and the NTP or NDP and allowing the polypeptide to hydrolyze the NTP or NDP to the nucleoside. The NTP may be adenosine 5' triphosphate (ATP). The NDP may be adenosine 5' diphosphate (ADP), and the nucleoside may be adenosine.

The polypeptide may be provided directly or may be provided, e.g., as a polynucleotide or a vector or cell comprising the same, e.g., as a delivery vehicle or as a gene therapy.

The polypeptides, polynucleotides, vectors, or cells described herein may be formulated into pharmaceutical compositions for administration to human subjects for the treatment of a disease or condition, such as a disease or condition related to inflammation.

The compositions and methods described herein may be used to reduce a level of inflammation, e.g., in a subject, such as a human, in need thereof. For example, the methods may decrease (e.g., by 1%, 2%, 3%, 4%, 5%, 10%, 20%, 30%, 40%, 50%, 60%, 70%, 80%, 90%, 95%, 97, 99%, or more) a level of inflammation as compared to a reference (e.g., the subject before onset of inflammation or a healthy subject without inflammation. For example, the inflammation may decrease by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% following administration of the composition. The level of inflammation may be measured e.g., by using a blood test for C-reactive protein (hs-CRP) in a subject.

The compositions described herein may be used for inhibiting or reducing (e.g., by 1%, 2%, 3%, 4%, 5%, 10%, 20%, 30%, 40%, 50%, 60%, 70%, 80%, 90%, 95%, 97, 99%, or more) platelet aggregation. Platelet aggregation can be measured by a Lumi-aggregometor (Chrono-Log, Havertown, PA) as described in Enjyoji et al. Nat Med 5: 1010-1017, 1999, which is hereby incorporated by reference. Platelets may be incubated at 37° C. and the percent light transmission can be measured, e.g., following administration of the polypeptide. The subject may be at risk of forming a blood clot, e.g., a pulmonary embolism.

The compositions described herein may be used to reduce (e.g., by 1%, 2%, 3%, 4%, 5%, 10%, 20%, 30%, 40%, 50%, or more, e.g., by about 0.1 mmHg, 0.2 mmHg, 0.3 mmHg, 0.4 mmHg, 0.5 mmHg, 1 mmHg, 2 mmHg, 3 mmHg, 4 mmHg, 5 mmHg, or more) blood pressure in a subject. Blood pressure may be measured by diastolic and/or systolic pressure or ambulatory blood pressure monitoring (ABPM), as would be well understood to one of skill in the art.

The method may be used to reduce vascular thrombosis and/or mechanical perturbation. The method may be used to treat ischemia.

In some embodiments, the compositions described herein may be used to reduce inflammation in a tissue injury (e.g., injury to the epidermis, arm, leg, torso, head, foot, hand, finger), e.g., as measured using a blood test for hs-CRP or by measuring a volume of swelling in the subject.

The method may be used to reduce (e.g., by 1%, 2%, 3%, 4%, 5%, 10%, 20%, 30%, 40%, 50%, 60%, 70%, 80%, 90%, 95%, 97, 99%, or more) hypoxia, e.g., as measured using pulse oximetry.

The method may be used to reduce apoptosis, e.g., as determined via flow cytometry or externalization of phosphatidylserine on the plasma membrane using fluorescent-tagged annexin V.

The compositions may be used to treat cancer. Cancers that may be treated with the compositions described herein, include, e.g., leukemia, lymphoma, liver cancer, bone cancer, lung cancer, brain cancer, bladder cancer, gastrointestinal cancer, breast cancer, cardiac cancer, cervical cancer, uterine cancer, head and neck cancer, gallbladder cancer, laryngeal cancer, lip and oral cavity cancer, ocular cancer, melanoma, pancreatic cancer, prostate cancer, colorectal cancer, testicular cancer, throat cancer, acute lymphoblastic leukemia (ALL), acute myeloid leukemia (AML), chronic lymphocytic leukemia (CLL), chronic myelogenous leukemia (CML), adrenocortical carcinoma, AIDS-related lymphoma, primary CNS lymphoma, anal cancer, appendix cancer, astrocytoma, atypical teratoid/rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, Langerhans cell histiocytosis, Hodgkin lymphoma, hypopharyngeal cancer, islet cell tumors, pancreatic neuroendocrine tumors, Wilms tumor and other childhood kidney tumors, Langerhans cell histiocytosis, small cell lung cancer, cutaneous T cell lymphoma, intraocular melanoma, Merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, non-Hodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, pleuropulmonary blastoma, primary peritoneal cancer, rectal cancer, retinoblastoma, rhabdomyosarcoma, salivary gland cancer, kaposi sarcoma, rhabdomyosarcoma, Sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, and Waldenström macroglobulinemia.

The method may be used to treat inflammation characterized by high levels of ATP and tissue damage and activation of immune responses.

The method may be used to treat an acute inflammatory disease, such as a cardiovascular or cerebrovascular illness associated with or linked to vascular endothelial and platelet activation with thrombosis. The method may be used to treat ischemia reperfusion injury. The method may be used to treat transplantation graft preservation and reperfusion, reperfusion injury to native organs (e.g., heart, brain, liver, and gut), and acute surgical and nonsurgical trauma.

The compositions and methods may be used to treat a pulmonary illness. The pulmonary illness may be, e.g., lung injury trauma, acute respiratory distress syndrome (ARDS), e.g., associated with a viral infection, such as that caused severe acute respiratory syndrome coronavirus 2 (SARS-CoV2), which leads to COVID-19. Other pulmonary illnesses include, e.g., pulmonary embolism, asthma, primary pulmonary hypertension, stroke, unstable angina, myocardial infarction, deep vein thrombosis (DVT), and pulmonary fibrosis.

The compositions and methods may be used to treat gastrointestinal and/or liver disease. The compositions may be used to treat an inflammatory bowel disease (IBD), such as Crohn's disease or ulcerative colitis. Other inflammatory diseases include, e.g., celiac disease, *Clostriudium difficile* and pseudomembranous colitis, mesentery ischemia, fatty liver disorders and non-alcoholic steatohepatitis, acute toxic liver injury (e.g., as with acetaminophen and mushroom poisoning), acute viral hepatitis, autoimmune hepatitis, decompensated cirrhosis, and fulminant liver failure. The compositions and methods may be used to treat acute renal failure, septicemia, and end-organ failure with purine starvation.

The compositions and methods may be used to treat a neurodegenerative disease, such as multiple sclerosis.

The compositions and methods may be used to treat rheumatological and autoimmune diseases, such as acute tophaceous gout, seropositive rheumatoid arthritis, juvenile rheumatoid arthritis, psoriasis, lupus, and dermatomyositis.

The compositions and methods may be used to treat acute diabetic ketoacidosis and metabolic perturbation. The compositions and methods may be used to treat pregnancy conditions, such as preeclampsia, toxemia, and acute fatty liver of pregnancy.

Disease and conditions that may be treated with the compositions and methods described herein are described in, e.g., Eltzschig et al. (*NEJM* 367:2322-2333, 2012), the disclosure of which is hereby incorporated by reference.

In some embodiments, the subject that is treated is monitored for therapeutic efficacy during a course of treatment. For example, a subject that is treated for a disease or condition (e.g., high blood pressure or inflammation, e.g., IBD) may be monitored for a reduction in severity or occurrence of symptoms. If the symptoms are not sufficiently reduced (e.g., beyond a predetermined threshold, e.g., 30% reduction, 20% reduction, 10% reduction, or less), the subject may be provided an increased dose (e.g., increased frequency or higher amount per dose). If the symptoms are sufficiently reduced to a desired level (e.g., 50% reduction, 60%, reduction, 70% reduction, or more), then the dosage may remain the same or may be decreased (e.g., decreased frequency or lower amount per dose). If the disease or condition is substantially resolved, the subject may discontinue treatment.

The subject may be monitored for progression or reduction of the disease, e.g., once per day, once every two days, once every three days, once every four days, once every five days, once every six days, once a week, once every two weeks, once every three weeks, once every month, once every two months, once every three months, once every six months, once every nine months, once per year, or longer.

Pharmaceutical Compositions

The polypeptides or polynucleotides, vectors, or cells comprising the same as described herein can be formulated as pharmaceutical compositions for administration to human subjects in a biologically compatible form suitable for administration in vivo.

The compositions described herein may be administered to a subject (e.g., a human) in a variety of forms depending on the selected route of administration, as will be understood by those skilled in the art. The compositions described herein may be administered, for example, by any route that allows the composition (e.g., the polypeptide or polynucleotide) to reach the target cells. The composition may be administered, for example, by oral, parenteral, intrathecal, intracerebroventricular, intraparenchymal, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, intracerebroventricular, intraparenchymal, rectal, and topical modes of administration. In one embodiment, the composition is administered via aero Parenteral administration may be by continuous infusion over a selected period of time. In some preferred embodiments, the compositions described herein are administered via inhalation.

Certain compositions described herein may be administered, e.g., by inhalation. Inhalation may be oral inhalation or nasal inhalation. An inhalable composition described herein may be provided as a liquid dosage form or dry powder dosage form. A dry powder composition may be, e.g., administered by inhalation as is or after reconstitution in a vehicle (e.g., saline (e.g., isotonic saline), phosphate-buffered saline, or water).

A composition described herein may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a composition described herein may be incorporated with an excipient and used in the form of ingestible tablets, buccal tablets, troches, capsules, elixirs, suspensions, syrups, and wafers. A composition described herein may also be administered parenterally. Solutions of a composition described herein can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2012, 22nd ed.) and in The United States Pharmacopeia: The National Formulary (USP 41 NF 36), published in 2018. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions suitable for buccal or sublingual administration include tablets, lozenges, and pastilles, where the active ingredient is formulated with a carrier, such as sugar, acacia, tragacanth, gelatin, and glycerin. Compositions for rectal administration are conveniently in the form of suppositories containing a conventional suppository base, such as cocoa butter.

The composition described herein may be administered to an animal, e.g., a human, alone or in combination with pharmaceutically acceptable carriers, as noted herein, the proportion of which is determined by the solubility and chemical nature of the composition, chosen route of administration, and standard pharmaceutical practice.

In general, the dosage of a pharmaceutical composition or the active agent in a pharmaceutical composition may be in the range of from about 1 pg to about 10 g (e.g., 1 pg-10 pg, e.g., 2 pg, 3 pg, 4 pg, 5 pg, 6 pg, 7 pg, 8 pg, 9 pg, 10 pg, e.g., 10 pg-100 pg, e.g., 20 pg, 30 pg, 40 pg, 50 pg, 60 pg, 70 pg, 80 pg, 90 pg, 100 pg, e.g., 100 pg-1 ng, e.g., 200 pg, 300 pg, 400 pg, 500 pg, 600 pg, 700 pg, 800 pg, 900 pg, 1 ng, e.g., 1 ng-10 ng, e.g, 2 ng, 3 ng, 4 ng, 5 ng, 6 ng, 7 ng, 8 ng, 9 ng, 10 ng, e.g., 10 ng-100 ng, e.g., 20 ng, 30 ng, 40 ng, 50 ng, 60 ng, 70 ng, 80 ng, 90 ng, 100 ng, e.g., 100 ng-1 pg, e.g., 200 ng, 300 ng, 400 ng, 500 ng, 600 ng, 700 ng, 800 ng, 900 ng, 1 μg, e.g., 1-10 μg, e.g., 1 μg, 2 μg, 3 μg, 4 μg, 5 μg, 6 μg, 7 μg, 8 μg, 9 μg, 10 μg, e.g., 10 μg-100 μg, e.g., 20 μg, 30 μg, 40 μg, 50 μg, 60 μg, 70 μg, 80 μg, 90 μg, 100 μg, e.g., 100 μg-1 mg, e.g., 200 μg, 300 μg, 400 pg, 500 μg, 600 μg, 700 μg, 800 μg, 900 μg, 1 mg, e.g., 1 mg-10 mg, e.g., 2 mg, 3 mg, 4 mg, 5 mg, 6 mg, 7 mg, 8 mg, 9 mg, 10 mg, e.g., 10 mg-100 mg, e.g., 20 mg, 30 mg, 40 mg, 50 mg, 60 mg, 70 mg, 80 mg, 90 mg, 100 mg, e.g., 100 mg-1 g, e.g., 200 mg, 300 mg, 400 mg, 500 mg, 600 mg, 700 mg, 800 mg, 900 mg, 1 g, e.g., 1 g-10 g, e.g., 2 g, 3 g, 4 g, 5 g, 6 g, 7 g, 8 g, 9 g, 10 g).

The pharmaceutical composition may also be administered as in a unit dose form or as a dose per mass or weight of the patient from about 0.01 mg/kg to about 100 mg/kg (e.g., 0.01-0.1 mg/kg, e.g., 0.02 0.03 mg/kg, 0.04 mg/kg, 0.05 mg/kg, 0.06 mg/kg, 0.07 mg/kg, 0.08 mg/kg, 0.09 mg/kg, 0.1 mg/kg, e.g., 0.1-1 mg/kg, e.g., 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, e.g., 1-10 mg/kg, e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, e.g., 10-100 mg/kg, e.g., 20 mg/kg, 30 mg/kg, 40 mg/kg, 50 mg/kg, 60 mg/kg, 70 mg/kg, 80 mg/kg, 90 mg/kg, 100 mg/kg). The dose may also be administered as a dose per mass or weight of the patient per unit day (e.g., 0.1-10 mg/kg/day).

The dosage of the compositions (e.g., a composition including a polypeptide) described herein, can vary depending on many factors, such as the pharmacodynamic properties of the polypeptide, the mode of administration, the age, health, and weight of the recipient, the nature and extent of the symptoms, the frequency of the treatment, and the type of concurrent treatment, if any, and the clearance rate of the composition in the animal to be treated. The compositions described herein may be administered initially in a suitable dosage that may be adjusted as required, depending on the clinical response. In some embodiments, the dosage of a composition (e.g., a composition including a polypeptide) is a prophylactically or a therapeutically effective amount. Furthermore, it is understood that all dosages may be continuously given or divided into dosages given per a given time frame. The composition can be administered, for example, every hour, day, week, month, or year. In some embodiments, the composition may be administered continuously or systemically.

The pharmaceutical compositions described herein (e.g., containing a polypeptide, polynucleotide, vector, or cell described herein) may be provided in a kit that includes the pharmaceutical composition (e.g., in a container) and instructions for use thereof. The kit may contain one or more containers, in which each container contains a different composition of the invention (e.g., one container with a polypeptide of the invention and one container with a polynucleotide of the invention). The instructions enclosed with the kit may be used to instruct a user to perform a method as described herein.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1: Preparation and Testing of a CD39 and CD73 Bifunctional Fusion Protein Materials and Methods Chemicals Adenosine-5'-triphosphate disodium, Adenosine-5'-diphosphate disodium, Adenosine-5'-monophosphate disodium, Guanosine-5'-triphosphate disodium, Guanosine 5'-monophosphate disodium, Uridine-5'-triphosphate trisodium, Uridine 5'-diphosphate disodium, and Uridine 5'-monophosphate disodium, Guanosine 5'-diphosphate sodium, TRAP6, Chrono-log, Collagen P/N 385, malachite green hydrochloride, ammonium molybdate, Polyoxyethylene 10 Lauryl Ether, and sodium citrate·2H2O were purchased from Millipore Sigma (St. Louis, Mo.).

Expression Construct

DNA fragments, encoding human CD39 (Thr45-Thr483; GenBank #: NP_001091645.1), human CD73 (Trp27-Ser549; GenBank #:NP_002517.1), human testicular and thymus alkaline phosphatase (ALP, Ile20-Thr502; GenBank #:NP_112603.2), human prostatic acid phosphatase (HAP, Lys33-Asp386; GenBank #:NM_001099.5) and human immunoglobulin yl Fc fragment (CH23, constant region starting with Gly236, the numbering of the EU amino acid sequence), were gene-synthesized by Blue Heron Biotech (Bothell, Wash.) and GenScript Biotech (Piscataway, N.J.). Corresponding full-length DNA fragments with an N-terminal signal sequence of glycoprotein 1 b alpha chain (MPLLLLLLLLPSPLHG; SEQ ID NO: 4) and a Gly4 linker in between each protein domain were assembled by polymerase chain reaction, and cloned into a human CMV promoter mammalian expression vector with EcoRI and BamHI (pEZ1002, HAPCH23; pEZ1006, ALPCH23; pEZ1007, CD73CH23CD39; pEZ1009, CD39CH23CD73; pEZ1010, CD39CD73CH23; pEZ1011, CD73CH23CD39; pWZ1013, CD73CH23; pWZ1014, CD39CH23). All constructs were confirmed by DNA sequencing.

Cell Culture and Transfection

Human embryonic kidney 293 (Expi293F) were grown and maintained in a humidified incubator with 5% $CO_2$ at 37° C. in Expi293™ medium (Thermo Fisher, Waltham, Mass.). DNA transfection procedures in Expi293F cells were followed as described in ThermoFisher manufacturer's protocols. Briefly, DNA and lipofectamine complex were inoculated with $3.0\times10^6$/ml cells and expression enhancers were added 24 hrs post-transfection. Conditioned media were harvested at Day 4 and filtered with 0.2μ filters.

Protein Purification 5 ml of Protein-A column (GE Healthcare, Piscataway, N.J.) pre-equilibrated with 50 mM Tris, 150 mM NaCl, pH 7.5 (PBS) was loaded with conditioned medium and washed with 10 column volumes (CV) of PBS, before the protein was eluted using 100% step of 150 mM Glycine pH3.5 in PBS. The protein was dialyzed overnight against 1000-fold 50 mM Tris, 150 mM NaCl, pH 7.5 (TBS) buffer overnight. Protein samples were pooled concentrated to 0.5-1.0 mg/mL using a 10 kDa MWCO centrifugal device.

Colorimetrical NTPDase and NMPase Assays

The colorimetrical assay was performed as previously described (Llinas et al. *J. Mol. Biol.* 350: 441-451, 2005; Zhong et al. Purinergic Signal 13: 601-609, 2017). Essentially, 0.045% malachite green hydrochloride (MG), 4.2% ammonium molybdate in 4N HCl (AM), 4% solution of C12E10 (Polyoxyethylene 10 Lauryl Ether, Millipore Sigma) (CE), and 34% sodium citrate·$2H_2O$ (w/v), were prepared. Prior to the assay, MG and AM were mixed in 3:1 ratio, incubated for at least 20 min, and filtered through 0.2μ membrane. 0.1 ml of CE solution was added to every 5 ml of MG/AG solution. The NTPDase buffer contained 20 mM Tris-HCl, pH7.5, 120 mM NaCl, 5 mM KCl, 0.5 mM EDTA. 5 mM $CaCl_2$) was added to calcium-plus reaction buffer. During the NTPDase assay, CD39 fusions or bifunctional samples (100 ng) were added to initiate the reaction at 37° C. for 10 min. 0.8 ml MG/AG/CE solution and 100 ul citrate were added sequentially to stop the reactions. A660 reading was measured by pre-blanked with 1 ml MG/AG/CE buffer. A660 reading with $CaCl_2$) subtracted by A660 without divalent cation was converted phosphate standard curve. For NMPase assay, CD73 fusions or bifunctional samples' A660 readings were subtracted by those without enzyme. For alkaline phosphatase and acid phosphatase assays, ALP and HAP samples (200 ng) were used. A660 readings were subtracted by those without enzymes. For reaction buffer pH5.8, 200 mM Histidine, pH5.8, 120 mM NaCl, 5 mM KCl, 0.5 mM EDTA was used. For reaction buffer pH9.0, 200 mM N-cyclohexyl-2-aminoethanesulfonic acid, 120 mM NaCl, 5 mM KCl, 0.5 mM EDTA was used.

High Performance Liquid Chromatography (HPLC)

Perchloride acid (PCA)-treated samples were neutralized with 0.4 M $K_2HPO_4$ (Sigma-Aldrich, St. Louis, Mo.) and ATP, ADP, AMP and adenosine concentrations were analyzed with an Agilent 1260 Infinity HPLC system (Agilent Technologies, Santa Clara, Calif.) equipped with a G1312B binary pump, a G1367C high performance autosampler and a G1314C Variable Wavelength Detector VL+set at 254 nm. Nucleotides were separated by ion-pair reversed-phase chromatography using an Atlantis $dC_{18}$ column (3 mm×150 mm, particle size 3 μm; Waters Corporation, Milford, Mass.). The samples were loaded on the column equilibrated with buffer A (0.1 M $KH_2PO_4$, 4 mM tetrabutylammonium hydrogen sulfate, pH 6). The mobile phase developed linearly from 0 to 100% buffer B (70% buffer A/30% methanol) during the first 13 min and remained isocratic at 100% buffer B for 15 min. Subsequently, the column was re-equilibrated with buffer A for 7 minutes. The flow rate was 0.5 ml/min. Adenosine, AMP, ADP and ATP were identified by their retention times and concentrations were calculated using known standards run in parallel.

Analysis of Platelet Activation In Vitro

Platelet aggregation was measured by a Lumi-aggregometor (Chrono-Log, Havertown, PA) as described previously (Enjyoji et al. Nat Med 5: 1010-1017, 1999). Essentially, ~0.3 m of platelets were incubated at 37° C. and the percent light transmission was measured. Platelet agonists were tested at final concentrations of 2 μg/ml collagen or 12.5 nM Trap6. For bifunctional enzyme treatment of platelets, various amount of the protein was added as indicated.

Results

Production of CD39 and CD73 Bifunctional Fusions as Well as Other Control Fusion Proteins To design a novel bifunctional enzyme that can hydrolyze tri-/diphosphate nucleotides all way down to nucleoside products (FIG. 1A), the ectodomain of human CD39 (Thr45-Thr483), with the amino acid boundaries defined by structural modeling on rat CD39 structures, was fused to either N- or C-termini of the ectodomain of human CD73 (Trp27-Ser549), with amino acid boundaries defined by structural modeling on human CD73 structure (constructs 2 and 4, respectively of FIG. 1A). The ECD of CD39 or CD73 was then fused to either N- or C-termini of the $IgG_1$ Fc. These protein domains were connected with Gly4 linkers. The Fc domain fusion could not only allow feasible purification strategy with protein-A resin but also enable FcRn binding to extend in vivo protein half-life in circulation.

To generate the control fusion proteins (FIG. 1A), CD39-ECD-Fc Fusion (Thr45-Thr483, CD39CH23), CD73-ECD-Fc fusion (Trp27-Ser549, CD73CH23), human alkaline phosphatase ECD-Fc fusion (Ile20-Thr502, ALPCH23), and human acid phosphatase ECD-Fc (Lys33-Asp386, HAPCH23), were also generated by fusing to N-terminus of IgG1 Fc with a Gly4 linker in between. It has been reported that both alkaline phosphatase and acid phosphatase had activities towards tri/diphosphate nucleotides as well as monophosphate nucleotides, but they haven't been compared with each other or with other ectonucleotidases.

Figure 1B:
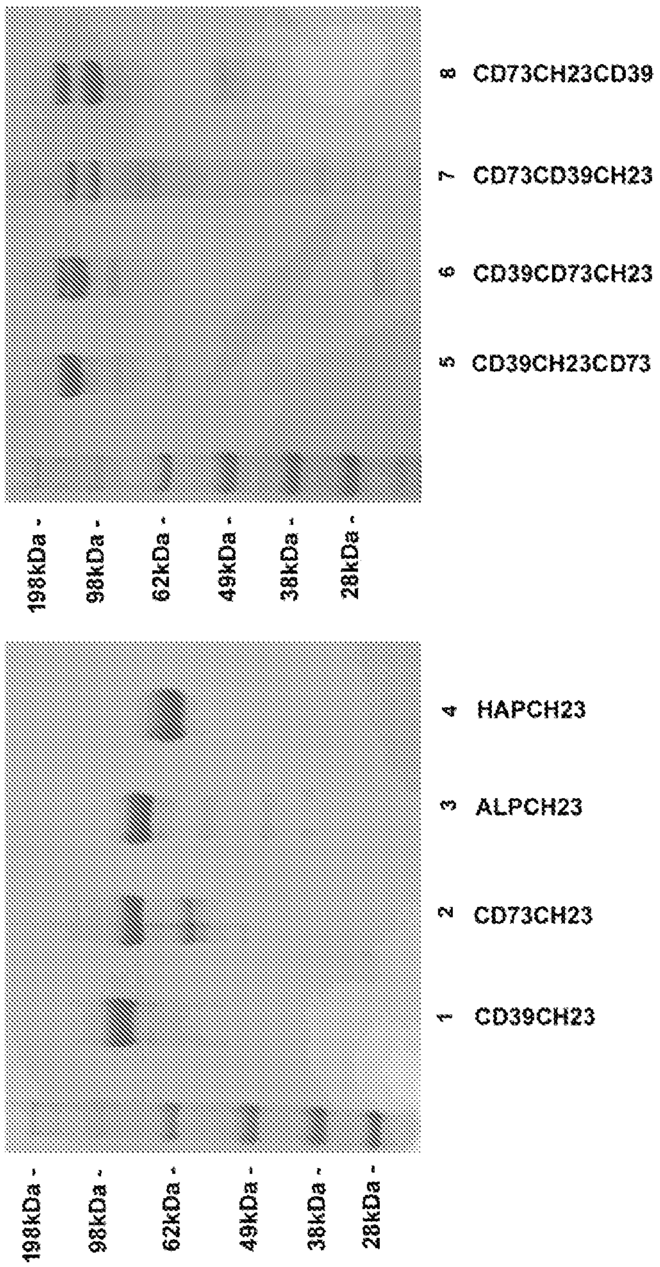
FIG. 1B is a set of SDS-PAGE gels showing purification of the eight constructs. Each construct was transfected into Expi293F cells. Chimeric recombinant proteins, secreted into conditioned media, were purified, and the purified protein samples were analyzed by SDS-PAGE.
Figure 2A:
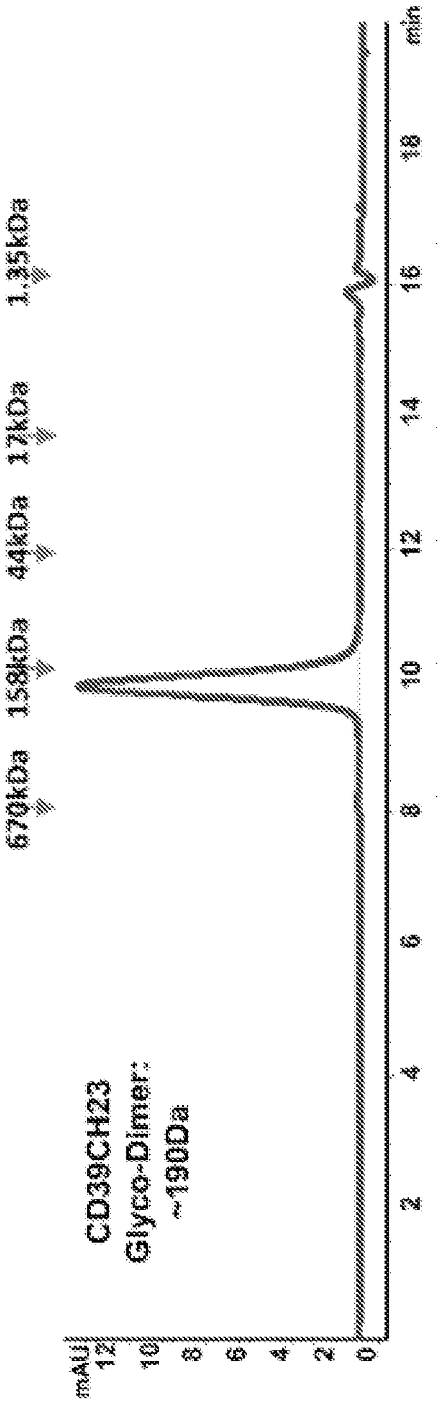
FIGS. 2A-2H are a set of size-exclusion chromatography (SEC) chromatograms showing CD39-CD73 bifunctional fusions and the control Fc fusion proteins analyzed by size-exclusion chromatography. Gel filtration standard components (BioRad) are Vitamin B12 (1.36 kDa), Myoglobin (17 kDa), Ovalbumin (44 kDa), γ-globulin (158 kDa), and Thyroglobulin (670 kDa).
Figure 2B:
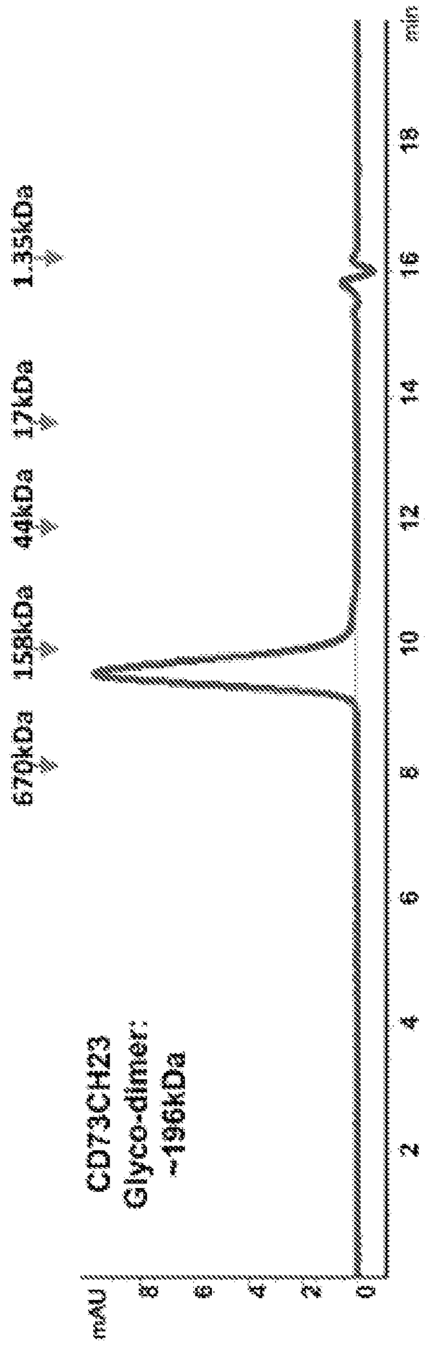
Figure 2C:
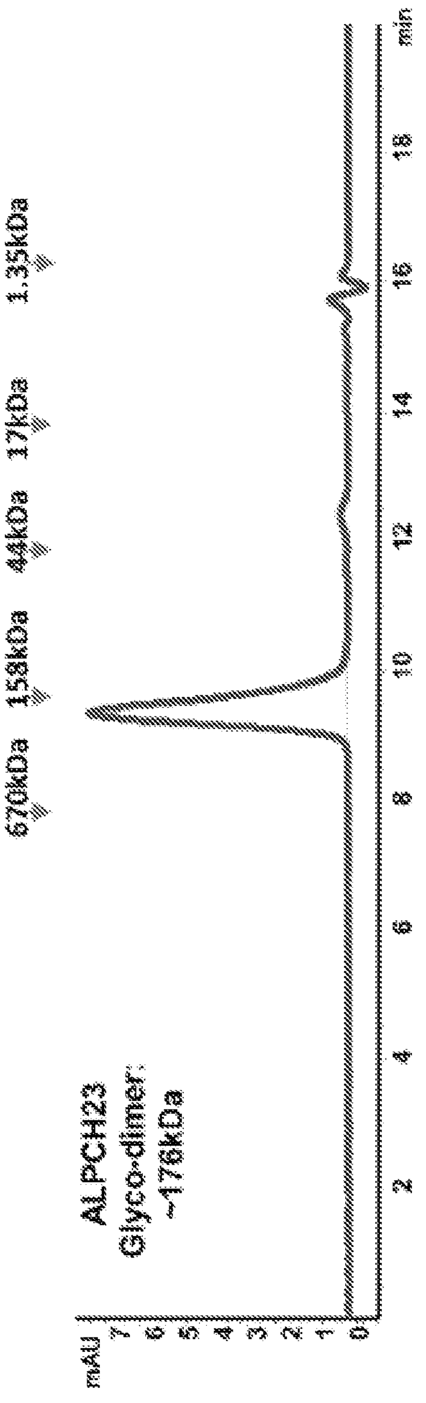
Figure 2D:
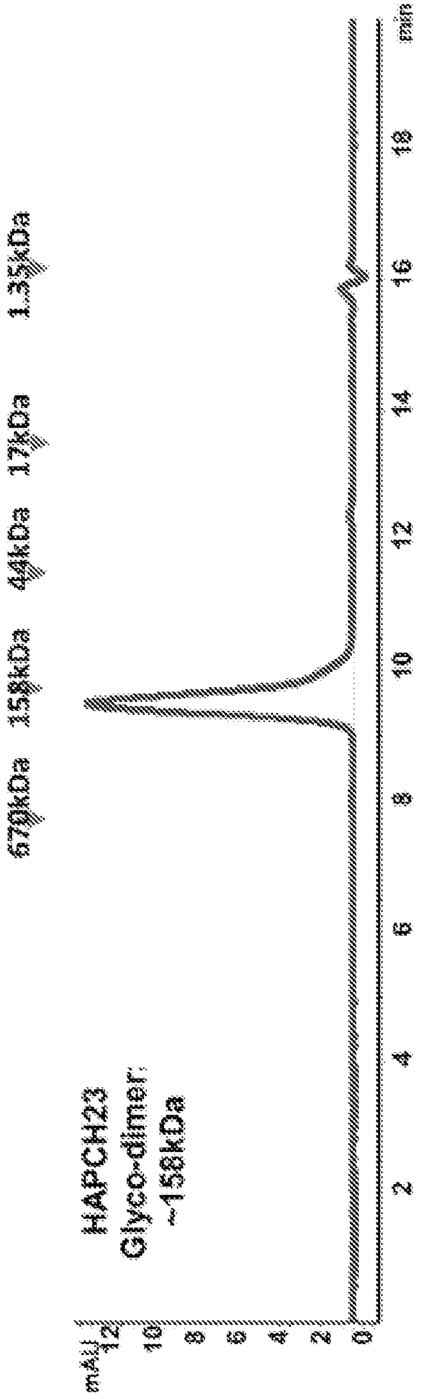
Figure 2E:
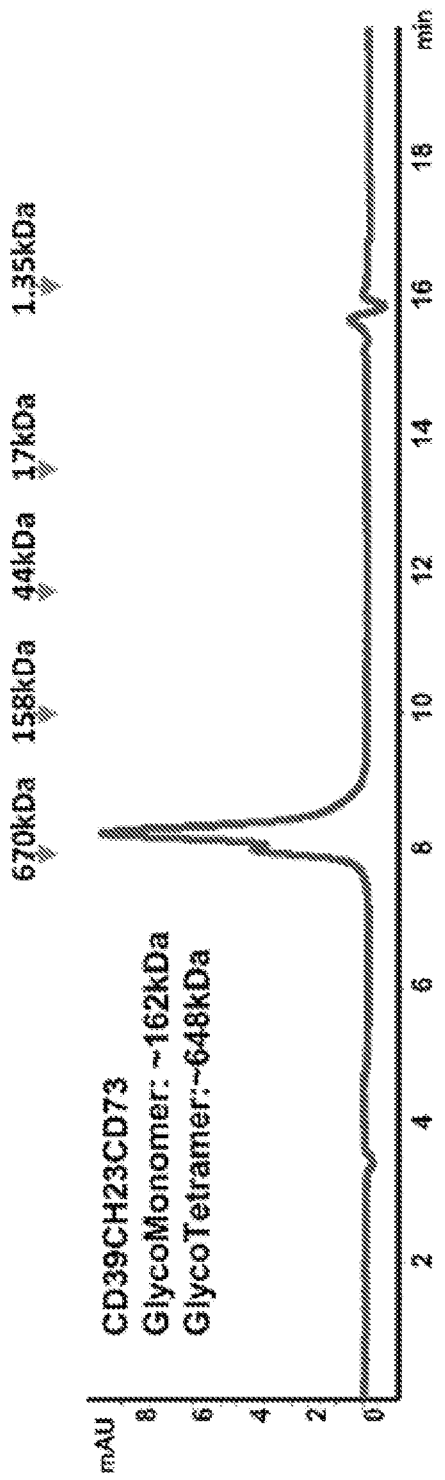
Figure 2F:
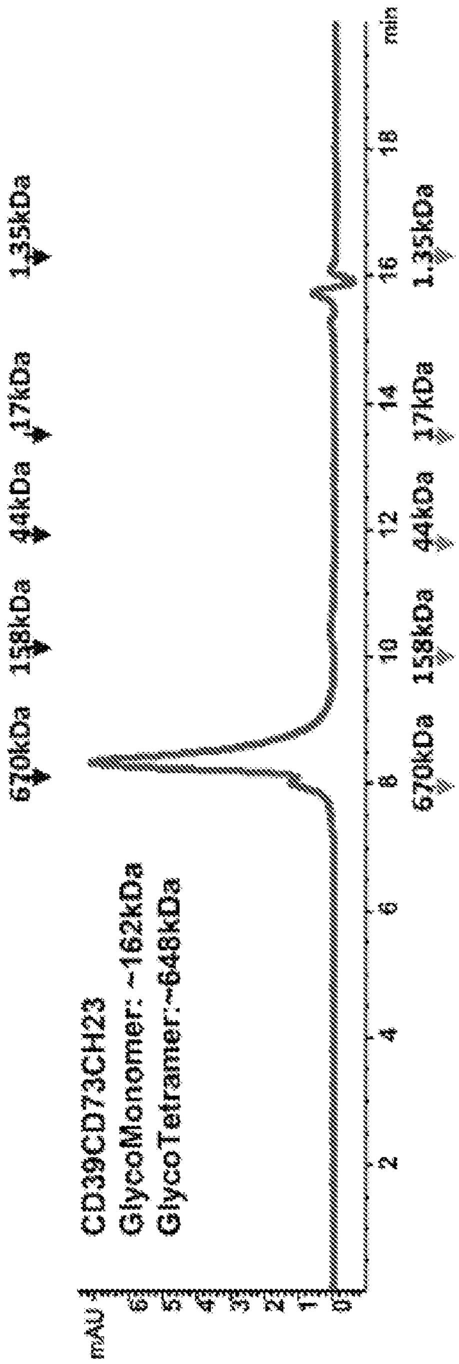
Figure 2G:
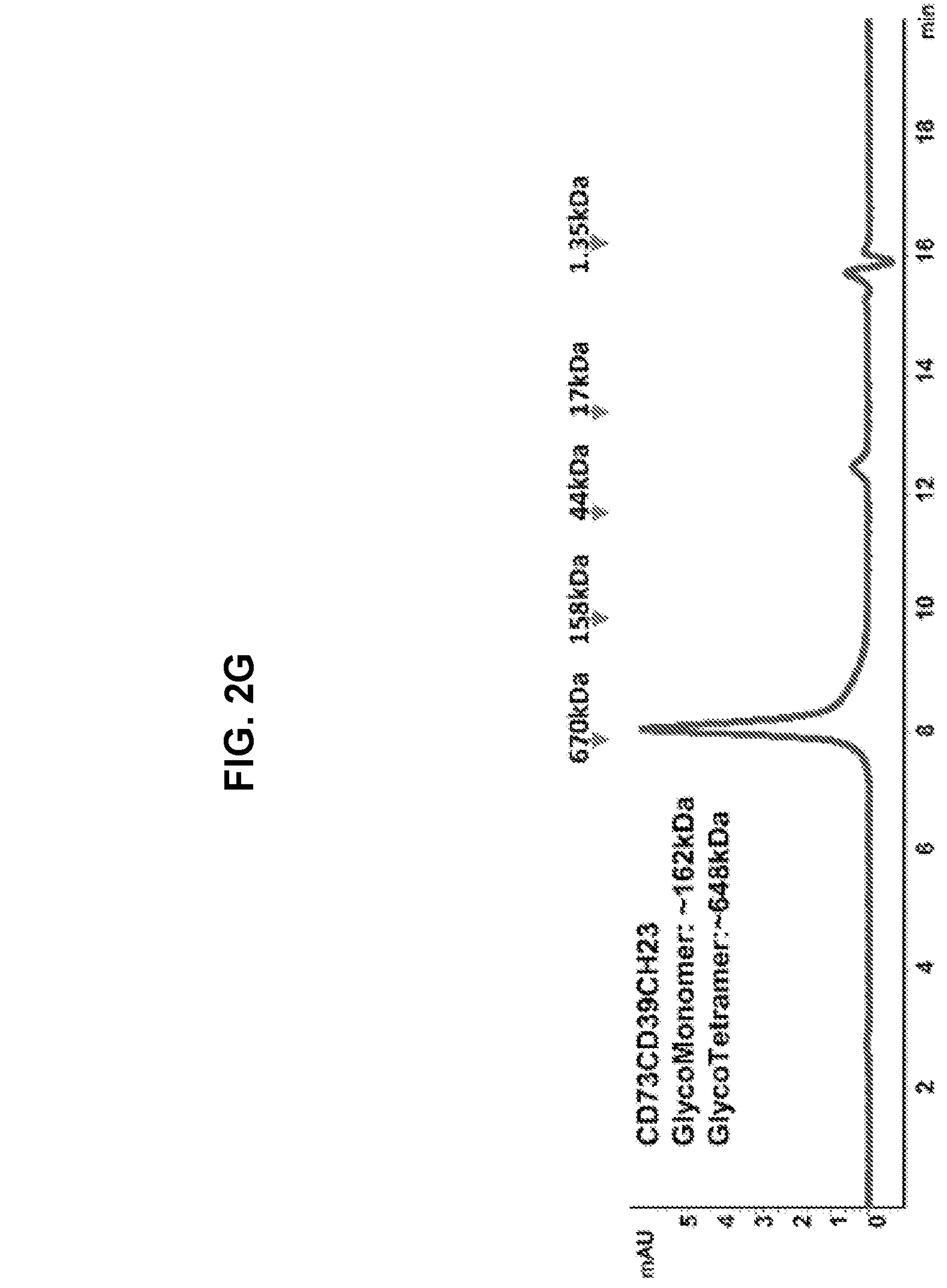
Figure 2H:
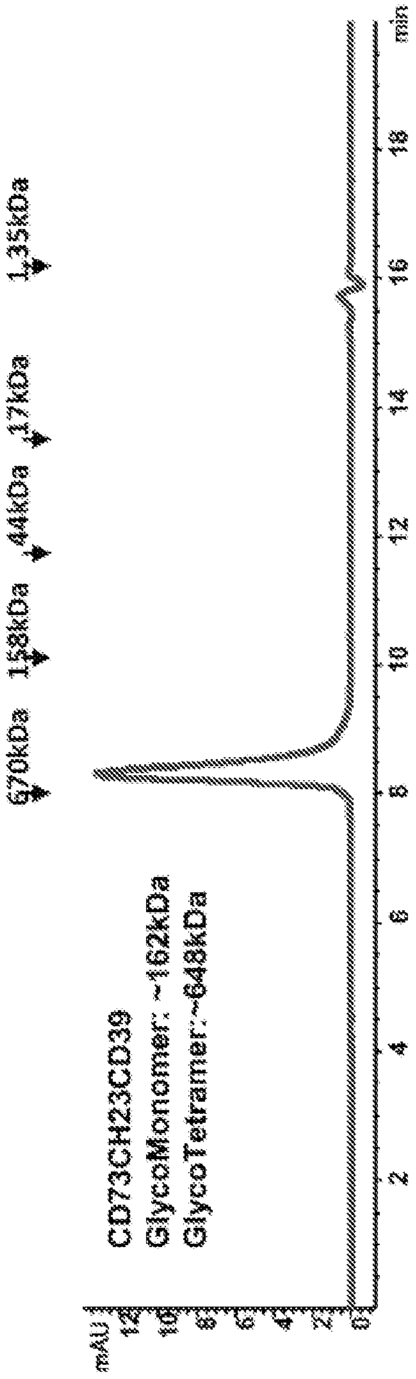

The resulting constructs above were transiently transfected into Expi293F cells for protein expression. The chimeric recombinant proteins, secreted into conditioned media, were purified as described in Materials and Methods. As shown in SDS-PAGE of FIG. 1B, control fusion proteins migrated as expected. CD39CH23 (lane 1) migrated around 95 kDa (Expected aglycosylated MW: 74 kDa; glycosylated MW: ~95.2 kDa). CD73CH23 (lane 2) migrated around 90 kDa (Expected aglycosylated MW:81.9 kDa; glycosylated MW: ~98 kDa). ALPCH23 (lane 3) migrated around 85 kDa (Expected aglycosylated MW: 76.5 kDa; glycosylated MW: ~88 kDa). HAPCH23 (lane 4) migrates around 70 kDa (Expected aglycosylated MW:65 kDa; glycosylated MW: ~79 kDa). CD39CH23 and HAPCH23 were homogeneous single band in SDS-PAGE, whereas minor low-molecular-weight species were detected for CD73CH23 and ALPCH23. For bifunctional fusions, CD39CH23CD39 (lane 5) migrated as a homogeneous 160 kDa-protein band (Expected aglycosylated MW:132.2 kDa; glycosylated MW: ~162 kDa). CD39CD73CH23 and CD73CH23CD39 contained the expected 160 kDa-band and one slightly smaller protein species (lanes 6 and 8). Significant degradation products were detected for CD73CD39CH23 (lane 7).

When the fusion proteins were analyzed in size exclusion chromatography (FIGS. 2A-2H), CD39CH23, CD73CH23, ALPCH23, and HAPCH23 were eluted slightly earlier (larger) than bovine γ-globulin marker (158 kDa), consistent with dimer species (FIGS. 2A-2D). All four bifunctional fusions were eluted slightly later (smaller) than Thyroglobulin (670 kDa), consistent with tetramer species (FIGS. 2E-2H). They could be a dimer of Fc dimer as CD73 is a homodimer.

Enzymatic Characterization of Bifunctional Fusions and Control Proteins

Figure 3A:
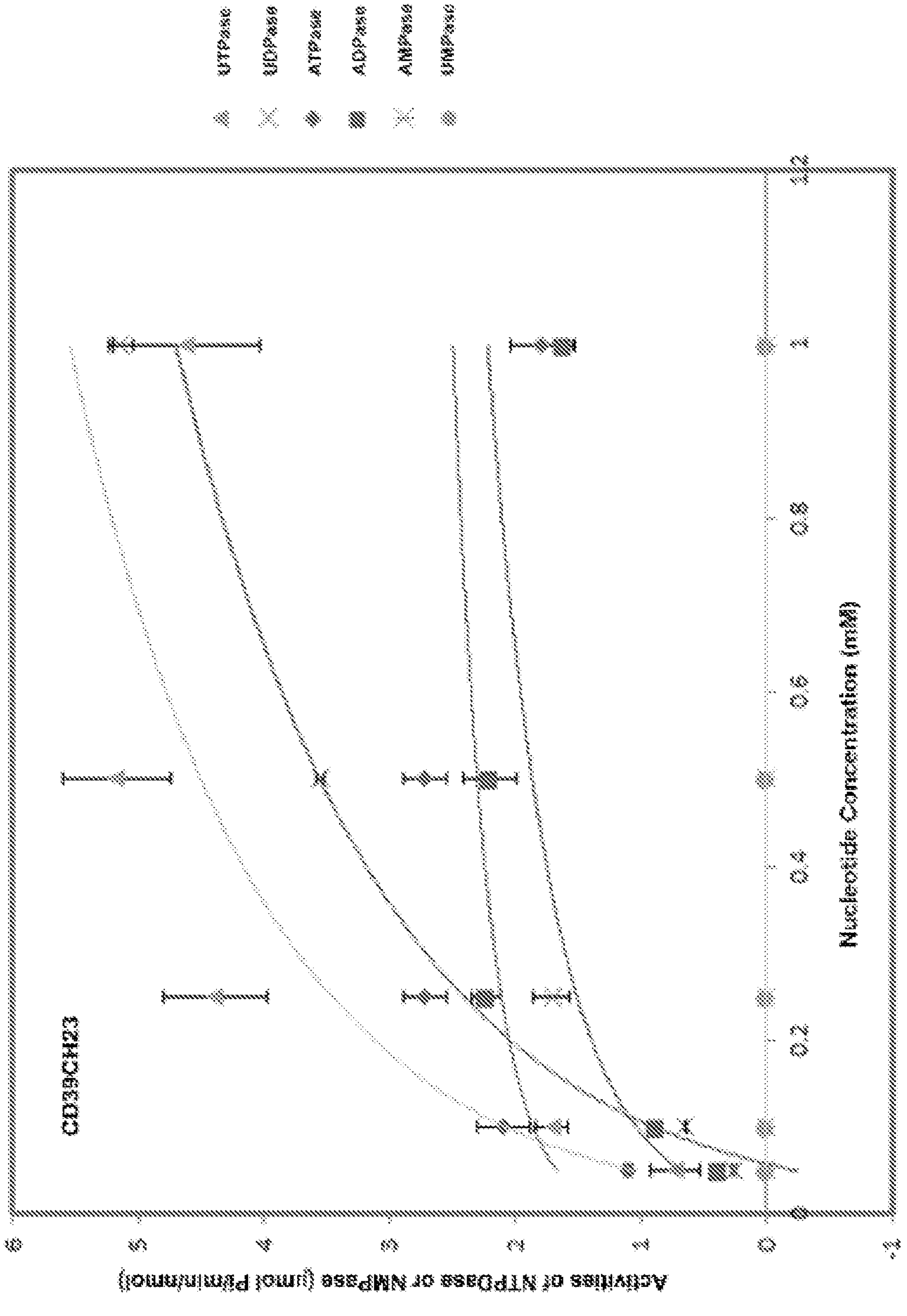
FIGS. 3A-3F are a set of graphs showing enzymatic characterization of CD39CH23 and CD73CH23. CD39CH23, CD73CH23 or a mixture thereof were respectively measured for NTPDase and NMPase activities. The error bars at each data point were calculated from triplicated experiments.
Figure 3B:
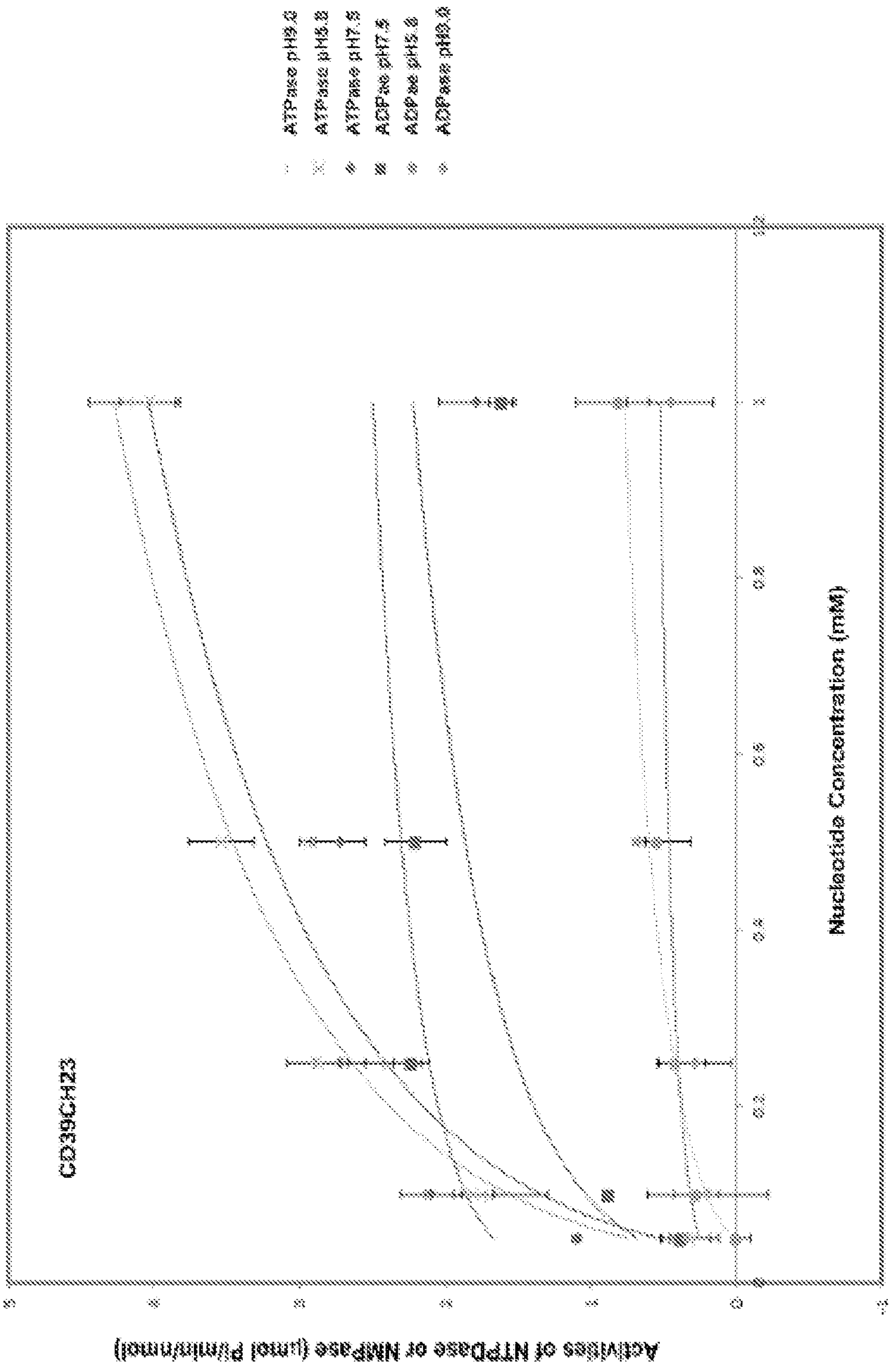
Figure 3C:
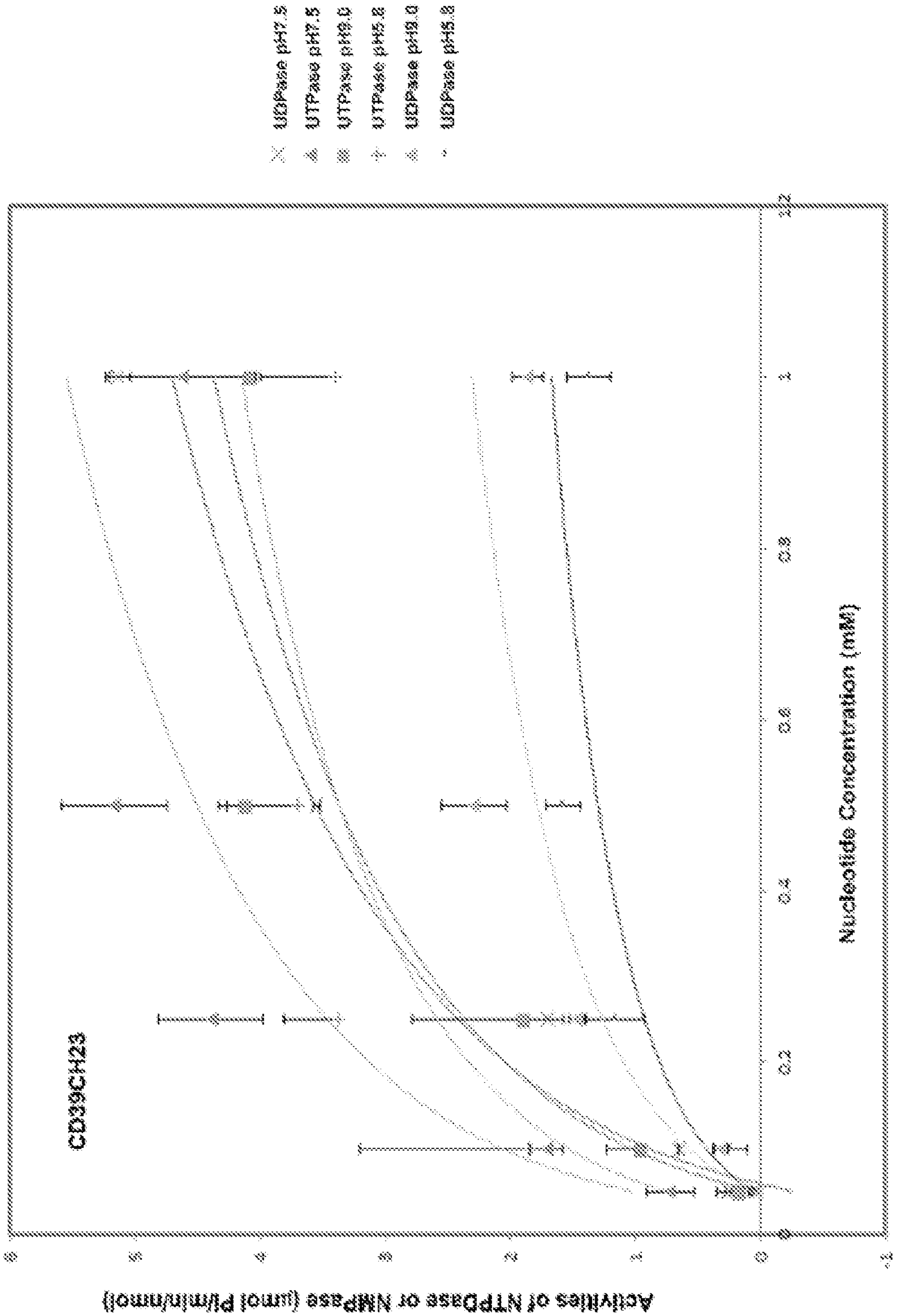

Next, we set out to determine the enzymatic activities of the purified fusion proteins with colorimetrical functional assay commonly used for NTPDase enzymes. As shown in FIG. 3A and Table 1, CD39CH23 fusion exhibited the activities of ATPase (Km 0.037 mM, Vmax 2.57 μmol/nmol/min), ADPase (Km 0.11 mM, Vmax 2.34 μmol/nmol/min), UTPase (Km 0.18 mM, Vmax 6.26 μmol/nmol/min), and UDPase (Km 1.51 mM, Vmax 13.13 μmol/nmol/min), but no NMPase activity. As shown in FIG. 3B and Table 1, CD39CH23's ATPase Activity was higher at acidic pH5.8 (Km 0.21 mM, Vmax 5.02 μmol/nmol/min) or alkaline pH9.0 (Km 0.31 mM, Vmax 5.24 μmol/nmol/min) condition than that in physiological condition (pH7.5), whereas its ADPase was lower in both conditions than in physiological pH. In contrast, as shown in FIG. 3C and Table 1, CD39CH23's UDPase activity was lower at acidic pH (Km 0.31 mM, Vmax 2.09 μmol/nmol/min) or alkaline pH (Km 0.33 mM, Vmax 2.93 μmol/nmol/min), than at neutral pH, while its UTPase Activity was not affected significantly by pH changes (pH5.8: Km 0.16 mM, Vmax 4.53 μmol/nmol/min; pH9.0: Km 0.52 mM, Vmax 6.75 μmol/nmol/min). These data indicate that the bifunctional fusion proteins retain their activities under acid and alkaline conditions.

TABLE 1

Vmax and Km of CD39CH23 at various pHs for NTPDase and NMPase activities.

| CD39CH23 | Km (mM) | Vmax (μmol Pi/nmol/min) |
|---|---|---|
| ATPase (pH 7.5) | 0.037 | 2.57 |
| UTPase (pH 7.5) | 0.18 | 6.26 |
| ADPase (pH 7.5) | 0.11 | 2.34 |
| UDPase (pH 7.5) | 1.51 | 13.13 |
| AMPase (pH 7.5) | 0 | 0 |
| UMPase (pH 7.5) | 0 | 0 |
| ATPase (pH 5.8) | 0.21 | 5.02 |
| ATPase (pH 9.0) | 0.31 | 5.24 |
| ADPase (pH 5.8) | 0.52 | 1.20 |
| ADPase (pH 9.0) | 0.084 | 0.56 |
| UTPase (pH 5.8) | 0.16 | 4.53 |
| UTPase (pH 9.0) | 0.52 | 6.75 |
| UDPase (pH 5.8) | 0.31 | 2.09 |
| UDPase (pH 9.0) | 0.33 | 2.93 |

Figure 3D:
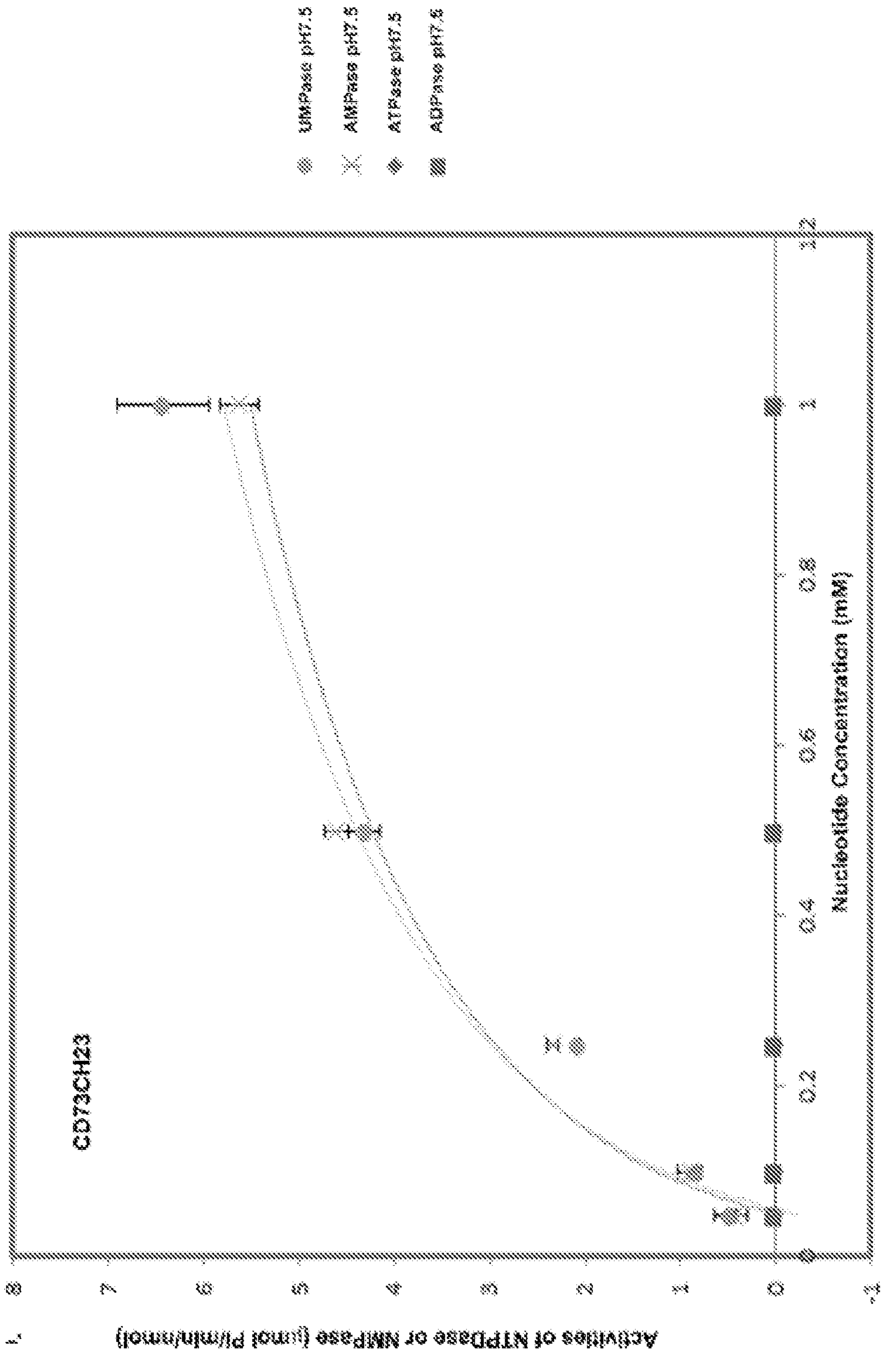
Figure 3E:
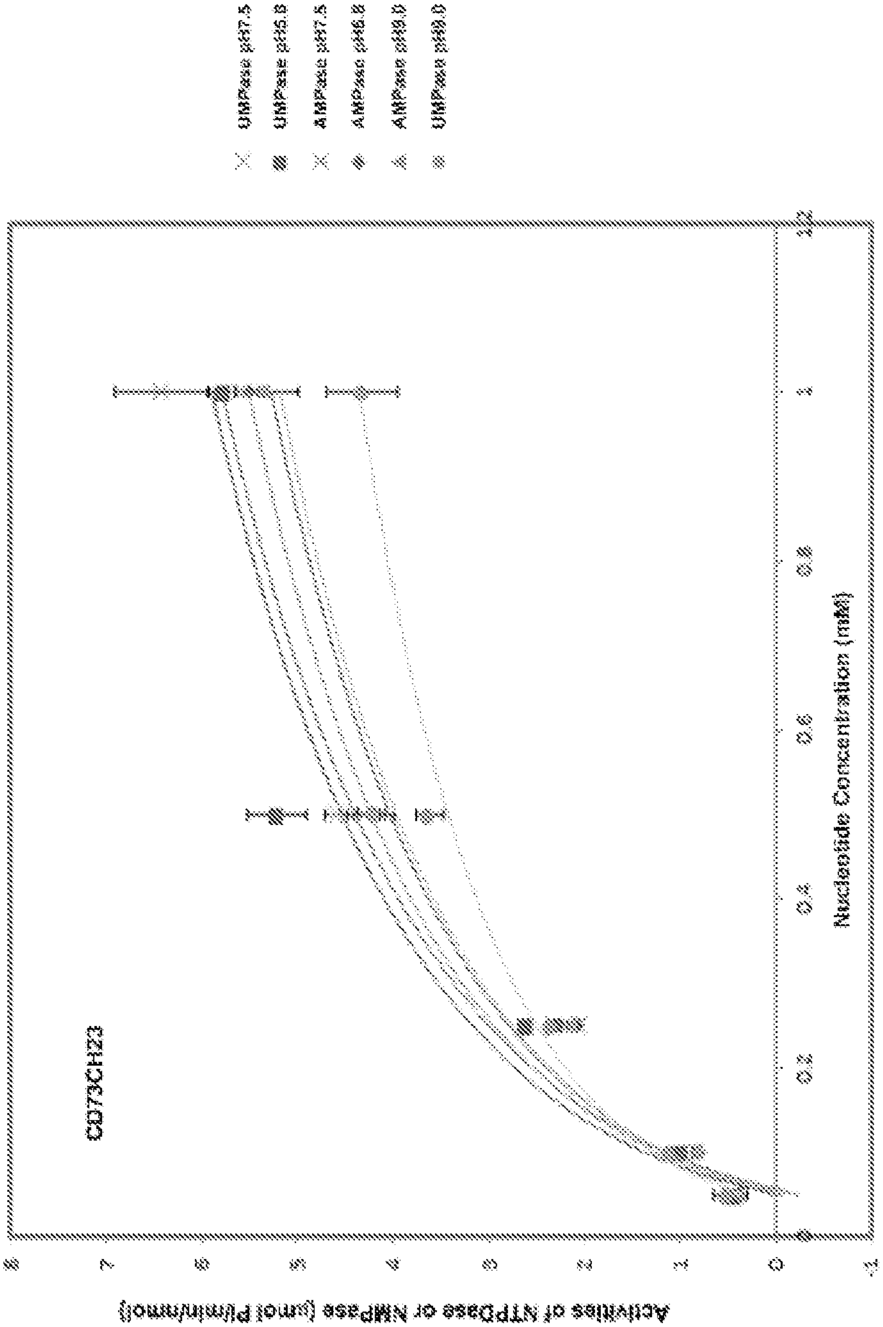

As shown in FIG. 3D and Table 2, human CD73CH23 fusion at physiological pH (pH7.5) possessed robust AMPase (Km 0.77 mM, Vmax 10.32 μmol/nmol/min) and UMPase activities (Km 1.57 mM, Vmax 16.73 μmol/nmol/min), but no ATPDase activity. As shown in FIG. 3E and Table 2, CD73CH23's NMPase activity is less affected by acidic or alkaline pH values. When CD39CH23 and CD73CH23 were mixed together in equal molar, the mixture had the activities of both NTPDase and NMPase (FIG. 3F, Table 3), reflecting the contributions of two different ectonucleotidases.

TABLE 2

Vmax and Km of CD73CH23 at various pHs for NTPDase and NMPase activities.

| CD73CH23 | Km (mM) | Vmax (μmol Pi/nmol/min) |
|---|---|---|
| AMPase (pH 7.5) | 0.77 | 10.32 |
| UMPase (pH 7.5) | 1.57 | 16.73 |
| ATPase (pH 7.5) | 0 | 0 |
| ADPase (pH 7.5) | 0 | 0 |
| AMPase (pH 5.8) | 0.89 | 10.69 |
| AMPase (pH 9.0) | 0.85 | 10.24 |
| UMPase (pH 5.8) | 0.63 | 9.94 |
| UMPase (pH 9.0) | 0.41 | 6.25 |

TABLE 3

Vmax and Km of the mixture of CD39CH23 and CD73CH23 at various pHs for NTPDase and NMPase activities.

| CD39CH23 + CD73CH23 | Km (mM) | Vmax (μmol Pi/nmol/min) |
|---|---|---|
| ATPase (pH 7.5) | 0.062 | 1.97 |
| ADPase (pH 7.5) | 0.074 | 1.82 |
| AMPase (pH 7.5) | 0.51 | 3.40 |
| ATPase (pH 5.8) | 0.13 | 1.62 |
| ADPase (pH 5.8) | 0.04 | 0.44 |
| AMPase (pH 5.8) | 0.52 | 3.46 |
| ATPase (pH 9.0) | 0.164 | 4.42 |
| ADPase (pH 9.0) | 0.098 | 2.40 |
| AMPase (pH 9.0) | 0.69 | 3.92 |

Figure 4A:
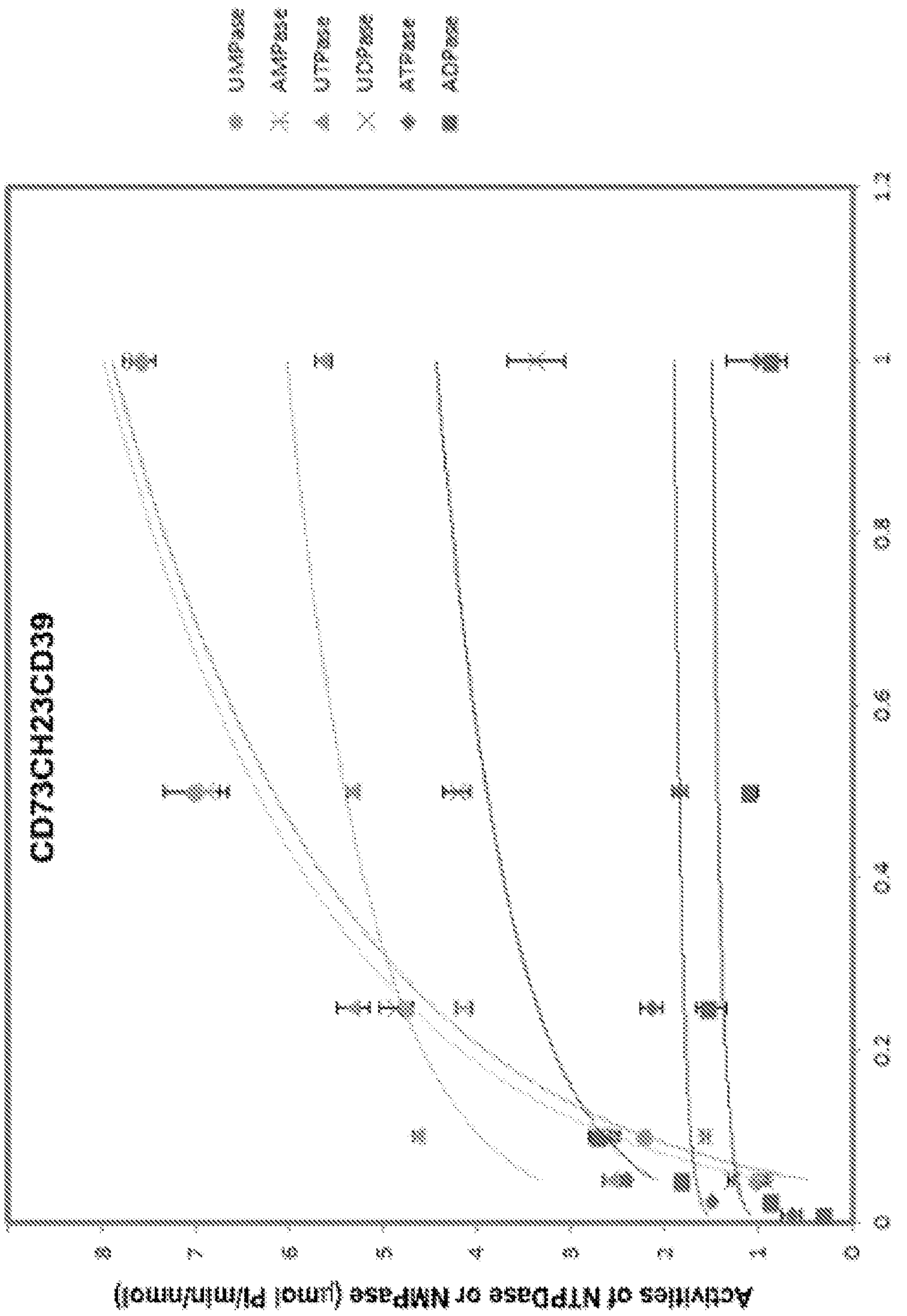
FIGS. 4A-4F are a set of graphs showing enzymatic characterization of bifunctional fusions of CD73CH23CD39 and CD39CH23CD73. Fusion protein CD73CH23CD39 (FIGS. 4A-4C) and CD39CH23CD73 (FIGS. 4D-4F) were measured for NTPDase and NMPase activities. The error bars at each data point were calculated from triplicated experiments.
Figure 4B:
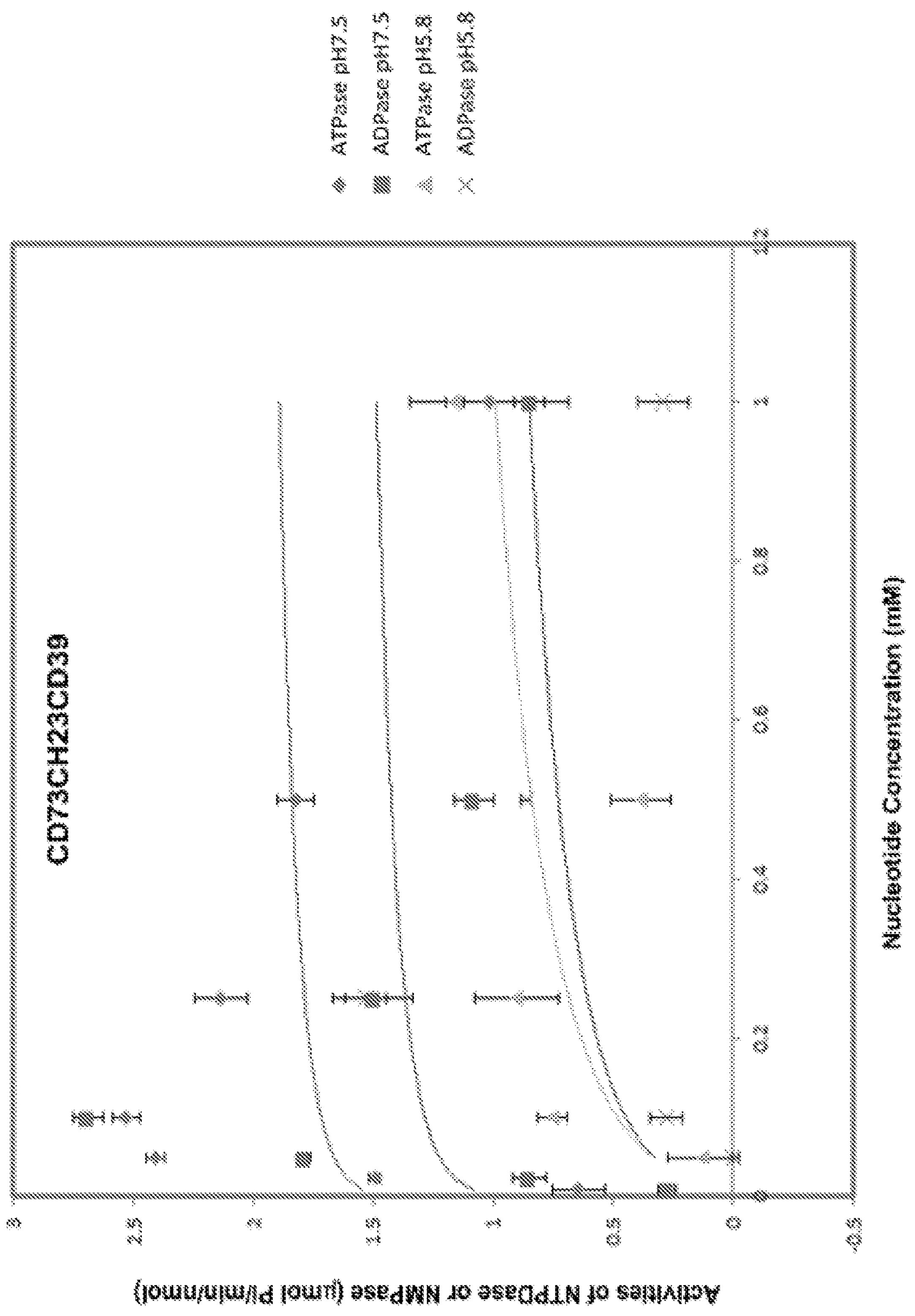
Figure 4C:
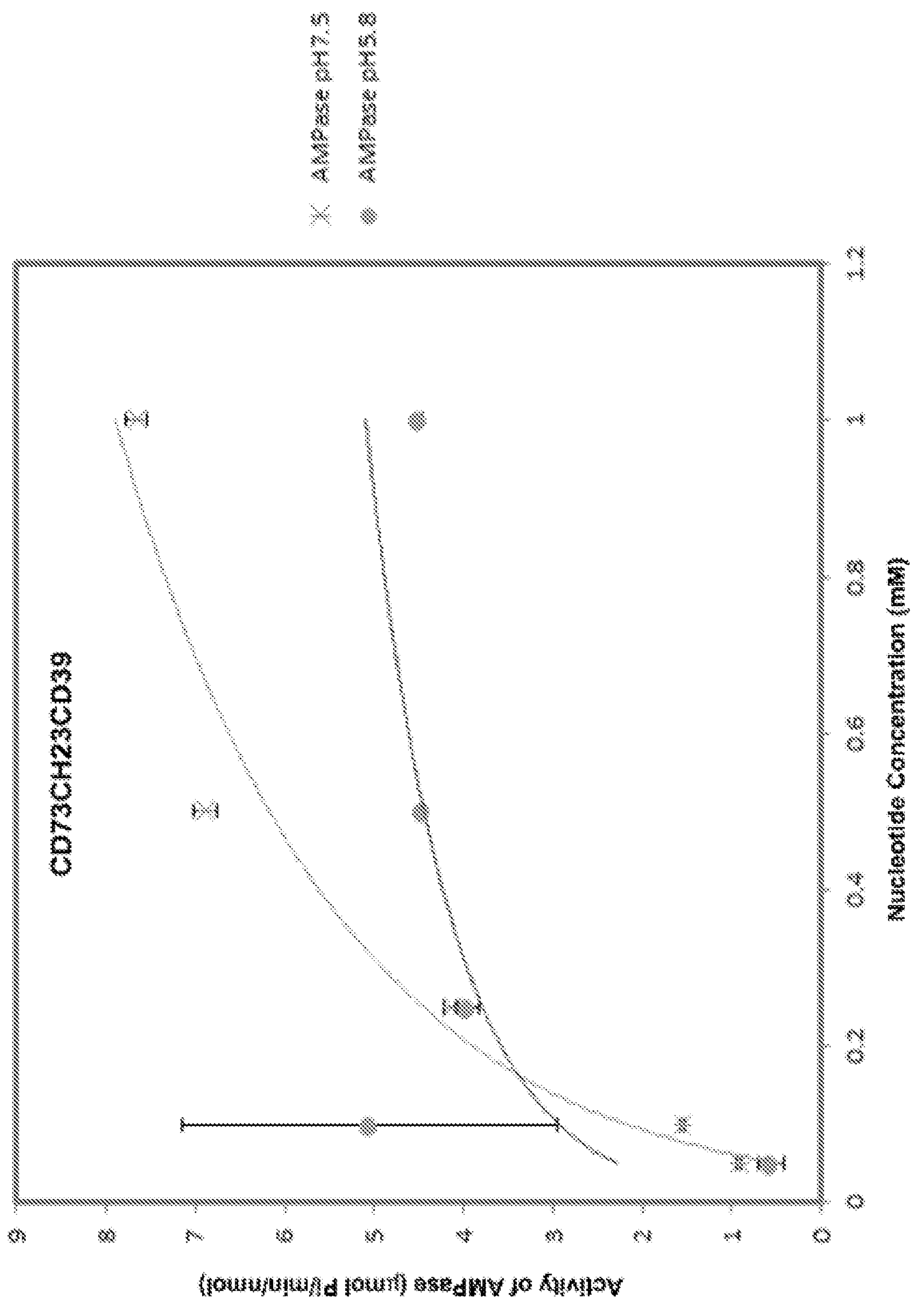
Figure 4D:
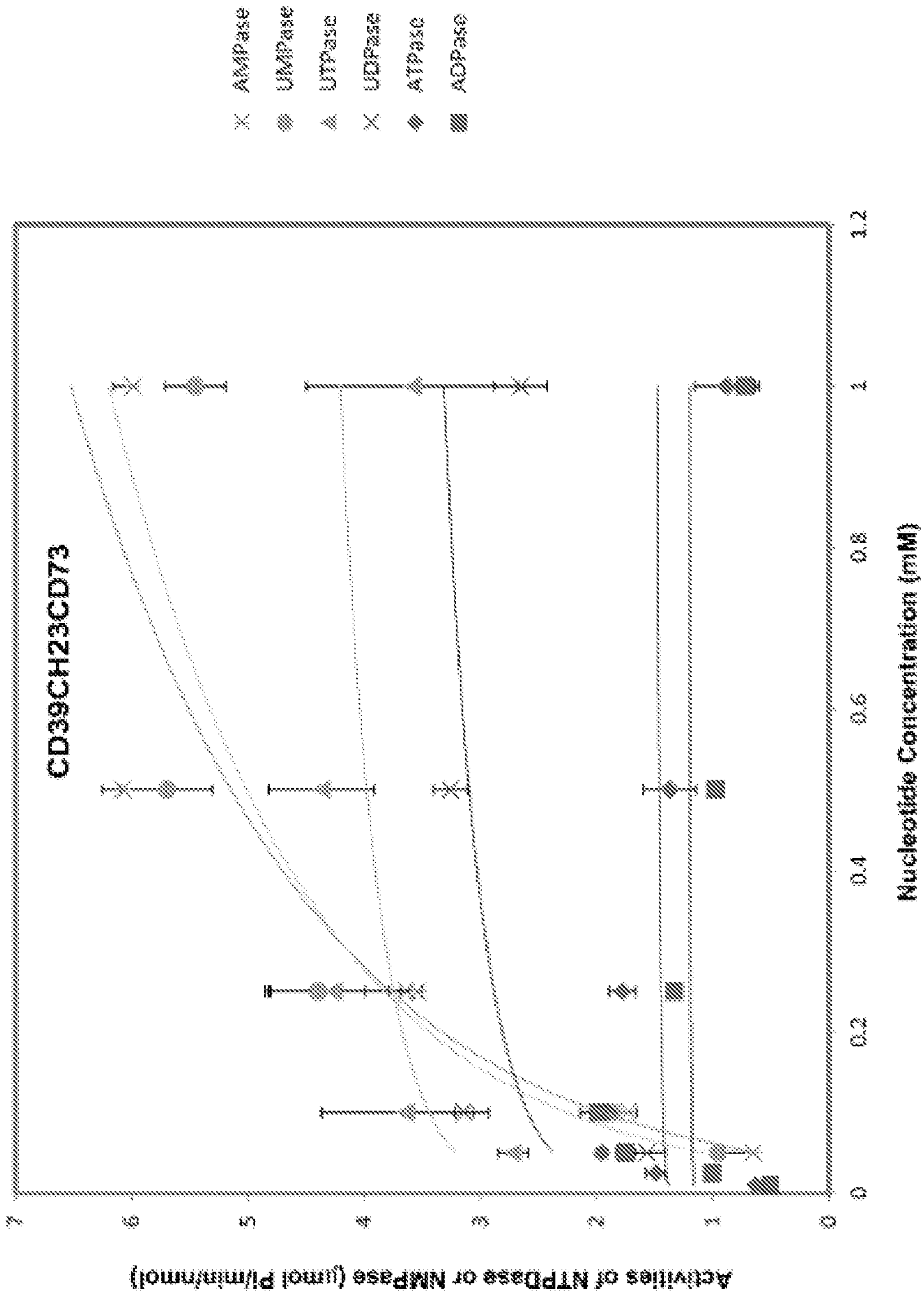
Figure 4E:
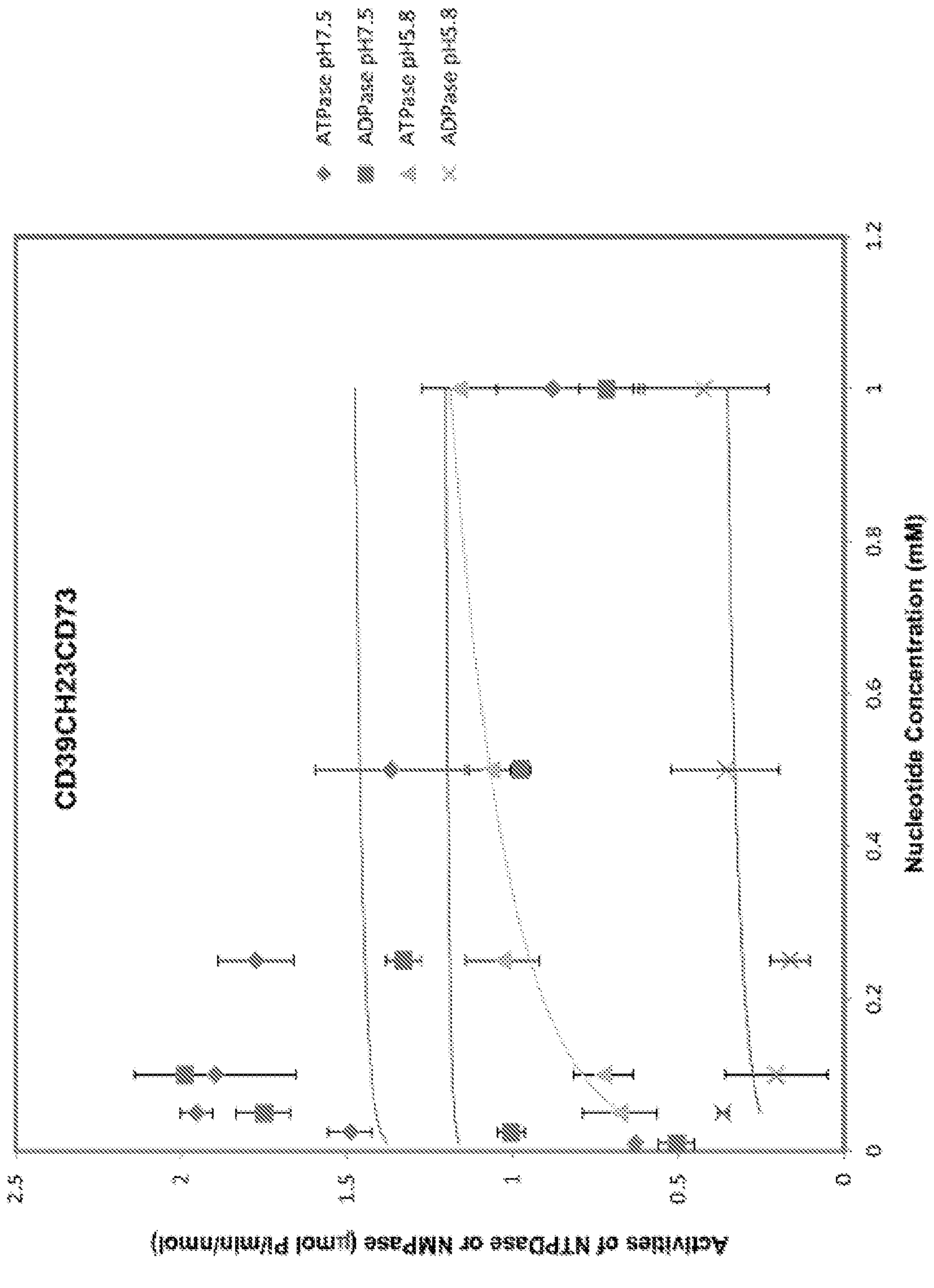
Figure 4F:
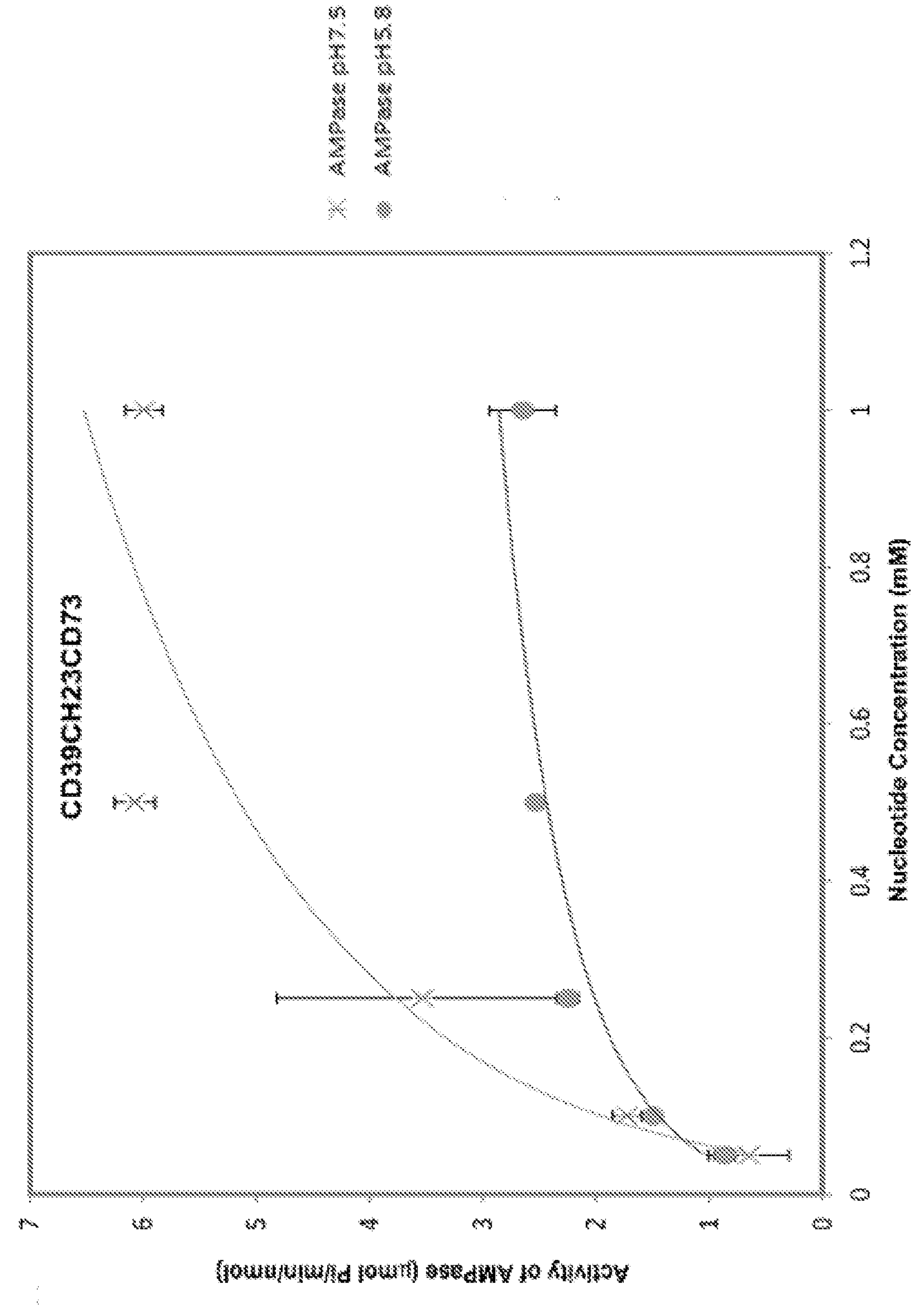

When the bifunctional fusion CD73CH23CD39 was measured, FIG. 4A and Table 4 showed that it possessed both activities NTPDase and NMPase at physiological pH (pH7.5). The Km for NTPDase was significantly lower in the bifunctional fusion than in the CD39CH23 fusion (ATPase Km 0.008 mM vs. 0.037 mM; ADPase Km 0.011 mM vs. 0.11 mM), whereas Vmax was similar (ATPase: 2 μmol/nmol/min; ADPase: 1.57 μmol/nmol/min). The Km and Vmax for NMPase were similar between the bifunctional fusion (AMPase Km 0.46 mM, Vmax 11.73 μmol/nmol/min; UMPase Km 0.32 mM Vmax 10.50 μmol/nmol/min) and CD73CH23. With regards to the pH sensitivity, CD73CH23CD39 Bifunctional Fusion's ATDPase and AMPase activities decreased at acidic pH (FIGS. 4B-4C and Table 4). For another bifunctional fusion CD39CH23CD73, it also displayed both NTPDase and NMPase activities similar to those of CD73CH23CD39 (FIG. 4D and Table 5). Its ATPDase and AMPase activities were also sensitive to acidic pH (FIGS. 4E-4F and Table 5).

TABLE 4

Vmax and Km of CD73CH23CD39 at various pHs for NTPDase and NMPase activities.

| CD73CH23CD39 | Km (mM) | Vmax (μmol Pi/nmol/min) |
|---|---|---|
| ATPase (pH 7.5) | 0.008 | 2.00 |
| UTPase (pH 7.5) | 0.048 | 6.05 |
| ADPase (pH 7.5) | 0.011 | 1.57 |
| UDPase (pH 7.5) | 0.066 | 4.55 |
| AMPase (pH 7.5) | 0.46 | 11.73 |
| UMPase (pH 7.5) | 0.32 | 10.50 |
| ATPase (pH 5.8) | 0.023 | 1.04 |
| ADPase (pH 5.8) | 0.003 | 0.79 |
| AMPase (pH 5.8) | 0.063 | 5.1 |

TABLE 5

Vmax and Km of CD39CH23CD73 at various pHs for NTPDase and NMPase activities.

| CD39CH23CD73 | Km (mM) | Vmax (μmol Pi/nmol/min) |
|---|---|---|
| ATPase (pH 7.5) | 0.023 | 2.57 |
| UTPase (pH 7.5) | 0.022 | 4.26 |
| ADPase (pH 7.5) | 0.019 | 1.93 |
| UDPase (pH 7.5) | 0.059 | 4.27 |
| AMPase (pH 7.5) | 0.34 | 8.73 |
| UMPase (pH 7.5) | 0.21 | 7.29 |
| ATPase (pH 5.8) | 0.047 | 1.19 |
| ADPase (pH 5.8) | 0.014 | 0.38 |
| AMPase (pH 5.8) | 0.10 | 3.02 |

Figure 5A:
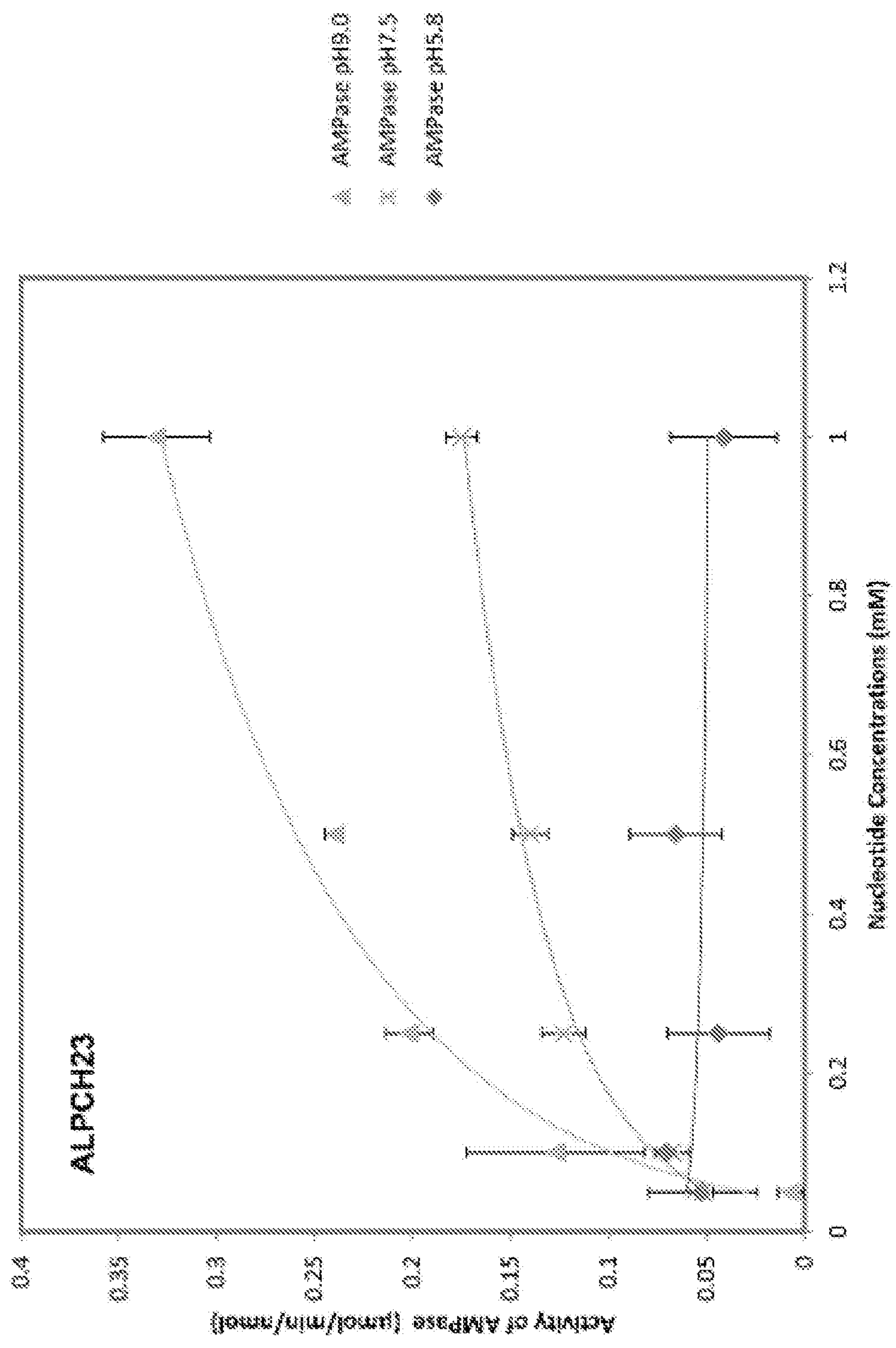
FIGS. 5A-5E are a set of graphs showing enzymatic characterization of ALPCH23 fusion and HAPCH23 fusion. Either ALPCH23 (FIGS. 5A-5C) or HAPCH23 (FIGS. 5D-5F) was respectively measured for NTPDase and NMPase activities. The error bars at each data point were calculated from triplicated experiments.
Figure 5B:
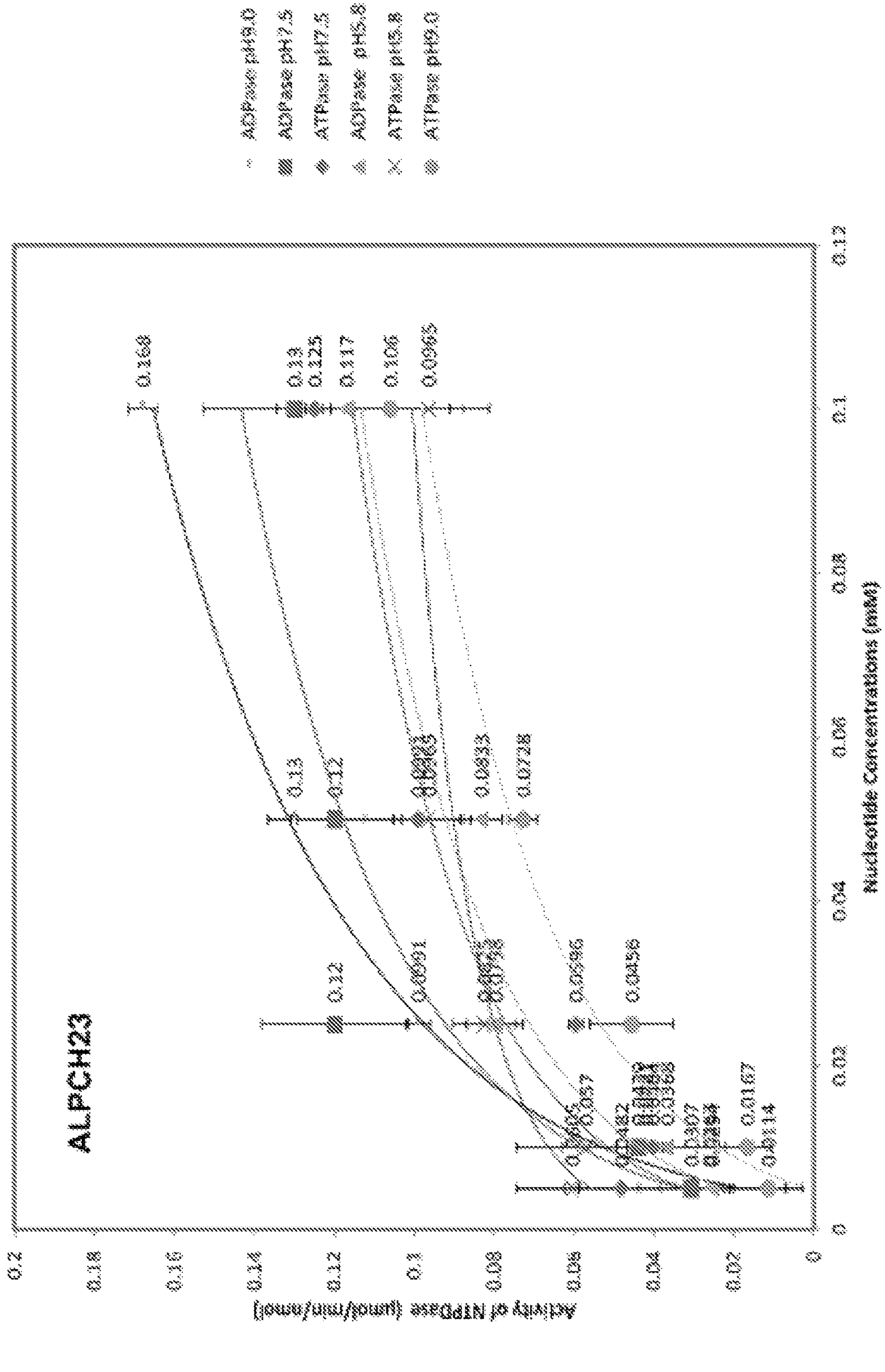

As shown in FIG. 5A and Table 6, human alkaline phosphatase fusion ALPCH23's AMPase activity was more than 55-fold lower than those of the bifunctional fusions at pH7.5 (Km 0.078 mM, Vmax 0.20 μmol/nmol/min) and pH9.0 (Km 0.14 mM, Vmax 0.42 μmol/nmol/min), with little activity at pH5.8. It did exhibit some ATDPase activities at neutral, acidic and alkaline conditions (Vmax 0.1-0.23 μmol/nmol/min), yet 10 to 20-fold lower than those of the bifunctional fusions (FIG. 5B and Table 6).

TABLE 6

Vmax and Km of ALPCH23 at various pHs for NTPDase and NMPase activities.

| ALP-CH23 | Km (mM) | Vmax (μmol Pi/nmol/min) |
|---|---|---|
| AMPase (pH 9.0) | 0.14 | 0.42 |
| AMPase (pH 7.5) | 0.078 | 0.20 |
| AMPase (pH 5.8) | N/A | N/A |
| ATPase (pH 7.5) | 0.026 | 0.15 |
| ATPase (pH 5.8) | 0.0048 | 0.10 |
| ATPase (pH 9.0) | 0.090 | 0.20 |
| ADPase (pH 7.5) | 0.018 | 0.16 |
| ADPase (pH 5.8) | 0.024 | 0.14 |
| ADPase (pH 9.0) | 0.038 | 0.23 |

Figure 5C:
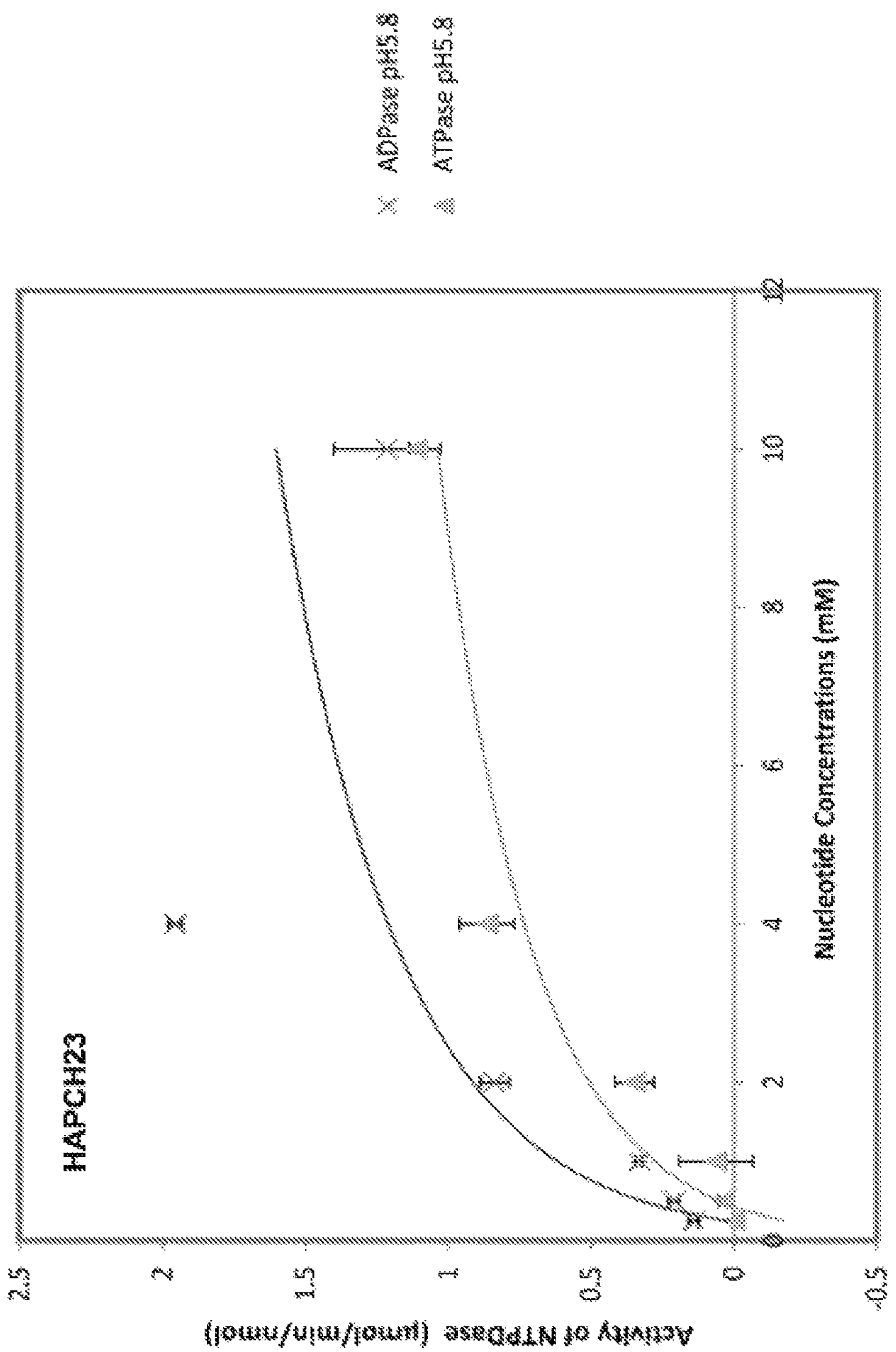
Figure 5D:
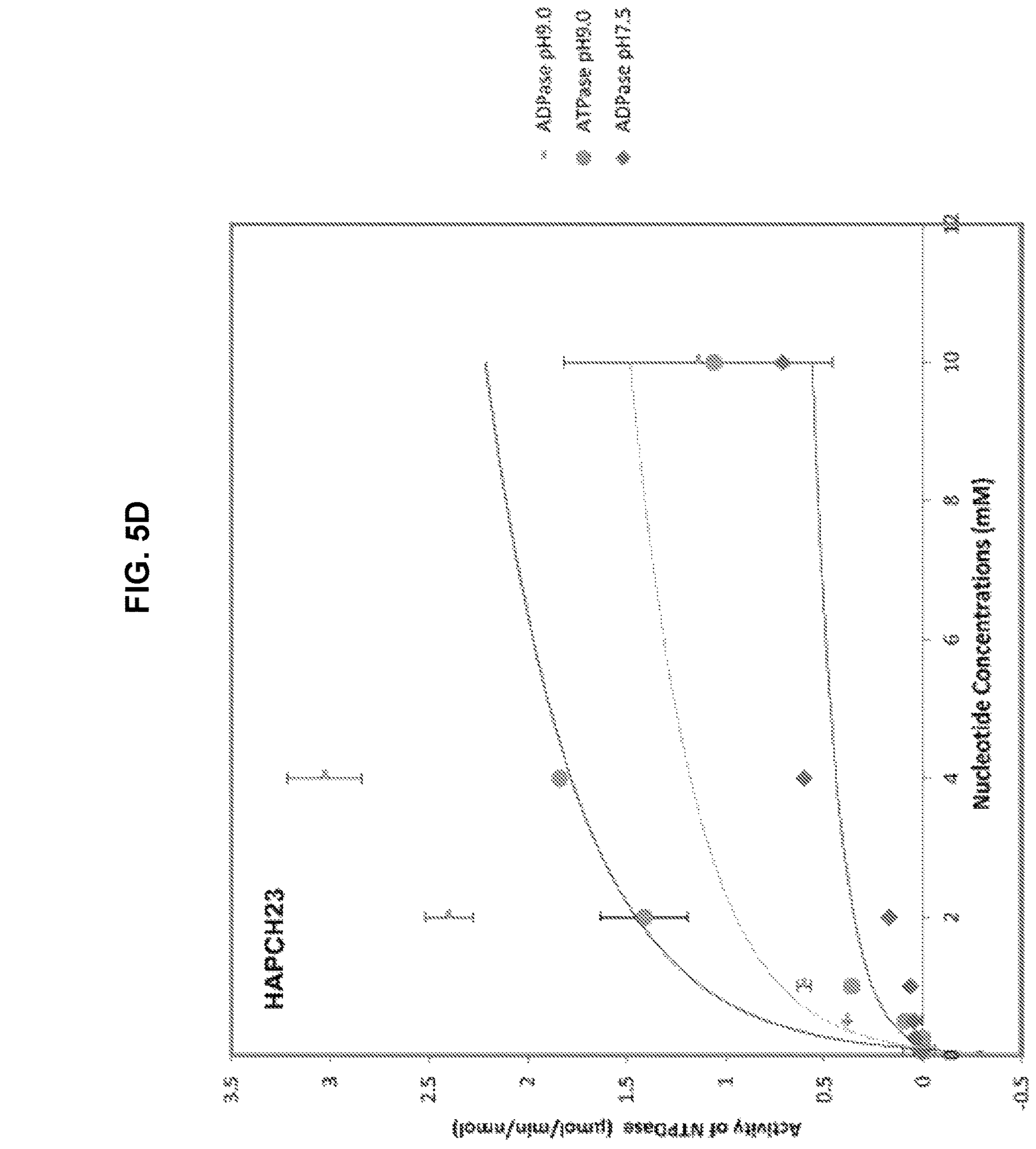
Figure 5E:
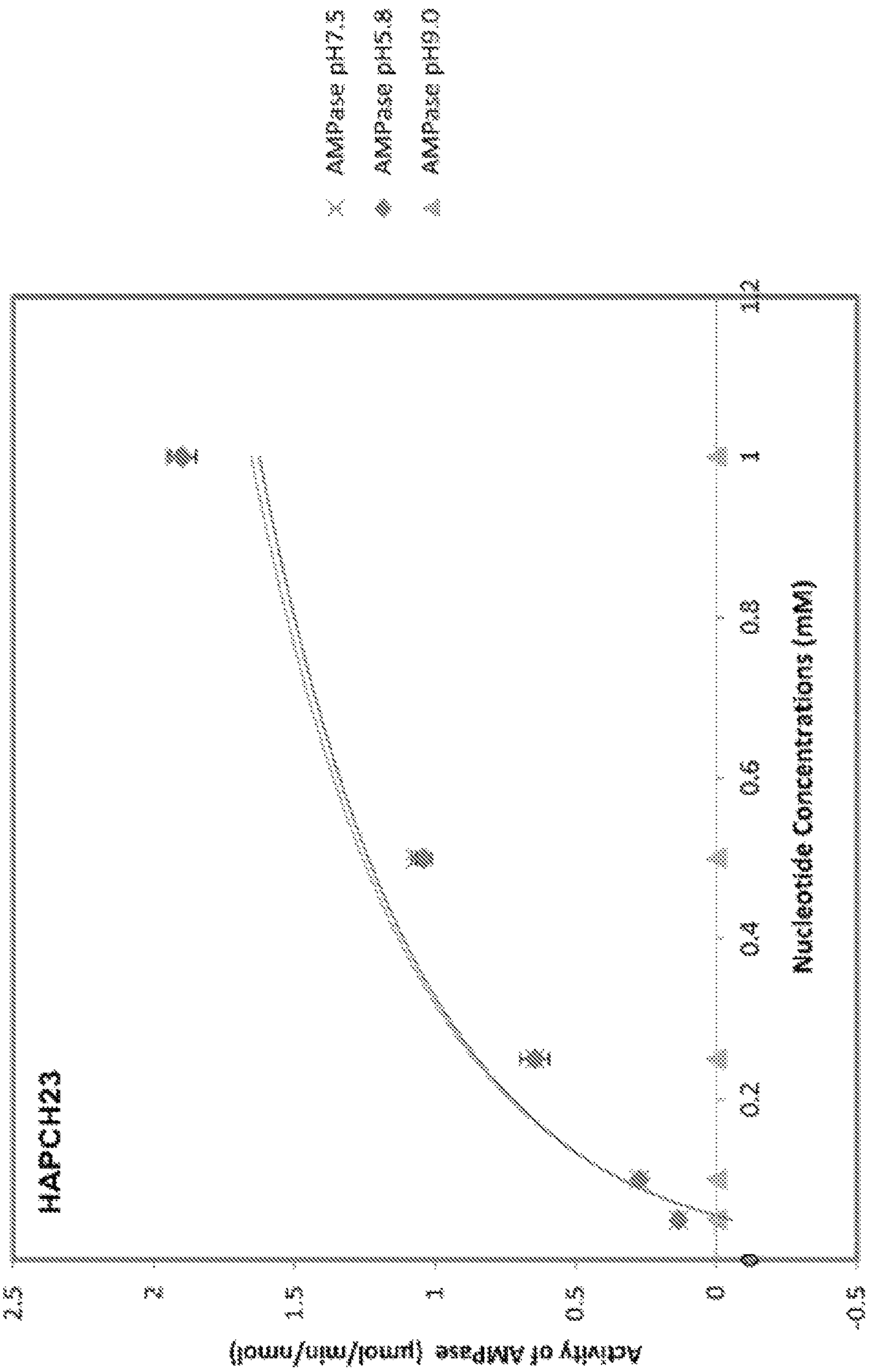

Human acidic phosphatase fusion HAPCH23 possessed ATPase (Km 9.08 mM, Vmax 2.21 μmol/nmol/min), ADPase (Km 2.1 mM, Vmax 1.91 μmol/nmol/min), and AMPase activities (Km 2.58 mM, Vmax 6.77 μmol/nmol/min) at acidic pH (FIGS. 5C-5D and Table 7). It had no AMPase activity detected at alkaline pH, but showing some ATPase (Km 1.42 mM, Vmax 1.74 μmol/nmol/min) and ADPase activities (Km 0.92 mM, Vmax 2.37 μmol/nmol/min) (FIG. 5C and Table 7). At physiological pH, HAPCH23 displayed AMPase (Km 2.59 mM, Vmax 6.89 μmol/nmol/min) and ADPase activities (Km 8.39 mM, Vmax 1.38 μmol/nmol/min), but little ATPase activity (FIG. 5D-5E and Table 7).

TABLE 7

Vmax and Km of HAPCH23 at various pHs for NTPDase and NMPase activities.

| HAP-CH23 | Km (mM) | Vmax (μmol Pi/mg/min) |
|---|---|---|
| ATPase (pH 5.8) | 9.08 | 2.21 |
| ATPase (pH 7.5) | N/A | N/A |
| ATPase (pH 9.0) | 1.42 | 1.74 |
| ADPase (pH 5.8) | 2.1 | 1.91 |
| ADPase (pH 7.5) | 8.39 | 1.38 |
| ADPase (pH 9.0) | 0.92 | 2.37 |

TABLE 7-continued

| Vmax and Km of HAPCH23 at various pHs for NTPDase and NMPase activities. | | |
|---|---|---|
| HAP-CH23 | Km (mM) | Vmax (μmol Pi/mg/min) |
| AMPase (pH 5.8) | 2.58 | 6.77 |
| AMPase (pH 7.5) | 2.59 | 6.89 |
| AMPase (pH 9.0) | N/A | N/A |

With all these data together, the bifunctional fusion enzymes exhibited robust NTPDase and NMPase activities with low Km and high Vmax. They were also active at physiological, acidic, and alkaline pHs. As measured by colorimetrical assay, the bifunctional fusions were superior over alkaline phosphatase and acid phosphatase in converting tri- and di-phosphate nucleosides into nucleosides.

HPLC Kinetic Analysis of Bifunctional Fusions and Control Fusion Proteins

To further understand the enzyme kinetics of the bifunctional fusions and the control fusion proteins, we performed a time course study on ATPase, ADPase, and AMPase at 0 min, 5 min, 10 min, 20 min, and 40 mins at 37° C. at pH7.5. 2.1 nmols of enzyme proteins were added to 100 μl reaction with 0.5 mM of ATP, ADP, or AMP. The reaction was terminated with 5 mM of perchloride acid and subjected to HPLC analysis for the accumulation or disappearance of nucleotides, as described in Materials and Methods. The peak of each corresponding nucleotides was quantified.

Figure 6A:
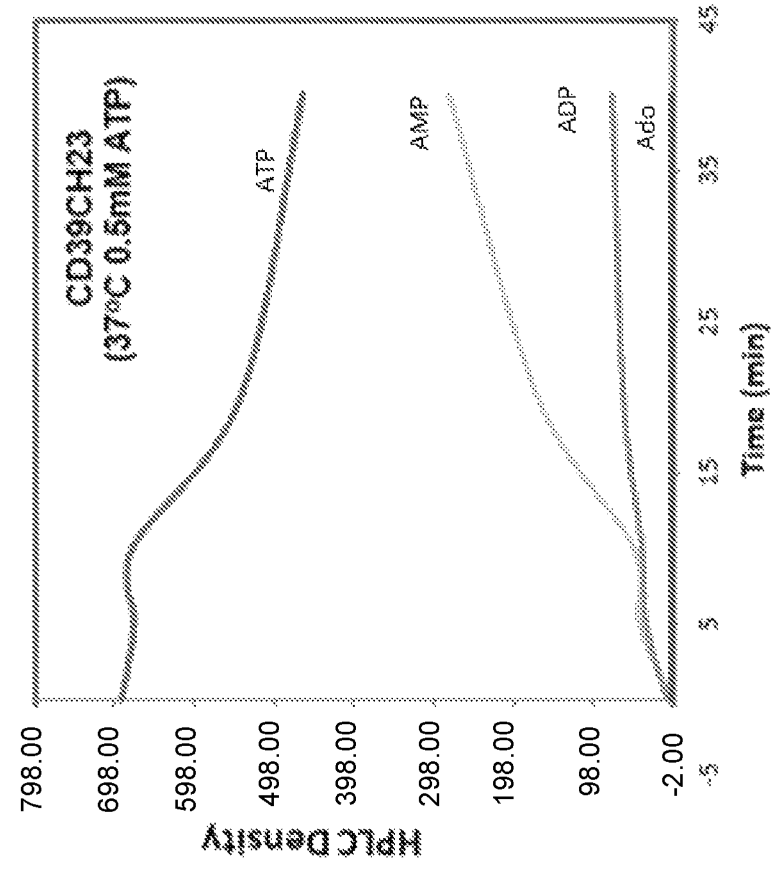
FIGS. 6A-6F are chromatograms showing HPLC kinetic characterization of CD39CH23 fusion and CD73CH23 fusion. 2.1 pmol of either CD39CH23 (FIGS. 6A-6C) or CD73CH23 (FIGS. 6D-6F) was respectively added to 100 μl reaction buffer (20 mM Tris-HCl, pH7.5, 120 mM NaCl, 5 mM KCl, 0.5 mM EDTA, 5 mM $CaCl_2$)) with 0.5 mM ATP, 0.5 mM ADP, or 0.5 mM AMP at 37° C. for 5 min, 10 min, 20 min and 40 min. Each reaction was terminated by addition of 5 μl 8M PCA in ice, and then subjected to HPLC analysis.
Figure 6B:
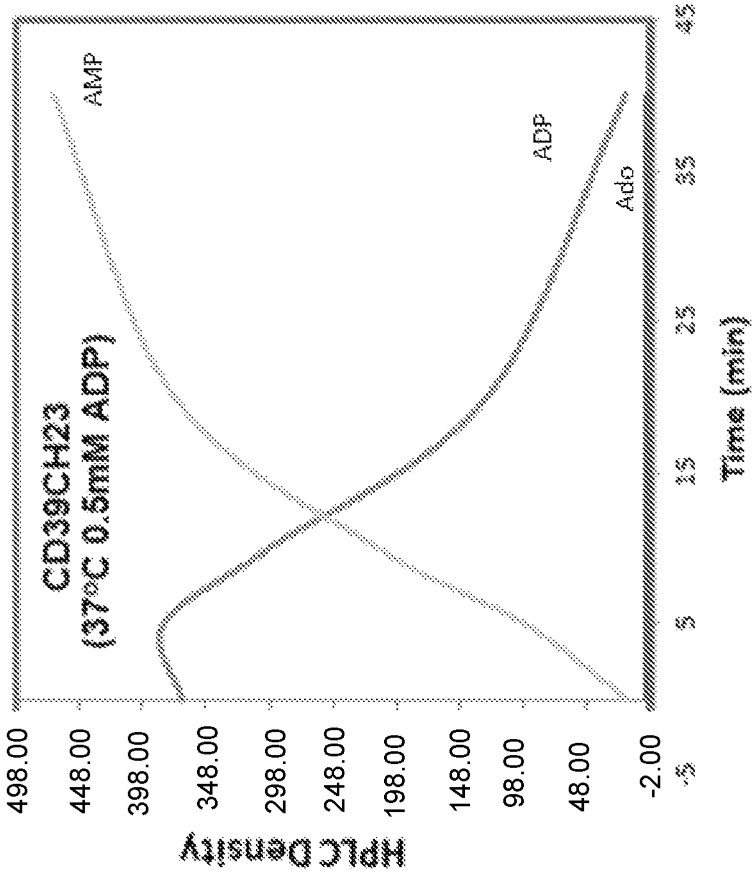
Figure 6C:
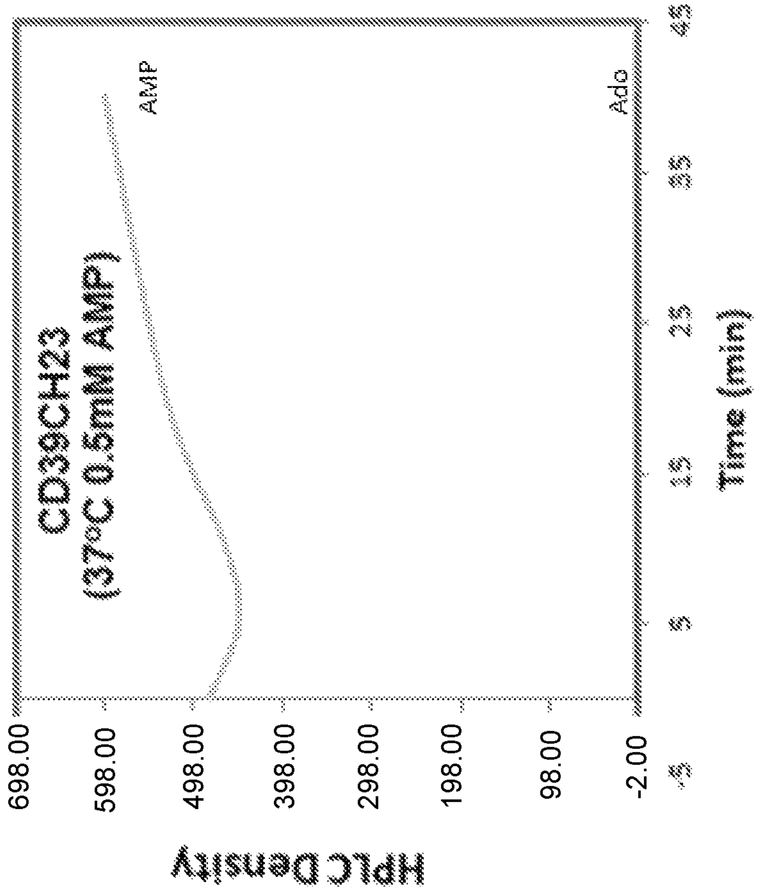
Figure 6D:
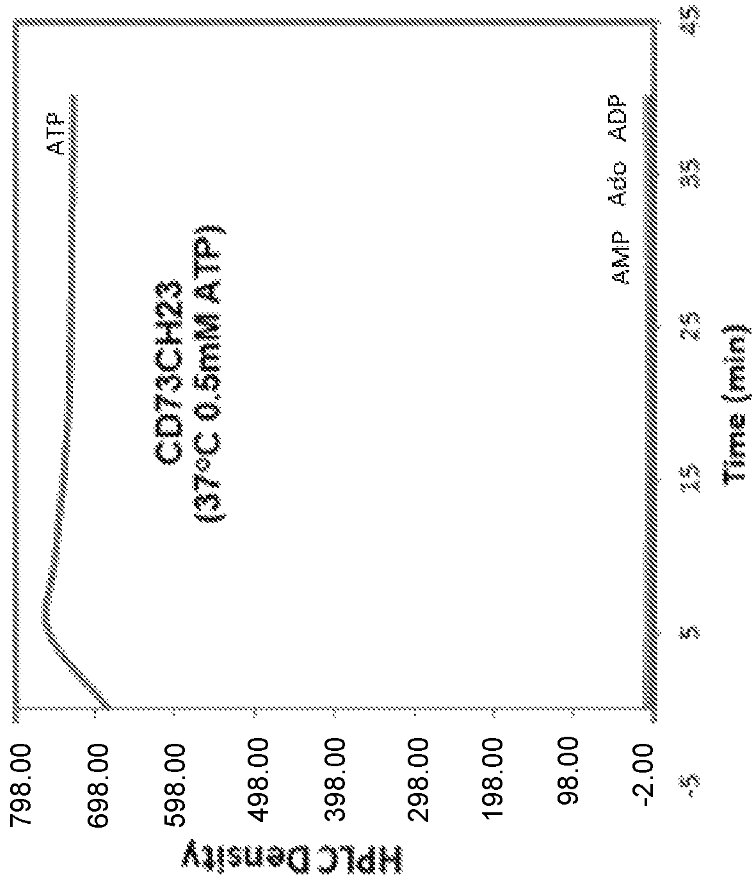
Figure 6E:
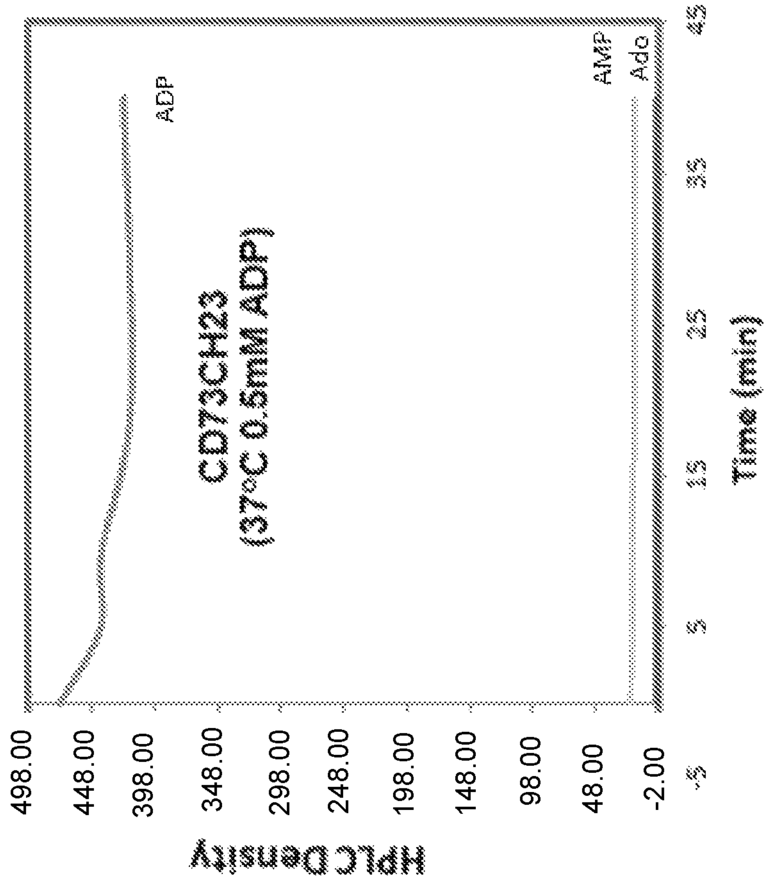
Figure 6F:
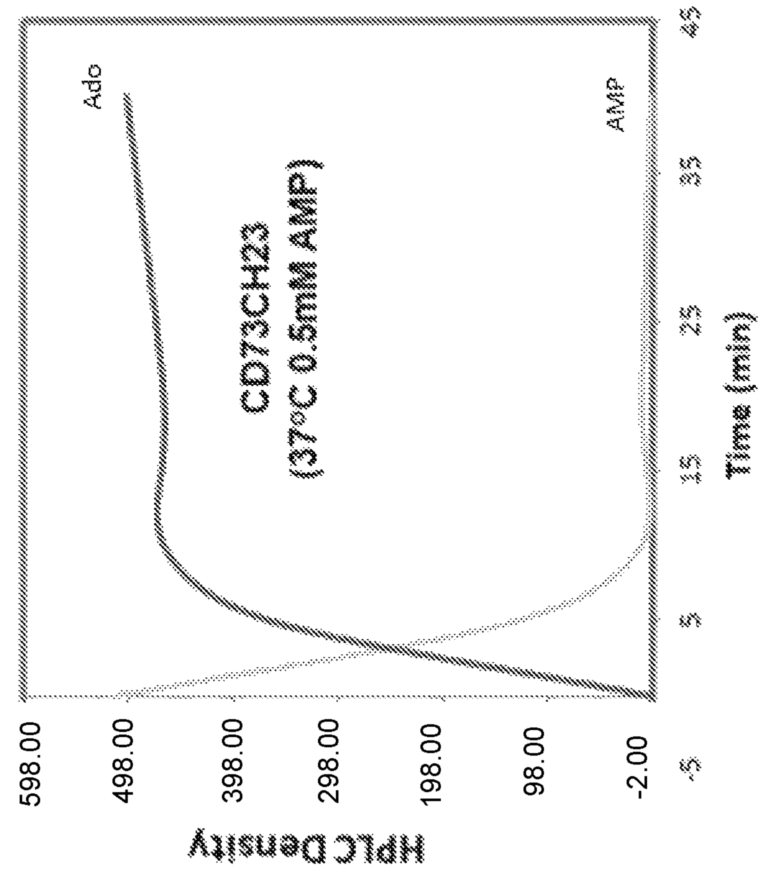

As shown in FIG. 6A, CD39CH23 decreased ATP over time and its AMP accumulated over time whereas a smaller amount of ADP was also detected, consistent with the notion that some ADP was generated during CD39-ECD's ATP hydrolysis. No adenosine was detected during the hydrolysis. Similarly, when ADP was the starting substrate, CD39CH23 depleted ADP over time and its AMP accumulated over time without the generation of adenosine (FIG. 6B). As shown in FIG. 6C, CD39CH23 cannot hydrolyze AMP, consistent with the colorimetrical data. As shown in FIGS. 6D-6E, CD73CH23 had no activity towards ATP and ADP, but it hydrolyzed most of AMP within 5 minutes, exhibiting potent enzymatic activity (FIG. 6F).

Figure 7A:
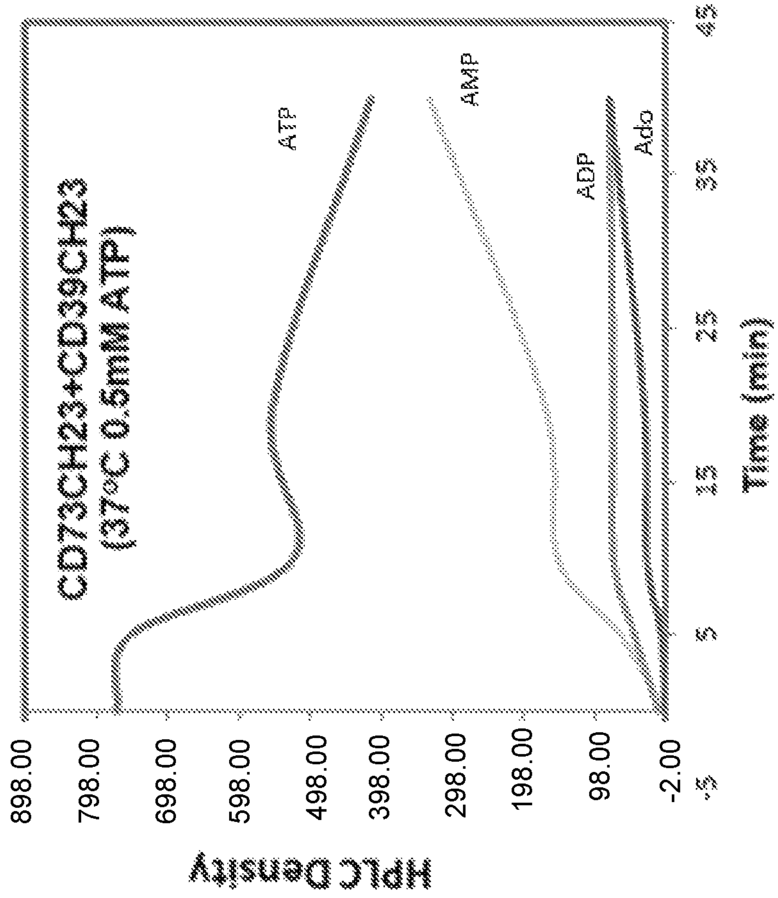
FIGS. 7A-7F are chromatograms showing HPLC kinetic characterization of the mixture of CD39CH23 and CD73CH23, and the bifunctional fusion CD73CH23CD39. The mixture of 2.1 pmol CD39CH23 and 2.1 pmol CD73CH23 (FIGS. 7A-7C) or bifunctional fusion CD73CH23CD39 (FIGS. 7D-7F) were respectively added to 100 μl reaction buffer (20 mM Tris-HCl, pH7.5, 120 mM NaCl, 5 mM KCl, 0.5 mM EDTA, 5 mM $CaCl_2$)) with 0.5 mM ATP, 0.5 mM ADP, or 0.5 mM AMP at 37° C. for 5 min, 10 min, 20 min and 40 min. Each reaction was terminated by addition of 5μl 8M PCA in ice, and then subjected to HPLC analysis.
Figure 7B:
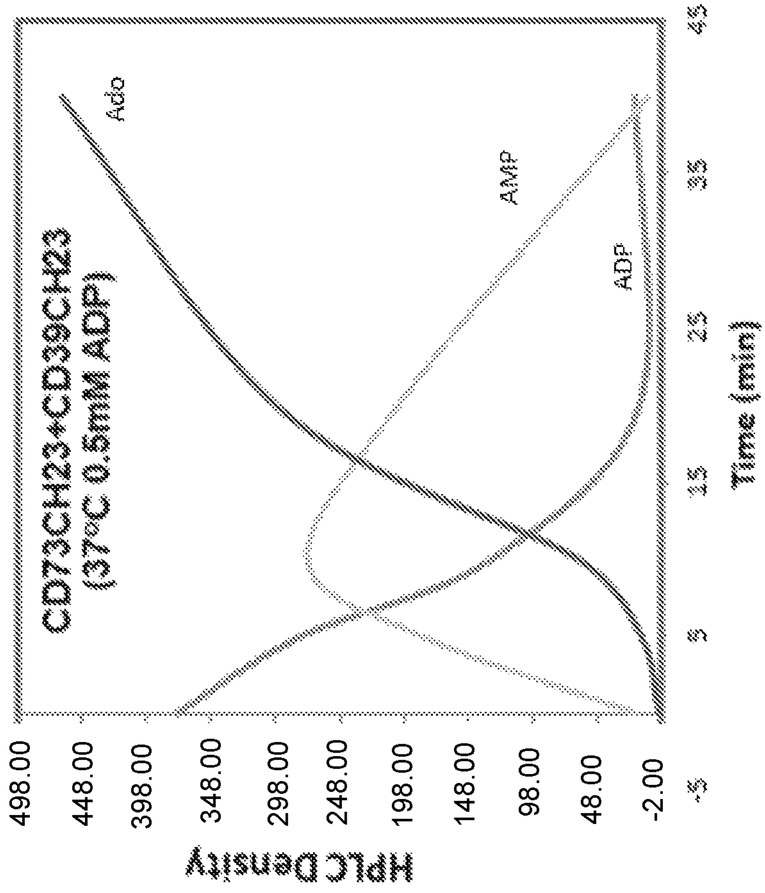
Figure 7C:
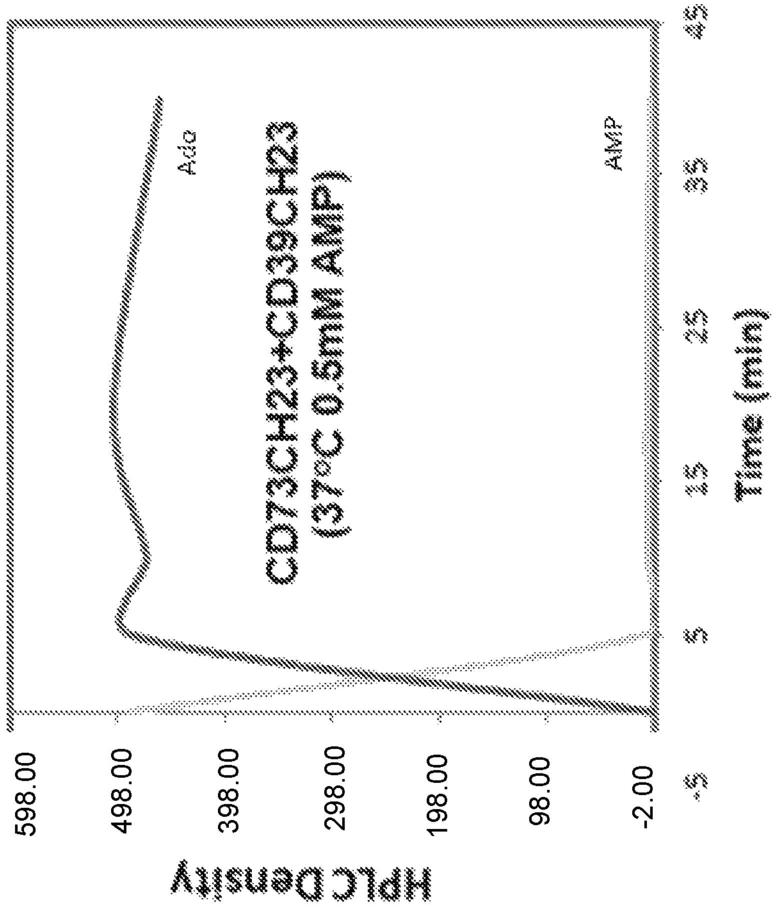

As shown in FIG. 7A, when equal molar of CD39CH23 and CD73CH23 were mixed together in the HPLC assay, ATP decreased gradually whereas AMP, ADP, and adenosine started to accumulate sequentially. When ADP was the starting substrate (FIG. 7B), it got hydrolyzed mostly within 20 mins. AMP accumulated quickly and reached the peak in 10 mins, then decreased, whereas adenosine continued to increase. When AMP being the starting substrate (FIG. 7C), it was consumed completely within 5 mins, similar to those with CD73CH23 alone.

Figure 7D:
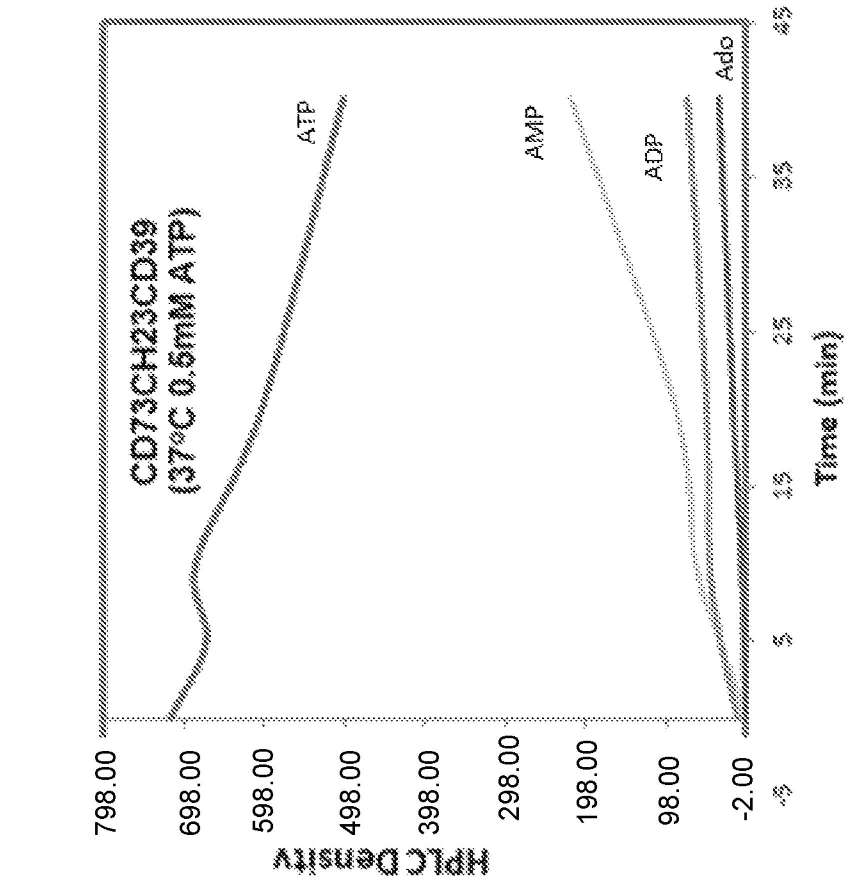
Figure 7E:
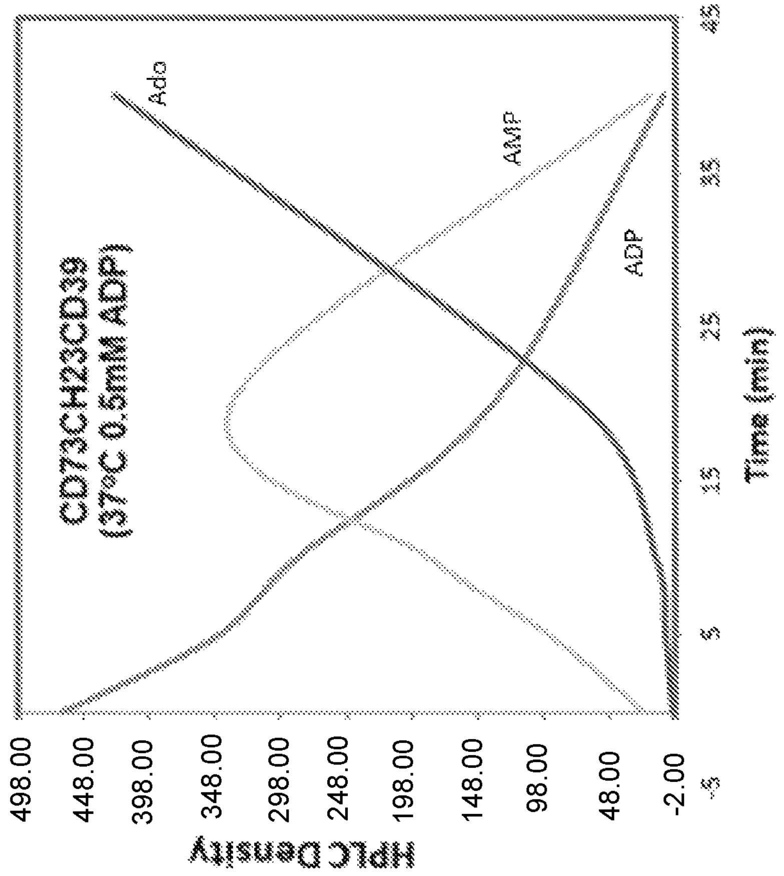
Figure 7F:
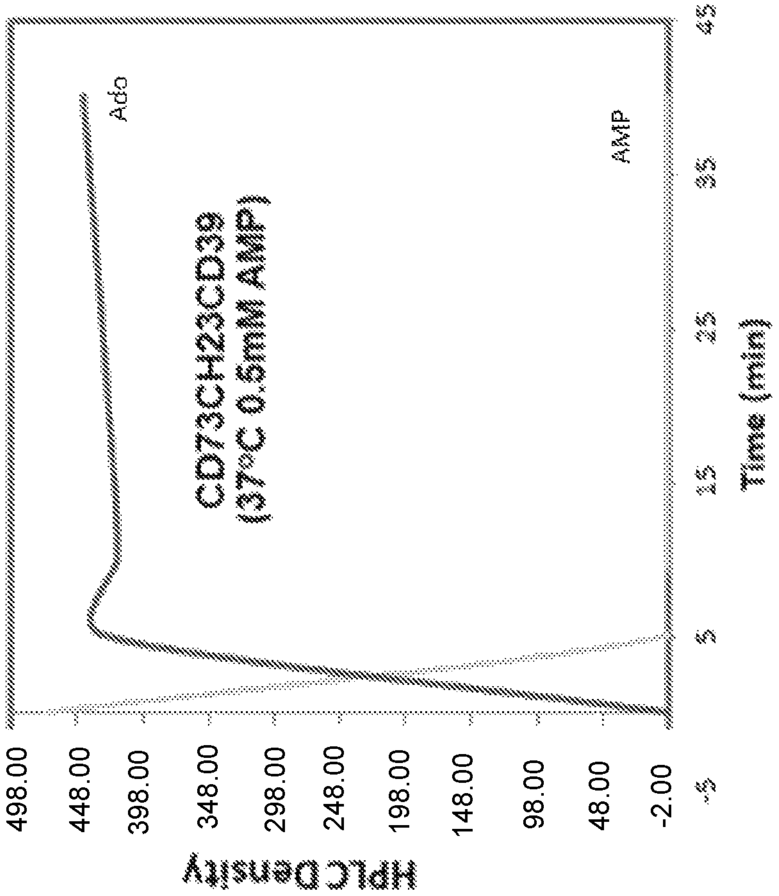

When the bifunctional enzyme CD73CH23CD39 was analyzed (FIGS. 7D-7F), the HPLC kinetic profile was similar to that of the CD39CH23 and CD73CH23 mixture. When ATP was the starting substrate (FIG. 7D), the accumulation of ADP, AMP and adenosine were slightly slower than those of the mixture. When ADP being the start substrate (FIG. 7E), AMP reached its peak in 20 mins versus 10 min for the mixture, then decreased. The adenosine's accumulation was also delayed proportionally than that in the enzyme mixture. When AMP being the substrate (FIG. 7F), the bifunctional fusion consumed it completely within 5 min, similar to CD73CH23 alone.

Figure 8A:
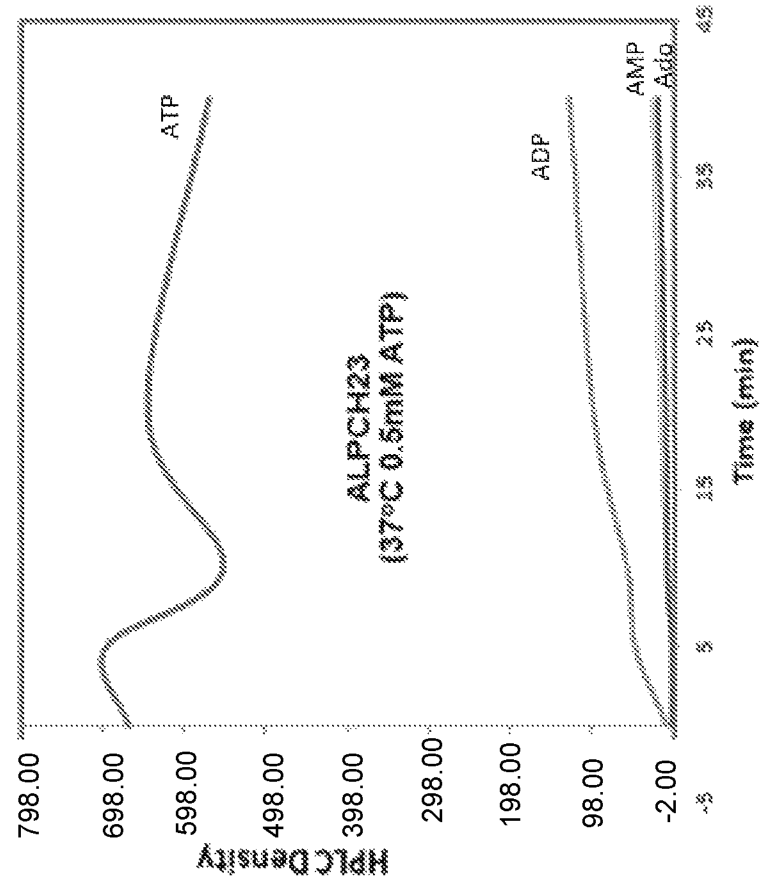
FIGS. 8A-8F are chromatograms showing HLPC kinetic characterization of ALPCH23 fusion and HAPCH23 fusion. 2.1 pmol of either ALPCH23 (FIGS. 8A-8C) or HAPCH23 (FIGS. 8D-8F) was respectively added to 100 μl reaction buffer (20 mM Tris-HCl, pH7.5, 120 mM NaCl, 5 mM KCl, 0.5 mM EDTA, 5 mM $CaCl_2$)) with 0.5 mM ATP, 0.5 mM ADP, or 0.5 mM AMP at 37° C. for 5 min, 10 min, 20 min and 40 min. Each reaction was terminated by addition of 5 μl 8M PCA in ice, and then subjected to HPLC analysis.
Figure 8B:
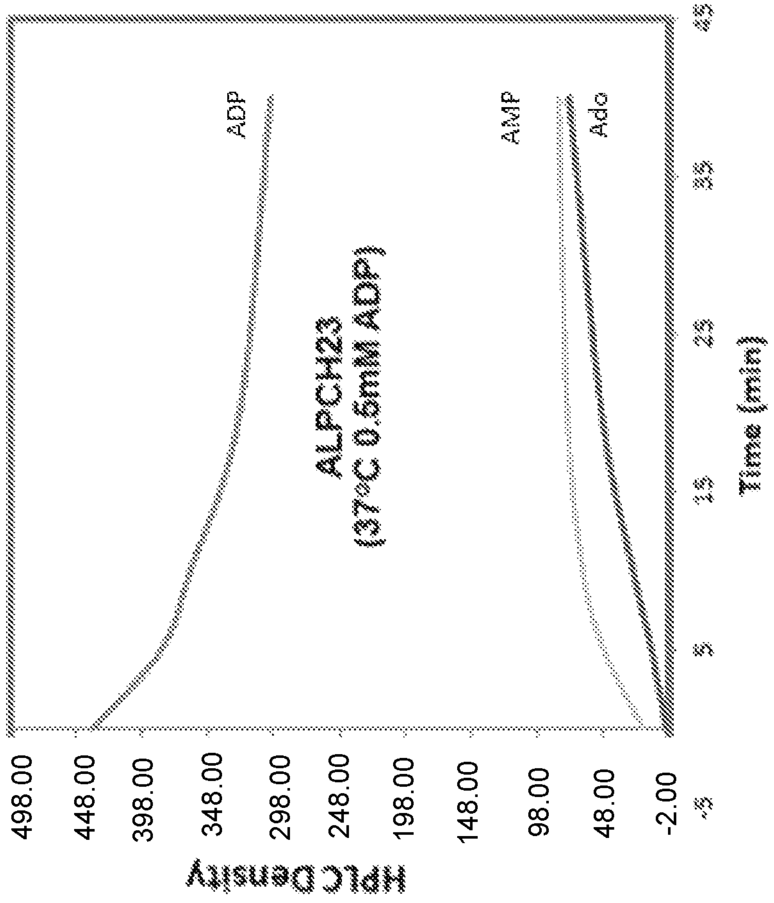
Figure 8C:
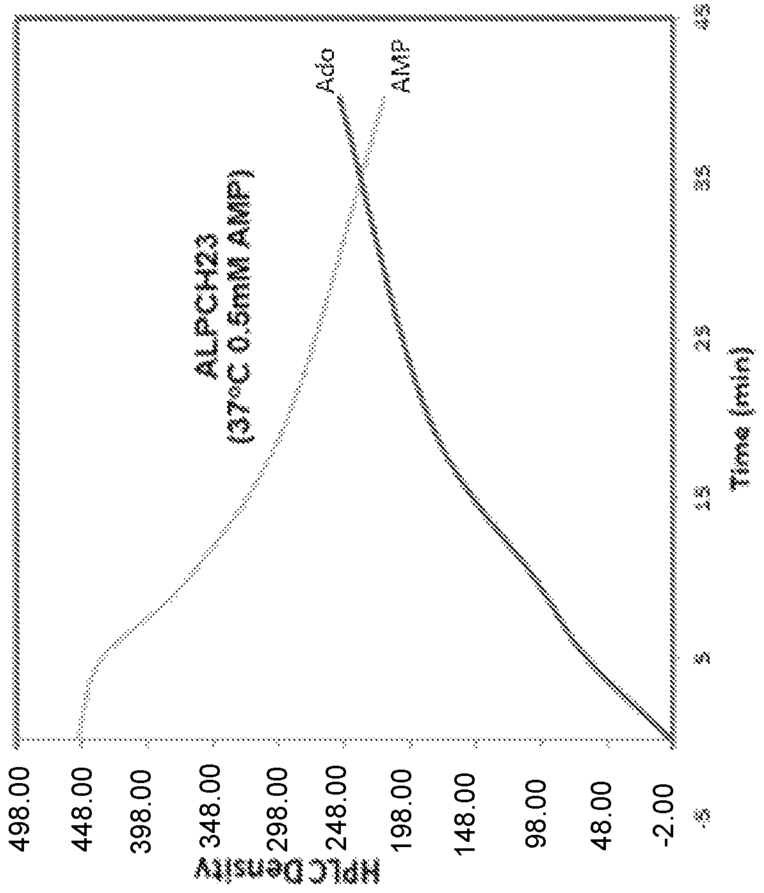
Figure 8D:
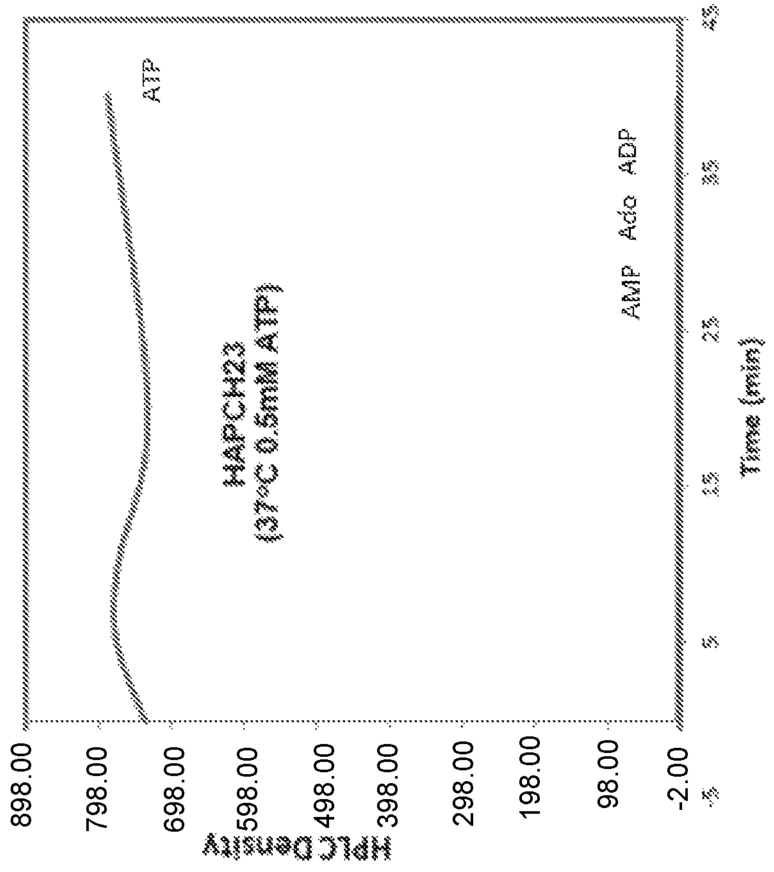
Figure 8E:
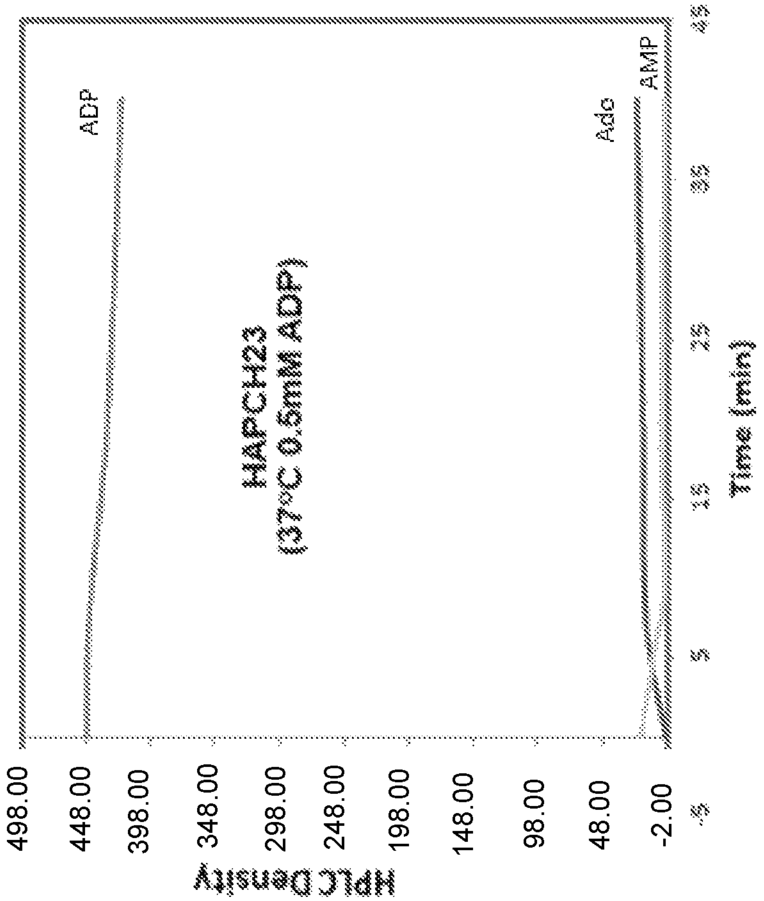
Figure 8F:
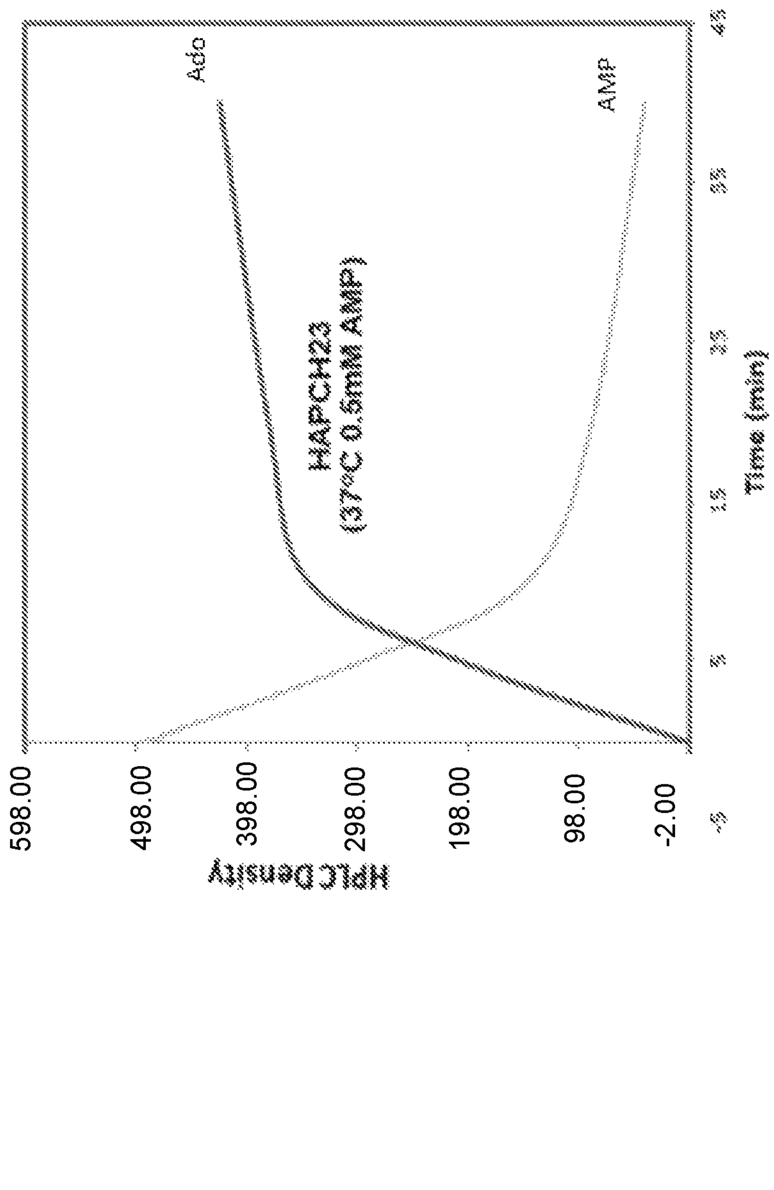

When alkaline phosphatase fusion was analyzed (FIGS. 8A-8C), ATP decreased much slower and ADP was the main accumulation (FIG. 8A), contrasting to that of the bifunctional fusion with AMP as the main intermediate. When ADP being the starting substrate (FIG. 8B), it decreased slightly faster than ATP in panel A. Both AMP and adenosine were accumulated. When AMP being the starting substrate (FIG. 8C), it decreased faster than ADP in panel B and consumed nearly 50% within 40 mins. When acid phosphatase fusion was analyzed (FIGS. 8D-8F), it had no hydrolysis on ATP (FIG. 8D), consistent with the colorimetrical data. When ADP being the start substrate, some AMP and adenosine were detected (FIG. 8E). When AMP being the starting substrate (FIG. 8F), significant activity was observed. AMP was consumed nearly consumed 50% within 10 mins, significantly faster than that of alkaline phosphatase.

Platelet Function In Vitro Inhibited by CD39CD73 Bifunctional Fusion

Figure 9A:
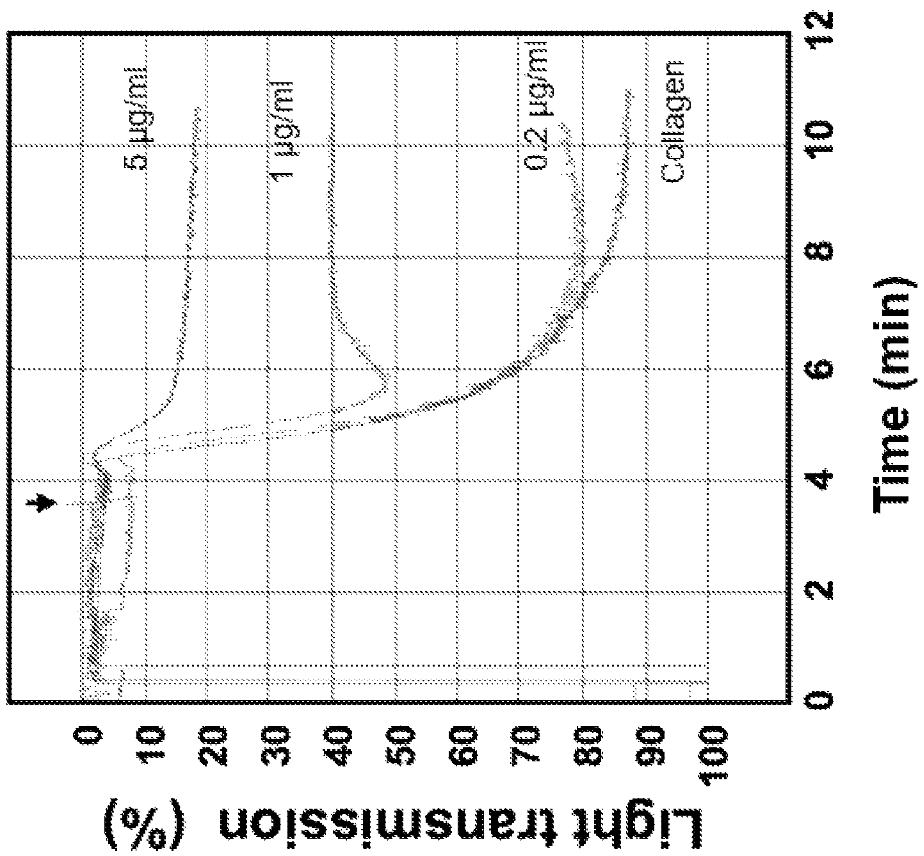
FIGS. 9A and 9B are graphs showing inhibition of platelet function in vitro by CD39CD73 bifunctional fusion at three different concentrations. CD39-CD73 bifunctional fusion protein was added 2 min before adding agonist. Arrow: agonist addition.
Figure 9B:
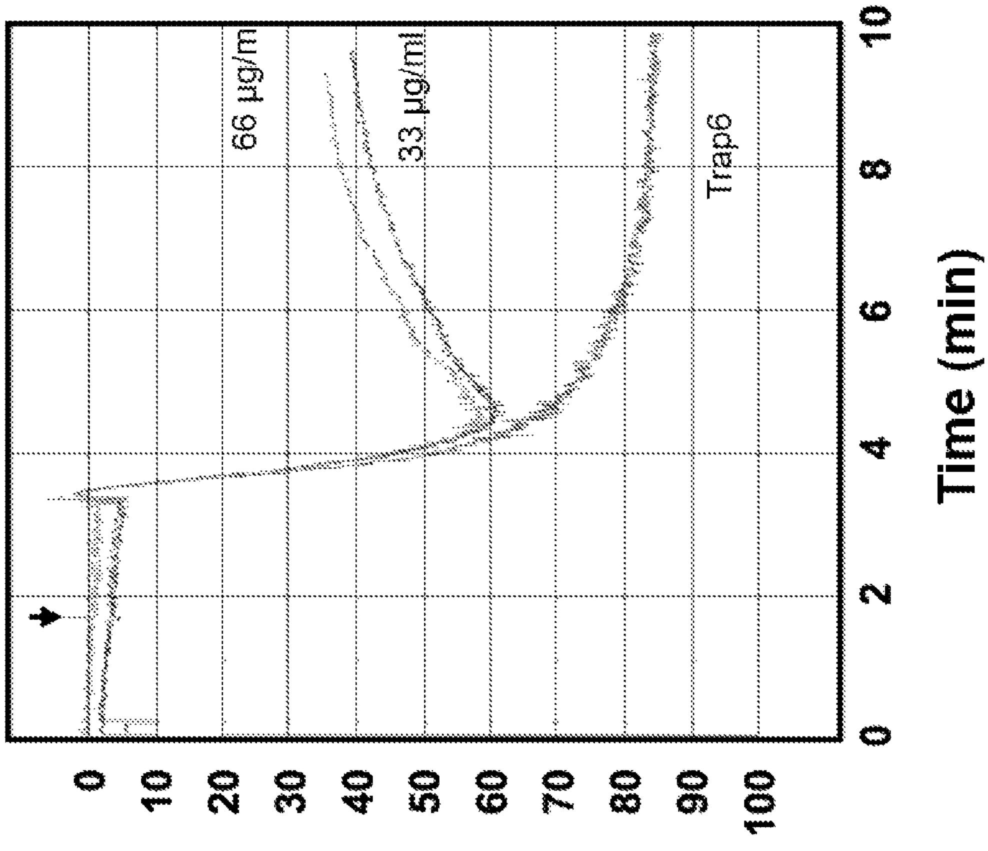

To demonstrate that the bifunctional fusion has biological efficacy, platelet aggregation assay was performed as described in Materials & Methods. When platelets were incubated at 37° C. in the presence of collagen or Trap6, aggregation occurred as determined by light transmission. As shown in FIG. 9A, treatment with the CD73CH23CD39 bifunctional fusion at the concentrations of 0.2, 1, or 5 μg/ml inhibited the platelet aggregation at 2 μg/ml of collagen. Similarly, treatment with the CD73CH23CD39 bifunctional fusion at the concentrations of 33 μg/ml or 66 μg/ml inhibited the platelet aggregation at 12.5 mM of Trap6 (FIG. 9B). These data together demonstrated that the bifunctional fusion was highly active in inhibiting platelet aggregation.

DISCUSSION

Regulating sophisticated conversion of pro-inflammatory ATP and ADP into immunosuppressive adenosine by multiple ectonucleotidase families casts a profound impact on biological processes such as inflammatory responses and thromboregulatory disturbances. By fusing the ectodomains of CD39 and CD73 into a single polypeptide, we have engineered bifunctional enzymes which hydrolyzed tri- and di-phosphate nucleotides directly into nucleosides. These engineered enzymes can be used to effectively terminate P2 receptor signaling and activate $P_1$ receptor signaling, bypassing spatial and temporal expression patterns, enzyme activity variation, enzyme concentration and localization of CD39 and CD73 in different tissues and cell types under varied biological conditions. We have demonstrated that the bifunctional enzymes efficiently hydrolyzed ATP and ADP into adenosine via AMP intermediate, superior to human alkaline phosphatase and acid phosphatase. With the result of inhibiting platelet aggregation, these data together show that the bifunctional enzymes could be used effectively as a therapeutic, either alone or in combination with one or more additional therapeutic regimens for reducing platelet aggregation and/or inflammatory processes, for both reducing pro-inflammatory ATP and producing anti-inflammatory adenosine.

The engineered bifunctional enzymes appear well-behaved functionally and biochemically, even though they contain three different functional domains, Fc domain and ECD of CD39 and CD73. Among four versions of the fusions, the Dumbbell-shape form with CD39-ECD and CD73-ECD flanking Fc domain seems to be the better domain organization than the tandem-arrangement form. In eukaryotic cells, multidomain proteins with different functions are quite common, and our data indicate that bifunctional ectonucleotidases are functional biochemically. It is intriguing that no such enzyme exists in nature. This might implicate that separating CD73 and CD39 or other E-NTP-Dase family member into different individual proteins might be for the purpose of modulating purinergic signaling in different tissues and cell types. In nature, there are examples in other contexts of such a bifunctional enzyme or a two-independent-protein complex. For instance, peptide amidation is catalyzed by two critical enzymes in some organisms, peptidylglycine α-hydroxylating monooxygenase and peptidyl-α-hydroxyglycine α-amidating lyase, yet in higher organisms they exist as a bifunctional single polypeptide chain.

This study shows a head-to-head enzymatic comparison among several major ectonucleotidases. Regarding the activities toward ATP and ADP, CD39-ECD is much higher than alkaline phosphatase in all pH conditions tested. Acid phosphatase had no such activities at neutral pH while with some at acidic or alkaline pH. As expected, CD73 had no ATPDase activity. For the NMPase activity, CD73 had the highest NMPase activity among three enzymes compared, and its activity was not affected by pH. Alkaline phosphatase had a high activity at alkaline pH, lower activity at neutral pH, and little activity at acidic pH. Acid phosphatase's NMPase activity is higher than that of alkaline phosphatase in neutral and acidic pH. Acid phosphatase had no NMPase activity at alkaline pH. Based on our data, alkaline phosphatase is mainly an NMPase at alkaline and neutral pH with some activities toward ATP and ADP. The result is in line with the data from the rat and mouse alkaline phosphatase in chondrocyte. Loss of function CD73 mutant gene seems compensated by the increased expression of alkaline phosphatases, suggesting ALP is more NMPase. For acid phosphatase, it is also mostly an NMPase at neutral and acidic conditions, with some activity toward ATP and ADP at acidic and alkaline pH. During ATP hydrolysis, both alkaline phosphatase and acid phosphatase sequentially released reaction products of ADP, AMP and adenosine. Our results indicate that CD39-CD73 bifunctional fusions are the only ectonucleotidase that potently hydrolyzed ATP/ADP to adenosine through AMP intermediate under the conditions tested.

Figure 3F:
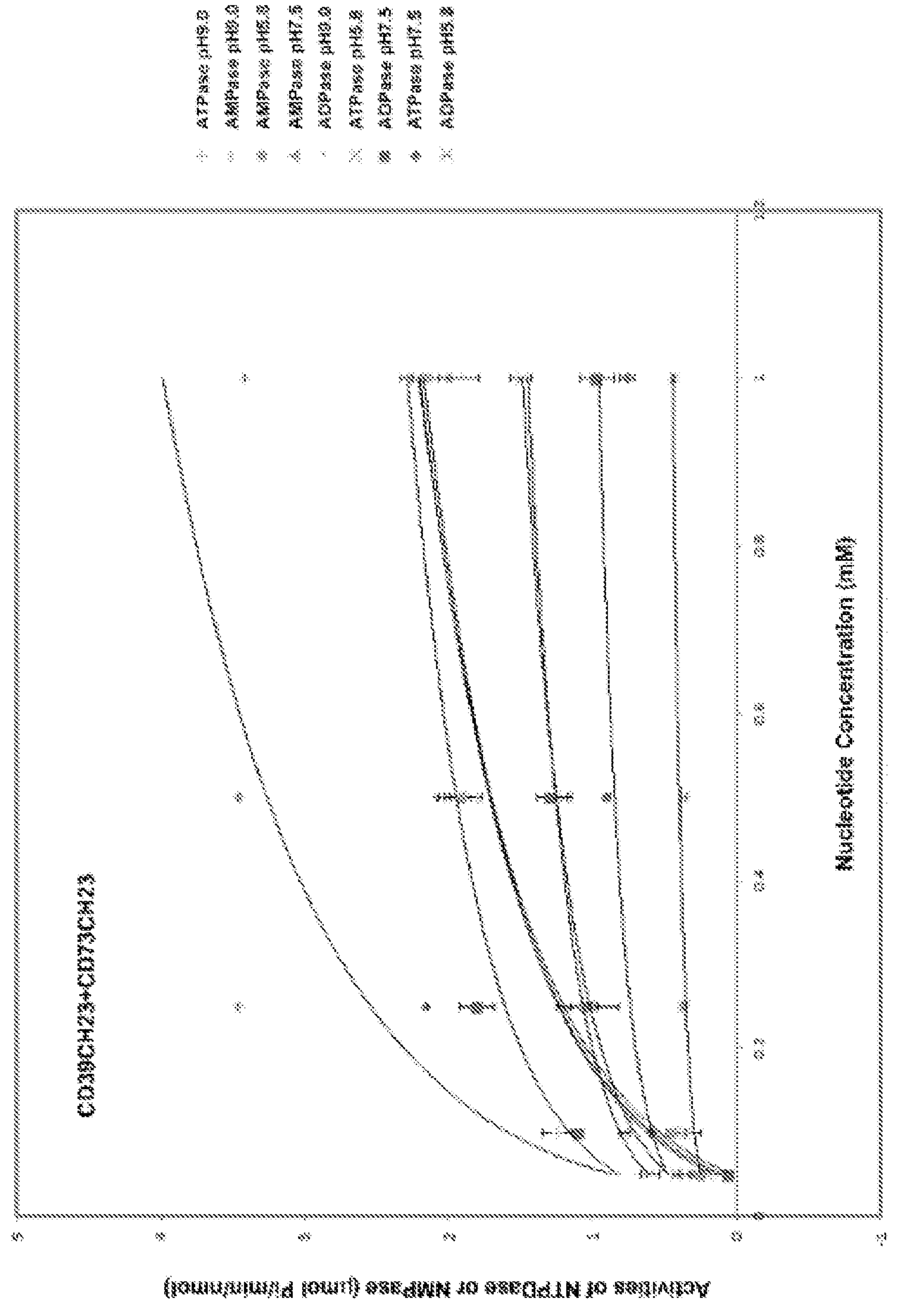

The protein engineering efforts in this study also revealed some interesting observations on the bifunctional fusions and the control proteins. We noticed a pH-sensitivity difference between the bifunctional fusion proteins and the parental fusions. For CD39CH23 fusion, ATPase activity in alkaline and acidic pH was higher than that in neutral pH, whereas its ADPase activity was opposite (FIG. 3B). A similar data was also observed in the mixture of CD39CH23 and CD73CH23 (FIG. 3F). For CD73CH23, AMPase activity was not affected by pH (FIGS. 3E-3F). For the bifunctional fusions, the activities of ATPase, ADPase and AMPase in neutral pH were the highest (FIGS. 4A-4F). Moreover, other ecto-enzymatic property differences were observed between monofunctional fusions and bifunctional functions. Km for ATPase and ADPase of bifunctional fusions were significantly lower than the monofunctional (Table 1 vs. Tables 4 and 5), whereas AMPase activity difference was marginal (Table 2 vs. Tables 4 and 5). These results suggest that CD39's NTPDase activity was more affected by the bifunctional fusions than CD73's NMPase activity. The investigation detected low molecular weight species in some bifunctional fusions, but the activity was not affected.

The study has confirmed that bifunctional enzymes exhibit beneficial therapeutic properties. Similar to soluble CD39, a bifunctional enzyme of the present disclosure could be used to reverse platelet activation, such as in excessive events that contribute to myocardial infarction, restenosis after angioplasty, and stroke. Because of the presence of P1 receptor in platelet, adenosine generated by a bifunctional enzyme would be expected to further modulate the inhibition. Moreover, tissue injury often results in inflammation. ATP released from damage cells activates P2 receptors on all immune cells and trigger pro-inflammatory responses. The bifunctional enzymes not only terminate these responses but also generate immunosuppressive adenosine. Bifunctional enzymes could be used, e.g., to treat patients with high blood pressure. The nucleosides generated by ectonucleotide catalysts would be expected to mediate activities in the vasculature. When sympathetic nerves release ATP, it binds to P2X receptors that result in the constriction of vascular smooth muscles. By breaking down extracellular ATP, the source of agonists for P2X receptors would be depleted, causing a stop in rising blood pressure. In addition, adenosine results in vasodilatation through the binding of adenosine to smooth muscle P1 receptors, and the dilation of blood vessels would decrease blood pressure. The bifunctional enzymes of the present disclosure could, therefore, be used to decrease blood pressure by decreasing extracellular ATP concentration while also increasing extracellular adenosine concentration.

In conclusion, we have demonstrated that a bifunctional enzyme, such as those described herein, that were engineered by fusing the ectodomains of CD39 and CD73, can be used successfully to hydrolyze ATP all the way down to adenosine. A bifunctional enzyme was shown to possess a full activity of sequentially hydrolyzing ATP or ADP mainly via AMP to adenosine. Comparing to human alkaline phosphatase and acid phosphatase, a bifunctional enzyme of the present disclosure was superior in converting tri- and diphosphate nucleotides into nucleosides. The bifunctional enzyme exhibited a pH-sensitivity and enzymatic property difference from the parental molecules. The bifunctional enzyme was found active in platelet clotting assays, providing evidence that a bifunctional CD39/CD73 enzyme can promote therapeutic benefits in vivo by converting pro-inflammatory ATP into anti-inflammatory adenosine.

Example 2. Reduction of Platelet Aggregation

A subject at risk of a pulmonary embolism can be administered a pharmaceutical composition of the present disclosure (e.g., a polypeptide having the amino acid sequence of any one of SEQ ID NOs: 8-11 and variants thereof). The polypeptide may be formulated in a saline solution at pH 7.4 and administered intravenously to the subject. A sample of platelets from the subject is removed and assayed for platelet aggregation via a Lumi-aggregometor Platelets may be incubated at 37° C. and the percent light transmission can be measured. Following administration of the polypeptide, a sample of platelets from the subject can be removed and assayed for aggregation. Following administration of the polypeptide, the subject can be monitored for a reduction of platelet aggregation by at least about 5% to at least about 30% or more.

Example 3. Reduction of Inflammation in Ulcerative Colitis

A subject with ulcerative colitis experiences daily episodes of bowel irritation due to chronic ulcerative colitis. The subject usually experiences 3 to 4 irritable bowel movements per day. Once a week, the subject may undergo intravenous administration of a pharmaceutical composition of the present disclosure (e.g., a polypeptide having the amino acid sequence of any one of SEQ ID NOs: 8-11 and variants thereof). The polypeptide may be formulated in 500 mL saline at a concentration of about 2 mg/kg. Following four dosage administrations of the composition over a treatment period of four weeks, the subject can be monitored for a reduction of irritable bowel movements to about 1 or 2 per day or fewer.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth and follows in the scope of the claims.

Other embodiments are within the claims.

The invention claimed is:

1. A fusion protein comprising a CD39 polypeptide fused to a CD73 polypeptide, wherein the fusion polypeptide comprises an amino acid sequence of any one of SEQ ID NOS: 8-11 or a variant thereof with 90% or greater sequence identity thereto over the full length of any one of SEQ ID NOS: 8-11.

2. The fusion protein of claim 1, wherein:

(i) the CD39 polypeptide has at least 90% sequence identity to the amino acid sequence of SEQ ID NO: 1 over the full length of SEQ ID NO: 1; and/or (ii) the CD73 polypeptide has at least 90% sequence identity to the amino acid sequence of SEQ ID NO: 2 over the full length of SEQ ID NO: 2.

3. A polynucleotide encoding the fusion protein of claim 1.

4. A vector comprising the polynucleotide of claim 3.

5. A cell comprising the polynucleotide of claim 3 or a vector comprising the polynucleotide.

6. A method of producing the fusion protein of claim 1 comprising:

(a) providing a cell transformed with a polynucleotide or vector comprising the polynucleotide encoding the fusion protein;

(b) culturing the transformed cell under conditions for expressing the polynucleotide, wherein the culturing results in expression of the fusion protein; and (c) isolating the fusion protein.

7. A method of hydrolyzing a nucleoside triphosphate (NTP) or nucleoside diphosphate (NDP) to a nucleoside comprising providing the fusion protein of claim 1 and the NTP or NDP and allowing the fusion protein to hydrolyze the NTP or NDP to the nucleoside.

8. The method of claim 7, wherein the NTP is adenosine 5' triphosphate (ATP), the NDP is adenosine 5' diphosphate (ADP), and/or the nucleoside is adenosine.

9. A method of inhibiting platelet aggregation comprising administering the fusion protein of claim 1 to a subject in need thereof, wherein the fusion protein reduces a concentration of extracellular ATP and/or ADP in blood, thereby inhibiting the platelet aggregation.

10. A method of decreasing inflammation in a subject in need thereof comprising administering the fusion protein of claim 1 to the subject, wherein the fusion protein reduces a concentration of extracellular ATP and/or ADP in blood, thereby decreasing the inflammation in the subject.

11. The method of claim 10, wherein the method reduces vascular thrombosis, mechanical perturbation, inflammation in a tissue injury, hypoxia, apoptosis, or blood pressure in the subject.

12. A pharmaceutical composition comprising the fusion protein of claim 1, a polynucleotide encoding the fusion protein, a vector comprising the polynucleotide, or a cell comprising the polynucleotide or vector and a pharmaceutically acceptable carrier.

13. A kit comprising the pharmaceutical composition of claim 12 and instructions for use thereof.

14. The fusion protein of claim 2, wherein the CD39 polypeptide has at least 95% sequence identity to the amino acid sequence of SEQ ID NO: 1 over the full length of SEQ ID NO: 1.

15. The fusion protein of claim 14, wherein the CD39 polypeptide comprises the amino acid sequence of SEQ ID NO: 1.

16. The fusion protein of claim 2, wherein the CD73 polypeptide has at least 95% sequence identity to the amino acid sequence of SEQ ID NO: 2 over the full length of SEQ ID NO: 2.

17. The fusion protein of claim 16, wherein the CD73 polypeptide comprises the amino acid sequence of SEQ ID NO: 2.

18. The fusion protein of claim 1, wherein the fusion protein has at least 95% sequence identity to the amino acid sequence of SEQ ID NO: 8 over the full length of SEQ ID NO: 8.

19. The fusion protein of claim 18, wherein the fusion protein comprises the amino acid sequence of SEQ ID NO: 8.

20. The fusion protein of claim 1, wherein the fusion protein has at least 95% sequence identity to the amino acid sequence of SEQ ID NO: 10 over the full length of SEQ ID NO: 10.

21. The fusion protein of claim 20, wherein the fusion protein comprises the amino acid sequence of SEQ ID NO: 10.

22. The fusion protein of claim 1, wherein the fusion protein has at least 95% sequence identity to the amino acid sequence of SEQ ID NO: 9 over the full length of SEQ ID NO: 9.

23. The fusion protein of claim 22, wherein the fusion protein comprises the amino acid sequence of SEQ ID NO: 9.

24. The fusion protein of claim 1, wherein the fusion protein has at least 95% sequence identity to the amino acid sequence of SEQ ID NO: 11 over the full length of SEQ ID NO: 11.

25. The fusion protein of claim 24, wherein the fusion protein comprises the amino acid sequence of SEQ ID NO: 11.

* * * * *